US008927541B2

(12) United States Patent
Gaucher et al.

(10) Patent No.: US 8,927,541 B2
(45) Date of Patent: Jan. 6, 2015

(54) TRICYCLIC ANTIBIOTICS

(75) Inventors: Bérangère Gaucher, Mulhouse (FR); Franck Hubert Danel, Bruebach (FR); XiaoHu Tang, Beijing (CN); Tong Xie, Haimen (CN); Lin Xu, Shanghai (CN)

(73) Assignee: Basilea Pharmaceutica AG, Basel (CH)

( * ) Notice: Subject to any disclaimer, the term of this patent is extended or adjusted under 35 U.S.C. 154(b) by 172 days.

(21) Appl. No.: 13/511,292

(22) PCT Filed: Dec. 17, 2010

(86) PCT No.: PCT/EP2010/070043
§ 371 (c)(1),
(2), (4) Date: May 22, 2012

(87) PCT Pub. No.: WO2011/073378
PCT Pub. Date: Jun. 23, 2011

(65) Prior Publication Data

US 2012/0245345 A1 Sep. 27, 2012

(30) Foreign Application Priority Data

Dec. 18, 2009 (EP) .................................... 09179956

(51) Int. Cl.
*C07D 491/052* (2006.01)
*C07D 498/14* (2006.01)
*A61K 31/536* (2006.01)
*A61K 31/5365* (2006.01)

(52) U.S. Cl.
USPC ......................... 514/229.5; 544/101; 544/105

(58) Field of Classification Search
USPC ................................ 544/101, 105; 514/229.5
See application file for complete search history.

(56) References Cited

FOREIGN PATENT DOCUMENTS

| | | |
|---|---|---|
| WO | 2006014580 | 2/2006 |
| WO | 2008128953 | 10/2008 |
| WO | 2009125808 | 10/2009 |
| WO | 2009125809 | 10/2009 |
| WO | 2009128019 | 10/2009 |
| WO | 2010015985 | 2/2010 |

OTHER PUBLICATIONS

The International Search Report and Written Opinion by the International Searching Authority, issued on Jan. 19, 2011, in the related PCT application No. PCT/EP2010/070043.

*Primary Examiner* — Kahsay Habte

(57) ABSTRACT

The present invention relates to antibacterial compounds of formula I:

(I)

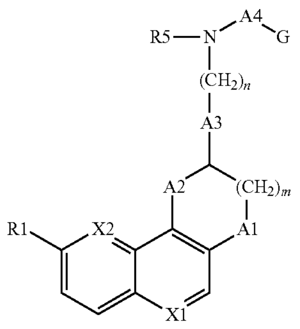

wherein all variable substituents are defined as described herein, which are useful for the treatment of bacterial infections.

47 Claims, No Drawings

TRICYCLIC ANTIBIOTICS

This application is a National Stage Application of PCT/EP2010/70043 filed Dec. 17, 2010, which claims priority from European Patent Application 09179956.9 filed on Dec. 18, 2009. The priority of both said PCT and European Patent Application are claimed.

The present invention relates to antibacterial compounds of a novel tricyclic chemical structure, processes for their manufacture and their use as a medicament for the treatment of bacterial infections.

Several categories of tricyclic derivatives have been described showing antimicrobial activity. Such compounds may be useful as antibiotics for the treatment of microbial infections.

WO2008/128953, for example, describes compounds of formula:

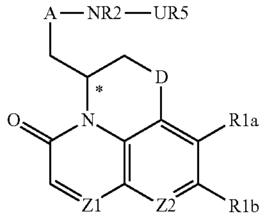

wherein Z1 and Z2 represent nitrogen or (un)substituted CH;

R1a and R1b are hydrogen, halogen, —CN, —$C_1$-$C_6$alkyl, —$CF_3$, —$OCF_3$, etc;

D is —O—, —S—, —$CH_2$—;

A is —$CH_2$—CO—, —$CH_2$—$SO_2$—, —NH—$SO_2$—, —CO—NH—, etc.;

R2 is hydrogen, —$C_1$-$C_4$alkyl, (un)substituted piperidinyl, etc; and

R5 is an optionally substituted bicyclic carbocyclic or heterocyclic ring system.

WO2009/128019 discloses other examples of antibiotic compounds having a tricyclic chemical structure, compound of formula:

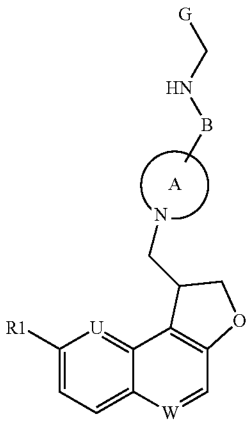

wherein U and W represent nitrogen or (un)substituted CH;

R1 is alkoxy, halogen or CN;

Ring A represents pyrrolidin-1,3-diyl, piperidin-1,3-diyl or morpholin-2,4-diyl;

B is —CH—; and

G is a bicyclic heterocyclic ring system.

Other examples are described e.g. in WO2009/152808 and WO2009/125809:

Example 7

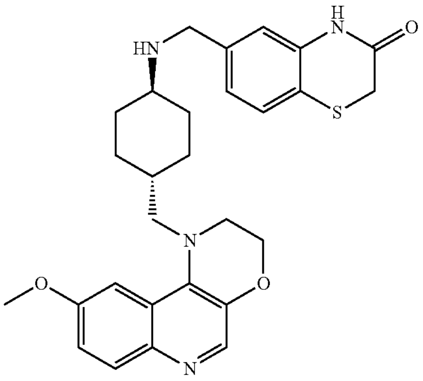

WO2009/125808

Example 19

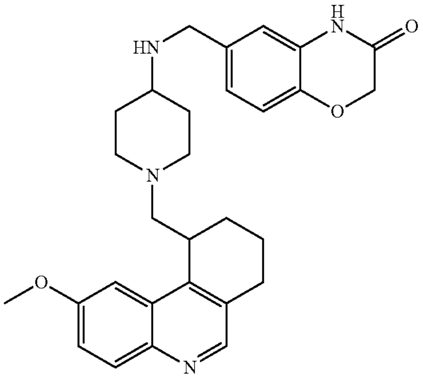

WO2009/125808

Example 37

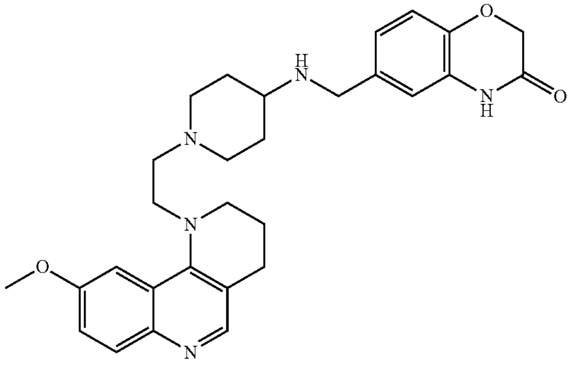

WO2009/125808

As generally known, the antimicrobial resistance against currently available antibacterials is increasing dramatically. Even multidrug resistant strains of Gram-negative bacteria (Pseudomonas, *Klebsiella, Enterobacter, Acinetobacter, Salmonella* species) and Gram-positive organisms (*Staphylococcus, Enterococcus, Streptococcus* species) have emerged and are becoming a serious public health problem. The number of patients with infections for which no effective antibacterial therapy exists increases steadily. This increasing resistance of pathogenic bacteria against known antibacterial agents, including multiple resistances, necessitates a continuous search for novel antibacterial substances, in particular compounds with novel structural characteristics.

The present invention provides such novel compounds, useful for the treatment of microbial infections, in particular novel tricyclic compounds with following general formula (I).

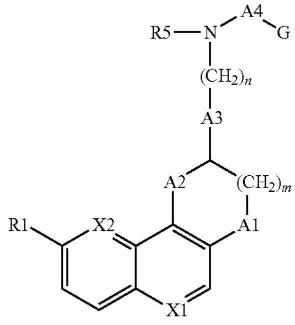

(I)

wherein

A1 represents —O—, —S— or —N—R3;

A2 represents —$CH_2$—, —O—, —N—R4, —C(═O)— or —CH(O—R4)-;

A3 represents $C_3$-$C_8$cycloalkylene; saturated and unsaturated 4 to 8-membered heterocyclodiyl with 1, 2 or 3 heteroatoms selected from nitrogen, oxygen and sulphur, which group A3 is unsubstituted or substituted;

A4 represents $C_1$-$C_4$alkylene, $C_2$-$C_4$alkenylene, >C═O or a group selected from —$C_2H_4NH$—, —$C_2H_4O$—, and —$C_2H_4S$— being linked to the adjacent NR5-group via the carbon atom; and G represents aryl or heteroaryl, which is unsubstituted or substituted and R1 and R2 independently of one another, represent hydrogen or a substituent selected from hydroxy, halogen, mercapto, cyano, nitro, $C_1$-$C_6$alkyl, $C_1$-$C_6$alkoxy, $C_1$-$C_6$alkylthio, $C_1$-$C_6$alkylcarbonyloxy, $C_1$-$C_6$alkylsulfonyloxy, $C_1$-$C_6$heteroalkylcarbonyloxy, $C_5$-$C_6$heterocyclylcarbonyloxy, $C_1$-$C_6$heteroalkoxy, wherein heteroalkyl, heteroalkoxy groups or heterocyclyl comprise 1, 2 or 3 heteroatoms selected from nitrogen, oxygen and sulphur, in which substituents the alkyl moieties are unsubstituted or further substituted;

R3, R4 and R5 independently of one another, represent hydrogen or $C_1$-$C_6$alkyl;

X1 and X2 independently of one another, represent a nitrogen atom or CR2, with the proviso that at least one of X1 and X2 represents a nitrogen atom;

m is 1; and the $(CH_2)_m$ moiety is optionally substituted by $C_1$-$C_4$alkyl; halogen, carboxy, hydroxy, $C_1$-$C_4$alkoxy, $C_1$-$C_4$-alkylcarbonyloxy, amino, mono- or di-($C_1$-$C_4$alkyl) amino or acylamino n is 0, 1 or 2 or a pharmaceutically acceptable salt thereof.

In these new compounds the side chain is linked to the tricyclic system via a new point of attachment, compared to the tricyclic systems already reported in the previous patents.

These compounds are useful antimicrobial agents effective against a variety of human and veterinary pathogens including among others Gram-positive and Gram-negative aerobic and anaerobic bacteria and mycobacteria.

The compounds of the invention or the pharmaceutically acceptable salt thereof also include enantiomers and diastereoisomers of said compounds or salts. Furthermore, in the context of the compounds of the invention the term "compound(s) or pharmaceutically acceptable salt(s) thereof" is meant to include also hydrates and solvates of the compounds of formula (I) and their salts.

The compounds of the invention show potent antibacterial activity against pathogenic bacteria, in particular against at least one of the following Gram-positive and Gram-negative pathogenic bacteria like *staphylococci, streptococci, enterococci, Escherichia coli, Haemophilus influenzae* and *Acinetobacter* baumannii.

The compounds exemplified in this application exhibit a minimum inhibitory concentration (MIC) (mg/L) of less or equal to 8 mg/L against at least one of the following microorganisms: *Acinetobacter baumannii; Enterobacter cloacae; Escherichia coli; Klebsiella pneumoniae; Proteus mirabilis; Pseudomonas aeruginosa; Stenotrophomonas maltophilia; Staphylococcus aureus; Enterococcus faecalis; Staphylococcus epidermidis; Streptococcus pneumoniae; Streptococcus pyogenes; Enterobacter aerogenes; Enterobacter cloacae* and *Enterococcus faecium.*

The expression "$C_1$-$C_6$alkyl" or "$C_1$-$C_4$alkyl" respectively, preferably refers to saturated, straight-chain or branched hydrocarbon groups having from 1 to 6 carbon atoms or 1 to 4 carbon atoms respectively like, for example, methyl, ethyl, propyl, iso-propyl, n-butyl, iso-butyl, tert-butyl, n-pentyl, n-hexyl or 2,2-dimethylbutyl. $C_1$-$C_4$ alkyl is generally preferred. In combined expressions like e.g. $C_1$-$C_6$alk(yl)oxy, $C_1$-$C_6$alkylsulfonyloxy, $C_1$-$C_6$alkyl-carbonyloxy, $C_1$-$C_6$heteroalkyl-carbonyloxy, $C_1$-$C_6$heteroalkoxy, di($C_1$-$C_4$alkyl)amino, $C_1$-$C_6$alkylamine, aralkyl or heteroaralkyl, the term "$C_1$-$C_6$alkyl" is understood in the same way. For the purposes of the present invention alkyl groups may also be substituted, e.g. by fluorine, chlorine, bromine or iodine atoms, carboxy, OH, ═O, SH, ═S, $NH_2$, ═NH, cyano or $NO_2$, $C_1$-$C_4$alkoxy, $C_1$-$C_4$alkoxycarbonyl or mono- or di($C_1$-$C_4$alkyl)amino, phenoxy, $C_5$-$C_6$heterocyclyl or the like.

The term "$C_1$-$C_4$alkylene" refers to divalent saturated straight-chain or branched hydrocarbon groups having from 1 to 4 carbon atoms like, for example, methylene, ethylene, 1,3-propylene, 1,2-propylene, 1,4-butylene and the like. In the same way the term "$C_2$-$C_4$alkenylene" refers to divalent saturated straight-chain or branched hydrocarbon groups having from 2 to 4 carbon atoms like, for example, ethendiyl, propendiyl, like e.g. prop-1-endiyl or prop-2-endiyl or butendiyl residues like 1,4-but-1-enylene or 1,4-buta-1,3-dienylene.

The expression "$C_3$-$C_8$cycloalkylene" preferably refers to a bivalent saturated or partially unsaturated (for example cyclic groups having one, two or more double bonds, such as a cycloalkenylene group), cyclic group containing from 3 to 8 carbon atoms, especially 3, 4, 5, 6 or 7, preferably 5 or 6 ring carbon atoms. Herein "cycloalkylene" is meant to include aromatic groups. The expression $C_3$-$C_8$cycloalkylene refers furthermore to groups in which one or more hydrogen atoms have been replaced each independently of the others by fluorine, chlorine, bromine or iodine atoms, carboxy, alkyl, alkoxy or mono- or di($C_1$-$C_4$alkyl)amino or by OH, ═O, SH, ═S, $NH_2$, ═NH, cyano or $NO_2$ groups, thus, for example, to bivalent residues of cyclic ketones such as, for example, cyclohexanone, 2-cyclohexenone or cyclopentanone. Further specific examples of cycloalkylene groups are cyclobutylene, cyclopentylene, cyclohexylene, cyclopentenylene, cyclohexadienylene.

The expression "heterocyclodiyl" as used herein preferably refers to a saturated or unsaturated bivalent 4 to 8-membered cyclic group as defined above in connection with the definition of cycloalkylene (including divalent heteroaromatic groups like e.g. pyrazol-diyl), in which one or more (preferably 1, 2 or 3) ring carbon atoms have been replaced each independently of the other by an oxygen, nitrogen or sulphur atom, preferably by a nitrogen atom. The expression heterocyclodiyl preferably refers furthermore to groups in which one or more hydrogen atoms have been replaced each independently of the others by fluorine, chlorine, bromine or iodine atoms or by, carboxy, alkyl, alkoxy or mono- or di($C_1$-$C_4$alkyl)amino or by OH, =O, SH, =S, $NH_2$, =NH, cyano or $NO_2$ groups. Examples are piperidin-diyl, piperazin-diyl, morpholin-diyl, pyrrolidin-diyl, tetrahydro-thiophenyl-diyl, tetrahydropyran-diyl, tetrahydrofuran-diyl or 2-pyrazolin-diyl. Preferred are saturated 4 to 6-membered heterocyclodiyl groups in which one or two ring carbon atoms have been replaced by an oxygen or preferably nitrogen atom.

The expression "aryl" as used herein preferably refers to an aromatic group that contains one or more rings and from 6 to 14 ring carbon atoms, preferably from 6 to 10 (especially 6) ring carbon atoms. The expression aryl refers furthermore to such groups in which one or more hydrogen atoms have been replaced each independently of the others by alkyl, fluorine, chlorine, bromine or iodine atoms or by carboxy, alkoxy, mono- or di($C_1$-$C_4$alkyl)amino, OH, $NH_2$, cyano or $NO_2$ groups. Examples are phenyl, 4-methyl-phenyl, 4-tert-butyl-phenyl; 3-fluoro-4-methyl-phenyl, 3-fluoro-4-(trifluoromethyl)-phenyl; naphthyl, biphenyl, 2-fluorophenyl, anilinyl, 3-nitro-phenyl or 4-hydroxyphenyl.

The expression "heteroaryl" as used herein preferably refers to an aromatic group that contains one or more rings and from 5 to 14 ring atoms, preferably from 5 to 10 (especially 5, 6, 8, 9 or 10) ring atoms, and contains one or more (preferably 1, 2, 3 or 4) oxygen, nitrogen or sulphur ring atoms. The expression heteroaryl refers furthermore to groups in which one or more hydrogen atoms have been replaced each independently of the others by fluorine, chlorine, bromine or iodine atoms or by carboxy, alkyl, alkoxy, mono- or di($C_1$-$C_4$alkyl)amino, OH, SH, $NH_2$, cyano, $NO_2$ or unsubstituted heteroaryl groups. Examples are pyridyl, imidazolyl, thiophenyl, thieno[3,2-b]thiophenyl, benzo[b]thiophenyl, furanyl, benzofuranyl, imidazolyl, benzimidazolyl, pyrrolyl, indolyl, oxazolyl, isoxazolyl, indazolyl, indolyl, pyridazinyl, quinolinyl, purinyl, carbazolyl, acridinyl, pyrimidyl, pyrazolyl and isoquinolinyl groups.

Further rings can be fused to the aryl and heteroaryl groups as defined above, in particular further cycloalkane and/or in particular heterocycloalkane groups.

For the purposes of this invention the term "cycloalkane" preferably refers to a saturated or partially unsaturated cyclic group which contains one or more, e.g. one or two rings and from 3 to 14 ring carbon atoms, preferably from 3 to 10, most preferably 5 or 6 ring carbon atoms. The term cycloalkane refers furthermore to such groups in which one or more hydrogen atoms have been replaced each independently of the others by fluorine, chlorine, bromine or iodine atoms or by carboxy, alkyl, alkoxy, mono- or di($C_1$-$C_4$alkyl)amino or by OH, =O, SH, =S, $NH_2$, =NH, cyano or $NO_2$ groups, thus, for example, cyclic ketones such as, for example, cyclohexanone or cyclopentanone. Further specific examples of cycloalkane groups are cyclopropane, cyclobutane, cyclopentane, cyclohexane, cyclopentene, cyclohexadiene.

The expression "heterocycloalkane" as used herein preferably refers to cycloalkane groups as defined above in which one or more, preferably 1, 2 or 3 ring carbon atoms have been replaced each independently of the others by an oxygen, nitrogen or sulphur atom. A heterocycloalkane group has preferably 1 or 2 ring(s) containing from 3 to 10, most preferably 5 or 6 ring atoms. The expression heterocycloalkane refers furthermore to groups in which one or more hydrogen atoms have been replaced each independently of the others by fluorine, chlorine, bromine or iodine atoms or by carboxy, alkyl alkoxy, mono- or di($C_1$-$C_4$alkyl)amino or by OH, =O, SH, =S, $NH_2$, =NH, cyano or $NO_2$ groups. Examples are a piperidine, piperazine, morpholine, pyrrolidine, thiomorpholine, tetrahydrothiophene, [1,4]dioxane, tetrahydropyrane, tetrahydrofurane or pyrazoline and also lactams, lactones, cyclic imides and cyclic anhydrides, like e.g., morpholin-3-one or thiomorpholin-3-one.

The expression halogen refers to fluorine, chlorine bromine and iodine.

Certain compounds of formula (I) may contain one, two or more centres of chirality. The present invention therefore includes both all pure enantiomers and all pure diastereoisomers and also mixtures thereof in any mixing ratio. The present invention moreover also includes all cis/trans-isomers of the compounds of the general formula (I) and mixtures thereof. The present invention moreover includes all tautomeric forms of the compounds of formula (I).

Preferred are compounds of formula (I) wherein X1 represents a nitrogen atom and X2 represents a group CR2, in particular CH.

Particularly preferred are furthermore the compounds according to the invention, wherein R1 is selected from halogen and $C_1$-$C_6$alkoxy, preferably $C_1$-$C_4$alkoxy, in particular from fluoro and methoxy.

Additionally preferred are the compounds according to the invention wherein R1 is selected from hydrogen, hydroxy, mercapto, cyano, nitro, $C_1$-$C_6$alkylsulfonyloxy, $C_1$-$C_6$alkylcarbonyloxy, $C_1$-$C_6$heteroalkylcarbonyloxy, $C_5$-$C_6$heterocyclylcarbonyloxy.

The group R2 of the compounds according to the present invention is preferably selected from hydrogen, halogen, $C_1$-$C_6$alkyl, $C_1$-$C_6$alkoxy.

Another preferred group of the compounds according to the present invention are those, wherein A3 represents a group selected from unsubstituted $C_5$-$C_6$cycloalkylene and unsubstituted saturated 4 to 6-membered heterocyclodiyl comprising one or two nitrogen atoms as the heteroatoms, in particular the compounds of formula (I) wherein A3 is selected from:

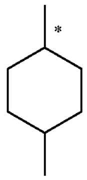,
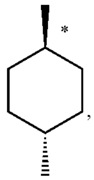,
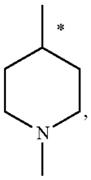,
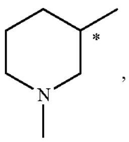,
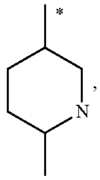,
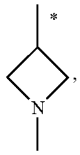,
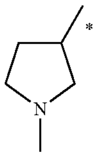
and
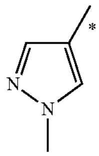, wherein

* indicates the bond to the $(CH_2)_n$ group in formula (I).

More preferably A3 is

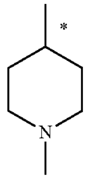 and 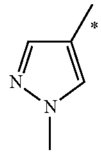,

Other preferred embodiments of A3 include e.g.:

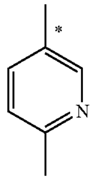 and 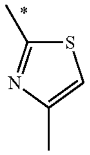 or 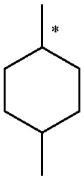 and 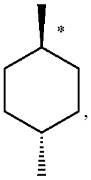,

Particularly preferred are the compounds of formula (I) wherein A3 is unsubstituted or substituted with groups selected from hydroxy, $C_1$-$C_4$alkyl and carboxy.

The group G in formula (I) represents preferably a $C_6$-$C_{10}$aryl group which is unsubstituted or further substituted by one or more halogen atoms, in particular chloro or fluoro, and/or straight-chain or branched $C_1$-$C_4$alkyl groups which may optionally be further substituted by fluoro, like e.g. trifluoromethyl; or a phenyl group or a 5- or 6-membered heteroaryl group comprising heteroatoms selected from oxygen, sulphur or nitrogen, which phenyl group or 5- or 6-membered heteroaryl group are unsubstituted or substituted by one or more halogen atoms, in particular chloro or fluoro, and/or straight-chain or branched $C_1$-$C_4$alkyl groups which may optionally be further substituted by fluoro, like e.g. trifluoromethyl, or by an unsubstituted 5- or 6-membered heteroaryl group, to which phenyl group or 5- or 6-membered heteroaryl group further optionally a benzene ring or a 5- or 6-membered heteroarene ring, which is unsubstituted or substituted by one or more halogen atoms, in particular chloro or fluoro, and/or straight-chain or branched $C_1$-$C_4$alkyl groups which may optionally be further substituted by fluoro, like e.g. trifluoromethyl, or a heterocyclalkane ring may be fused which comprises six ring atoms and heteroatoms selected from oxygen, sulphur or nitrogen and optionally a =O group as substituent.

Particularly preferred as group G are the following groups:

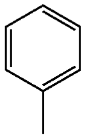, 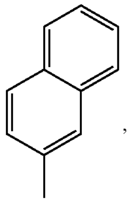, 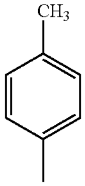, 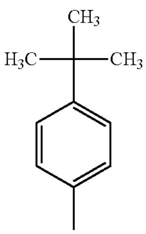,

-continued

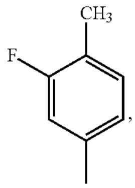, 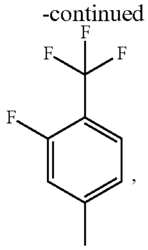, 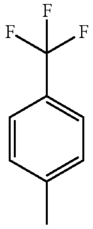,

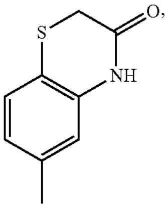 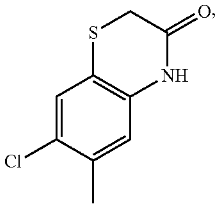

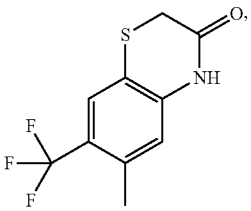 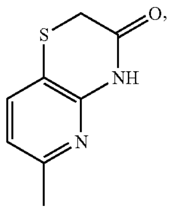

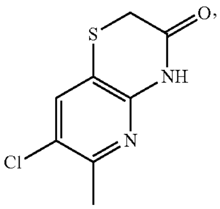 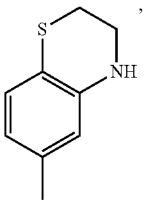,

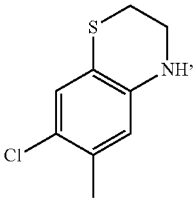 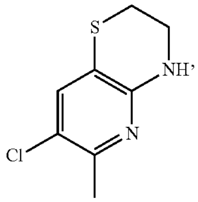

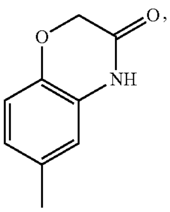 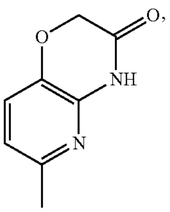 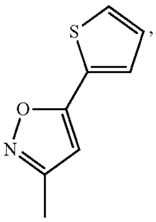,

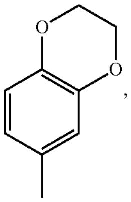, 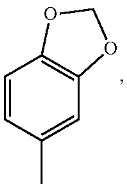, 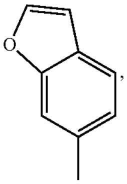,

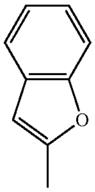, 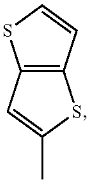 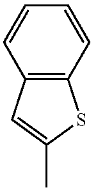 and 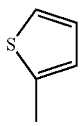.

More preferably, G is selected from the groups of formula:

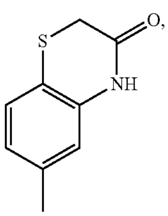,

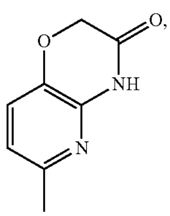,

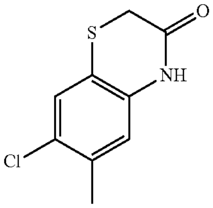

and

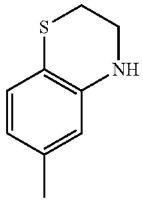.

Particularly preferred in view of antibacterial activity are the compounds of formula (I) wherein A1 represents —O— or —S— and A2 represents —O— or —$CH_2$—.

Particularly preferred are also the compounds of formula (I) wherein R3 and R4 are hydrogen atoms.

Preferred are also the compounds of formula (I) wherein R5 is a hydrogen atom or a methyl group.

The compounds of formula (I) wherein n is 0 are yet a further preferred group of the compounds of the present invention.

The aforementioned preferences can of course also be combined in any possible manner and all these combinations are considered to be embodiments of the present invention. A specific embodiment of the present invention is the group of compounds of formula I having 2 or more, preferably all, of the following specific features in combination:

(a) X1 is a nitrogen atom and

X2 is CH;

(b) A1 is —S— or preferably —O—;

(c) A2 is —$CH_2$—;

(d) A3 is

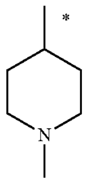

or

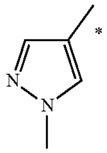

;

(e) G is selected from a group of formula:

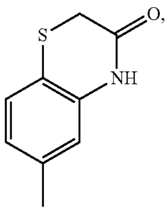,

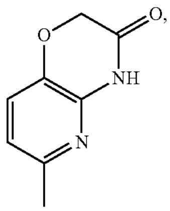

-continued

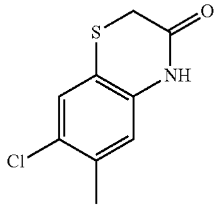

and

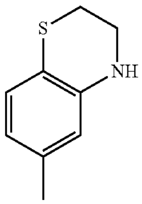.

(f) n is 0;

(g) A4 is $C_1$-$C_4$alkylene, in particular methylene; or >C=O;

(h) R1 is $C_1$-$C_4$alkoxy, in particular methoxy.

Also preferred are compounds of formula (I) wherein X1 represents a nitrogen atom and X2 represents a nitrogen atom.

Additionally preferred are the compounds according to the invention wherein R1 is $C_1$-$C_3$alkyl.

Another preferred group of the compounds according to the present invention are those, wherein A3 represents a group selected from unsubstituted or substituted, saturated or unsaturated 4 to 6-membered heterocyclodiyl comprising one or two heteroatoms selected from nitrogen, oxygen and sulphur.

Additionally preferred are the compounds of formula (I) wherein A3 is unsubstituted or substituted with groups selected from $C_1$-$C_4$alkoxy, cyano, aminocarbonyl, ($C_1$-$C_4$alkyl)aminocarbonyl, $C_1$-$C_4$alkoxycarbonyl, carboxylic acid.

Particularly preferred in view of antibacterial activity are the compounds of formula (I) wherein A1 represents —O— or —S— and A2 represents —$CH_2$— or —NH—.

Examples of pharmacologically acceptable salts of the compounds of formula (I) are salts of physiologically acceptable mineral acids, such as hydrochloric acid, sulphuric acid and phosphoric acid, or salts of organic acids, such as methane-sulphonic acid, p-toluenesulphonic acid, lactic acid, acetic acid, trifluoroacetic acid, citric acid, succinic acid, fumaric acid, maleic acid and salicylic acid. Further examples of pharmacologically acceptable salts of the compounds of formula (I) are alkali metal and alkaline earth metal salts such as, for example, sodium, potassium, lithium, calcium or magnesium salts, ammonium salts or salts of organic bases such as, for example, methylamine, dimethylamine, triethylamine, piperidine, ethylenediamine, lysine, choline hydroxide, meglumine, morpholine or arginine salts.

The compounds of formula (I) may also be solvated, especially hydrated. Solvation and hydration may take place, for example, during the preparation process. The compounds according to the invention are therefore considered to include hydrates and solvates.

The compounds according to the present invention, pharmaceutically acceptable salts, solvates, hydrates thereof can be prepared e.g. by one of the processes (a), (b), (c), (d), (e), (f), (g) or (h) described below; followed, if necessary, by: removing any protecting groups; forming a pharmaceutically acceptable salt; or forming a pharmaceutically acceptable solvate or hydrate.

Process (a):

In this process variant a compound of formula I is prepared by reacting a compound of formula II (II)

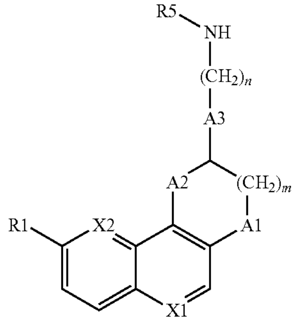

with a compound of formula III

G-A4b-L0 (III)

in which formulae

X1, X2, R1, R5, A1, A2, A3, G, m and n are as defined above for formula I,

L0 is selected from —$CH_2$Y, —CHO, —COOH and —COCl,

Y is a leaving group like mesylate, tosylate, triflate or halogen,

A4b is absent or represents $C_1$-$C_3$alkylene, $C_2$-$C_3$alkenylene; or a group selected from —$CH_2$NH—, —$CH_2$O—, and —$CH_2$S—, said group being linked to G via the nitrogen, oxygen or sulfur atom, In certain cases L0 may require appropriate activation to allow a reaction of compounds of formulae II and III as described in more detail below.

Process (b):

In this process variant a compound of formula I is prepared by reacting a compound of formula IV (IV)

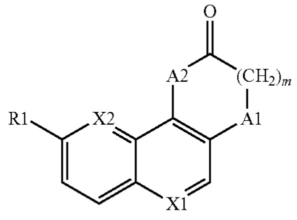

with a compound of formula V (V)

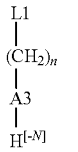

to generate a compound of formula VI (VI)

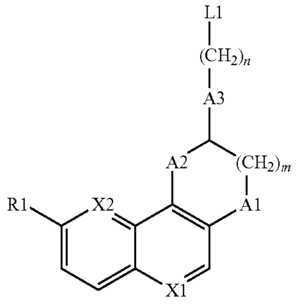

in which formulae

X1, X2, R1, A1, A2, m and n are as in formula I,

A3 is an unsubstituted or substituted, saturated or unsaturated 4 to 8-membered heterocyclodiyl group with 1, 2 or 3 heteroatoms selected from nitrogen, oxygen and sulphur, at least one of which heteroatoms is a nitrogen atom which group A3 is linked to the moiety

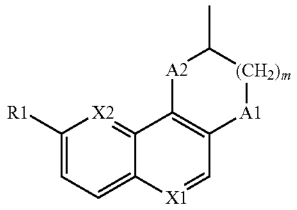

via a nitrogen ring atom of A3, $H^{[-N]}$ in formula V represents a hydrogen atom bound to said nitrogen ring atom of A3, and L1 is nitro or N(R5)E.

When L1 is nitro, said nitro group is reduced to an amino group and the amino derivative obtained is reacted with a compound of formula III G-A4b-L0 (III):

wherein G, A4b and L0 are as defined above for Process (a).

When L1 is N(R5)E, then R5 is as in formula I, and

E is -A4-G (A4 and G being as defined in formula I) or an amino protecting group PG1, such as allyloxycarbonyl, benzyloxycarbonyl, 9-fluorenylmethylcarbonyl, tert-butoxycarbonyl or benzyl.

When E is an amino protecting group, said protecting group is removed and the deprotected intermediate is reacted with a compound of formula III G-A4b-L0 (III):

wherein G, A4b and L0 are as defined above.

Again L0 may, in certain cases, require appropriate activation to allow connection of the deprotected intermediate and the compound of formula III.

Process (c):

This process variant can be used for the manufacture of compounds of formula I as defined above, wherein A1 is —O— and A2 is —$CH_2$—.

In this process a compound of formula VII (VII)

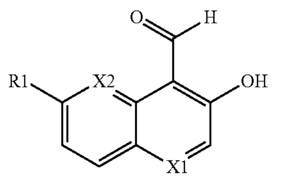

is reacted with a compound of formula VIII (VIII)

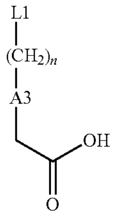

to generate a compound of formula IX (IX)

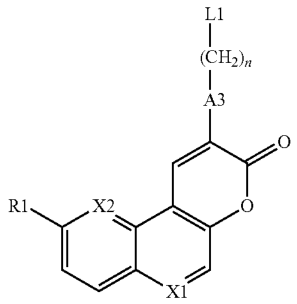

in which formulae

X1, X2, R1 and n are as in formula I,

A3 is an unsubstituted or substituted, saturated or unsaturated 4 to 8-membered heterocyclodiyl group with 1, 2 or 3 heteroatoms selected from nitrogen, oxygen and sulphur, at least one of which heteroatoms is nitrogen atom which group A3 is linked to the moiety

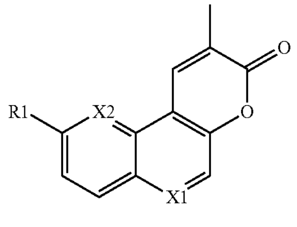

in formula IX via a nitrogen ring atom of A3, said nitrogen heteroatom of A3 being linked to the terminal $-CH_2-COOH$ in the compound of formula VIII, L1 is nitro or N(R5)E, R5 is as in formula I, and E is an amino protecting group PG1 or a group of formula -A4-G, wherein A4 and G have the same meaning as in formula I.

The compound of formula IX is further reduced and cyclized to generate a compound of formula XI (XI)

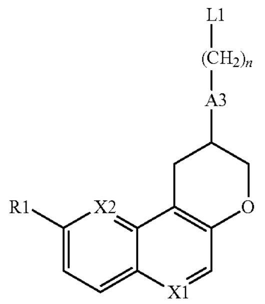

wherein X1, X2, R1, A3, L1 and n are as defined above.

Compound of formula XI is finally transformed and reacted with a compound of formula III G-A4b-L0 (III):

wherein G, A4b and L0 are as defined above to generate compound of formula I following the procedures described in process (b).

Process (d):

This process variant can be used for the manufacture of compounds of formula I as defined above, wherein A2 is —O— or —N—R4.

In this variant a compound of formula XIII (XIII)

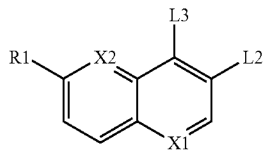

is reacted with a compound of formula XIV (XIV)

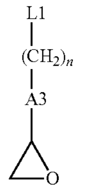

to generate a compound of formula XV (XV)

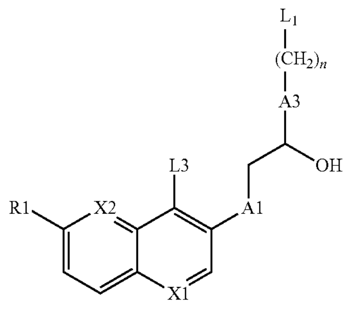

in which formulae

A1, A3, R1, R4, X1, X2 and n are as in formula I,

L1 is nitro or N(R5)E,

R5 is as in formula I, and

E is an amino protecting group PG1 or a group of formula -A4-G, wherein

A4 and G have the same meaning as in formula I;

L2 is -A1-H,

L3 is a halogen atom or —N(R4)PG2 wherein PG2 is an amino protecting group, said compound of formula XV is then converted to the compound of formula XVI (XVI)

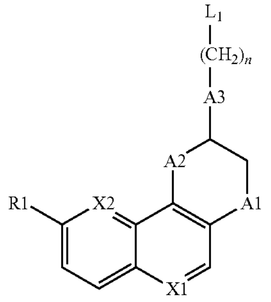

wherein A1, A2, A3, X1, X2, L1, R1 and n are as defined above, and when L1 is nitro, said nitro group is reduced to an amino group and the amino derivative obtained is reacted with a compound of formula III G-A4b-L0 (III), wherein L0 is selected from —$CH_2$Y, —CHO, —COOH and —COCl, Y is mesylate, tosylate, triflate or halogen, and A4b is absent or represents $C_1$-$C_3$alkylene, $C_2$-$C_3$alkenylene or a group selected from —$CH_2$NH—, —$CH_2$O—, and —$CH_2$S—, said group being linked to G via the nitrogen, oxygen or sulfur atom; or when L1 is N(R5)E and E is an amino protecting group said protecting group is removed and the deprotected intermediate is reacted with a compound of formula III as defined above.

Process (e):

This process variant can be used for the manufacture of compounds of formula I, wherein A2 is —$CH_2$— or —N—R4. In this variant a compound of the formula XIII (XIII)

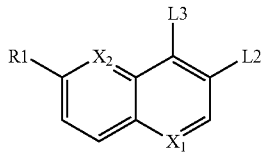

is reacted with a compound of formula XVIII (XVIII)

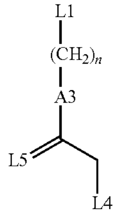

to generate a compound of formula XIX (XIX)

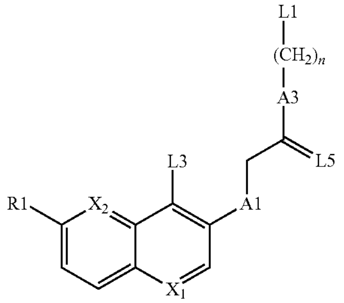

in which formulae

X1, X2, R1, A1, A3 and n are as defined above for formula I,

L1 is nitro or N(R5)E,

R5 is as in formula I, and

E is an amino protecting group PG1 or a group of formula -A4-G, wherein

A4 and G have the same meaning as in formula I;

L2 is -A1-H,

L3 is a halogen atom or —N(R4)PG2 wherein PG2 is an amino protecting group (such as allyloxycarbonyl, benzyloxycarbonyl, 9-fluorenylmethylcarbonyl, tert-butoxycarbonyl or benzyl), L4 is a halogen atom, L5 is $CH_2$ or O.

The compound of formula XIX is further transformed and cyclized to generate a compound of formula XX (XX)

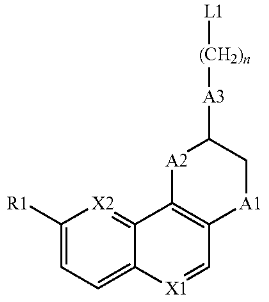

wherein A1, A2, A3, X1, X2, L1, R1 and n are as defined above.

Compound of formula XX is finally transformed and reacted with a compound of formula III G-A4b-L0 (III):

wherein G, A4b and L0 are as defined above to generate compound of formula I following the procedures described in process (b).

Process (f):

This process variant can be used for the manufacture of compounds of formula I as defined above, wherein A1 is —O— and A2 is —$CH_2$—.

In this process a compound of formula VII (VII)

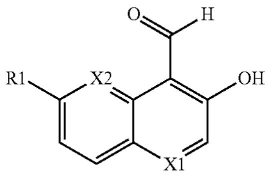

is reacted with a compound of formula XXII (XXII)

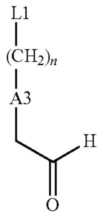

to generate a compound of formula XXIII (XXIII)

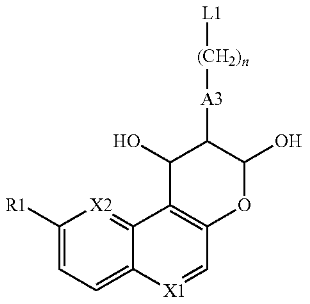

in which formulae

X1, X2, R1, A3 and n are as in formula I,

L1 is nitro or N(R5)E,

R5 is as in formula I, and

E is an amino protecting group PG1 or a group of formula -A4-G, wherein

A4 and G have the same meaning as in formula I.

The compound of formula XXIII is then converted to the compound of formula X (X)

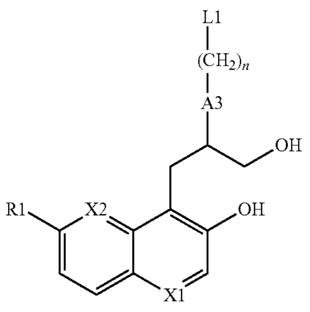

wherein X1, X2, R1, A3, L1 and n are as defined above.

Compound of formula X is further transformed into compound of formula XI (XI)

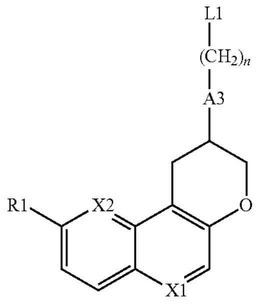

wherein X1, X2, R1, A3, L1 and n are as defined above.

Said compound of formula XI is finally converted into compound of formula I following the procedures described in processes (b) and (c).

Process (g):

This process variant can be used for the manufacture of compounds of formula I, wherein A1 is —N—R3 and A2 is —O—.

In this variant a compound of the formula XXV (XXV)

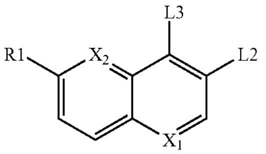

is reacted with a compound of formula XXVI (XXVI)

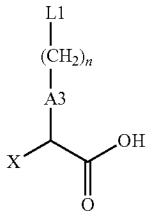

to generate a compound of formula XXVII (XXVII)

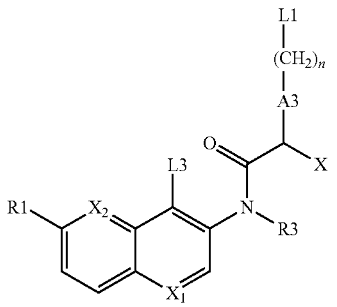

in which formulae

X1, X2, A3, R1, R3 and n are as defined above for formula I,

L1 is nitro or N(R5)E,

R5 is as in formula I, and

E is an amino protecting group PG1 or a group of formula -A4-G, wherein

A4 and G have the same meaning as in formula I,

L2 is —NHR3 or —N(R3)PG2 wherein PG2 is an amino protecting group,

L3 is —OH or —OPG3 wherein PG3 is a phenol protecting group (such as benzyl, allyl, tetrahydropyranyl, tert-butyl dimethylsilyl), X is a halogen atom.

The compound of formula XXVII is further transformed and cyclized to generate a compound of formula XXVIII (XXVIII)

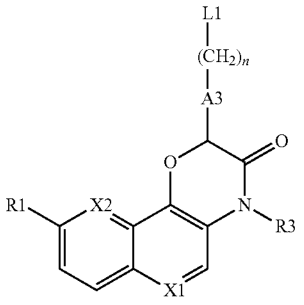

wherein A3, X1, X2, L1, R1, R3 and n are as defined above.

Said compound of formula XXVIII is then reduced into compound of formula XXIX (XXIX)

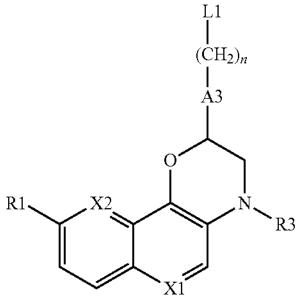

wherein A3, X1, X2, L1, R1, R3 and n are as defined above.

Compound of formula XXIX is finally transformed and reacted with a compound of formula III G-A4b-L0 (III):

wherein G, A4b and L0 are as defined above to generate compound of formula I following the procedures described in process (b).

Process (h):

This process variant can be used for the manufacture of compounds of formula I as defined above, wherein A1 is —N—R3 and A2 is $—CH_2—$.

In this process a compound of formula XXXI (XXXI)

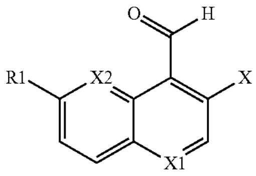

is reacted with a compound of formula XXII (XXII)

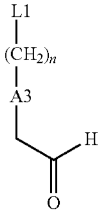

to generate a compound of formula XXXII (XXXII)

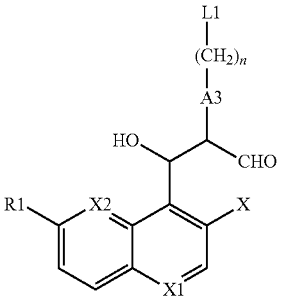

in which formulae

X1, X2, R1, A3 and n are as in formula I,

L1 is nitro or N(R5)E,

R5 is as in formula I, and

E is an amino protecting group PG1 or a group of formula -A4-G, wherein

A4 and G have the same meaning as in formula I,

X is a halogen atom.

Compound of formula XXXII is further converted into a compound of formula XXXV (XXXV)

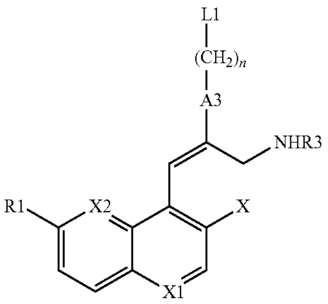

wherein X1, X2, R1, R3, A3, L1 and n are as defined above,

Compound of formula XXXV is further cyclized and reduced to generate compound of formula XXXVII (XXXVII)

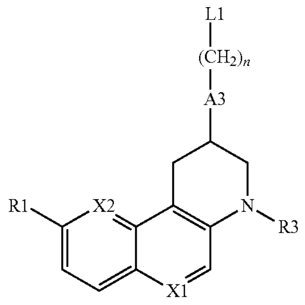

wherein X1, X2, R1, R3, A3, L1 and n are as defined above,

Said compound of formula XXXVII is finally converted into compound of formula I following the procedures described in process (b).

The necessary starting materials for the synthetic methods as described herein, if not commercially available, may be made by procedures which are described in the scientific literature, or could be made from commercially available compounds using adaptations of processes reported in the scientific literature. The reader is further referred to *Advanced Organic Chemistry,* $5^{th}$ Edition, by J. March and M. Smith, published by John Wiley & Sons, 2001, for general guidance on reaction conditions and reagents.

Furthermore in some of the reactions mentioned herein it may be necessary or desirable to protect any sensitive groups in compounds. Conventional protecting groups may be used in accordance with standard practice (for illustration see *Protective Groups in Organic Synthesis,* $3^{rd}$ Edition, by T. W. Greene and P. G. M. Wuts, published by John Wiley & Sons, 1999).

The protecting groups may be removed at any convenient stage in the synthesis using conventional techniques well known in the art, or they may be removed during a later reaction step or work-up.

Scheme 1

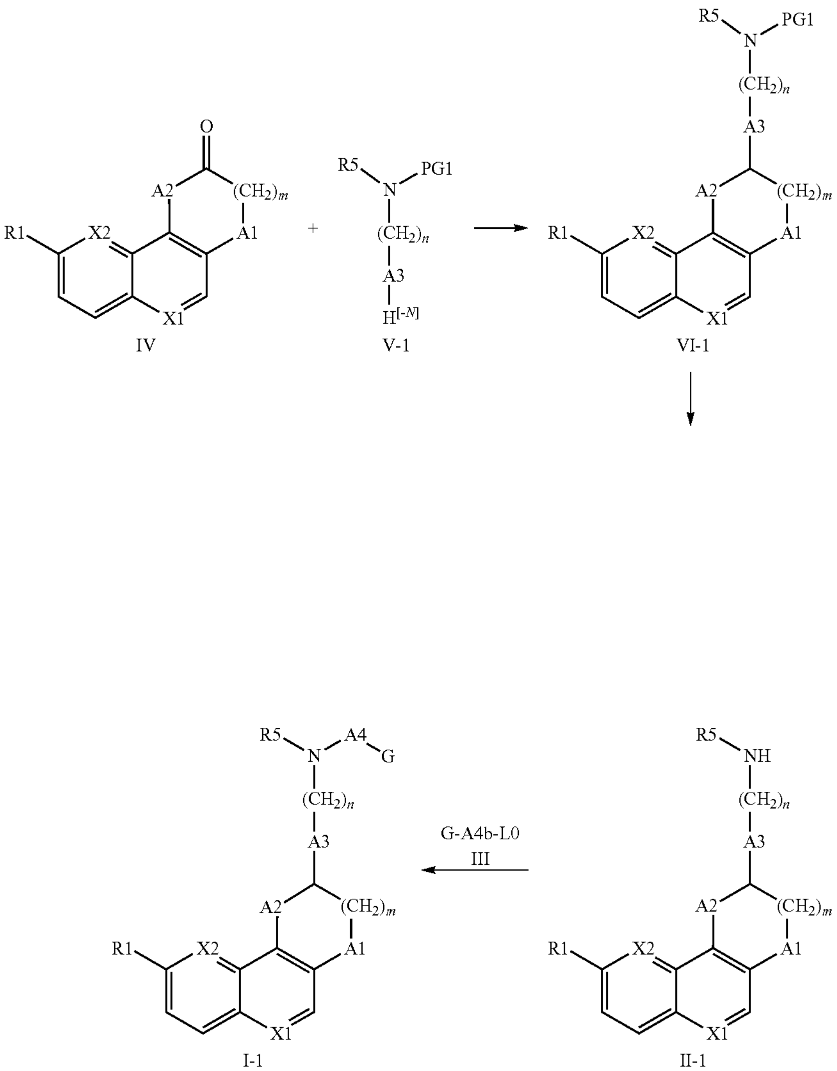

IV V-1 VI-1 I-1 II-1

In Scheme 1, PG1 is an amino protecting group (such as allyloxycarbonyl (Alloc), benzyloxycarbonyl, 9-fluorenylmethylcarbonyl (Fmoc), tert-butoxycarbonyl (Boc) or benzyl) and the other symbols have the same meanings as previously described.

Compounds of formula V-1 are usually obtained by reacting the corresponding free amine with allyl, fluorenylmethyl or benzyl chloroformate or with di-tert-butyl dicarbonate in presence of a base such as sodium hydroxide, sodium hydrogencarbonate, triethylamine, 4-dimethylaminopyridine or imidazole. They can also be protected as N-benzyl derivatives by reaction with benzyl bromide or chloride in presence of a base such as sodium carbonate or triethylamine. Alternatively, N-benzyl derivatives can be obtained through reductive amination in presence of benzaldehyde. Further strategies to introduce other amino protecting groups have been described in *Protective Groups in Organic Synthesis,* 3rd Edition, by T. W. Greene and P. G. M. Wuts, published by John Wiley & Sons, 1999.

The reductive amination reaction between ketones of formula IV and amines of formula V-1 to generate compounds of formula VI-1 is conducted in a solvent system allowing the removal of the formed water through physical or chemical means (e.g. distillation of the solvent-water azeotrope or presence of drying agents such as molecular sieves, magnesium sulfate or sodium sulfate). Such solvent is typically toluene, n-hexane, tetrahydrofuran, dichloromethane N,N-dimethylformamide, N,N-dimethylacetamide, acetonitrile, 1,2-dichloroethane or mixture of solvents such as methanol-1,2-dichloroethane. The reaction can be catalyzed by traces of acid (usually acetic acid). The intermediate imine is reduced subsequently or simultaneously with a suitable reducing agent (e.g. sodium borohydride, sodium cyanoborohydride, sodiumtriacetoxyborohydride; R. O. and M. K. Hutchins, *Comprehensive Organic Synthesis*, B. M. Trost, I. Fleming, Eds; Pergamon Press: New York (1991), vol. 8, p. 25-78) or through hydrogenation over a noble metal catalyst such as palladium on activated carbon. The reaction is usually carried out between −10° C. and 110° C., preferably between 0° C. and 60° C. The reaction can also be carried out in one pot. It can also be performed in protic solvents such as methanol or water in presence of a picoline-borane complex (Tetrahedron, 2004, 60, 7899).

Removal of the protecting group PG1 in compounds of formula VI-1 is carried out under standard conditions to generate compounds of formula II-1. For example the benzyl carbamates are deprotected by hydrogenolysis over a noble metal catalyst (e.g. palladium or palladium hydroxide on activated carbon). The Boc group is removed under acidic conditions such as hydrochloric acid in an organic solvent such as methanol, dioxane or ethyl acetate, or trifluoroacetic acid neat or diluted in a solvent such as dichloromethane. The Alloc group is removed in presence of a palladium salt such as palladium acetate or tetrakis(triphenylphosphine)palladium (0) and an allyl cation scavenger such as morpholine, pyrrolidine, dimedone or tributylstannane between 0° C. and 70° C. in a solvent such as tetrahydrofuran. The N-benzyl protected amines are deprotected by hydrogenolysis over a noble metal catalyst (e.g. palladium hydroxide on activated carbon). The Fmoc protecting group is removed under mild basic conditions such as diluted morpholine or piperidine in N,N-dimethylformamide or acetonitrile. Further general methods to remove amine protecting groups have been described in *Protective Groups in Organic Synthesis,* 3rd Edition, by T. W. Greene and P. G. M. Wuts, published by John Wiley & Sons, 1999.

Compounds of formula I-1 wherein A4 is $CH_2$ can be obtained via reductive amination between intermediate II-1 and compound of formula III wherein L0 is —CHO following procedures previously described for the preparation of compounds of formula VI-1.

Alternatively, compounds of formula I-1 wherein A4 is $—CH_2—$ can be obtained from intermediate amine II-1 by reaction with a compound of formula III wherein L0 is $—CH_2Y$ and Y is a leaving group like mesylate, tosylate, triflate or halogen at a temperature between −20° C. and 100° C. in a dry aprotic solvent like dichloromethane, acetonitrile, N,N-dimethylformamide, dimethyl sulfoxide or tetrahydrofuran without or with an inorganic base such as potassium carbonate or cesium carbonate, or an organic base such as triethylamine or N,N-diisopropylethylamine. Formation of the mesylate, tosylate or triflate compound can be achieved by reacting the corresponding alcohol with methanesulfonyl chloride or methanesulfonic anhydride, p-toluenesulfonyl chloride, trifluoromethanesulfonyl chloride or trifluoromethanesulfonic anhydride, respectively, in presence of a base such as triethylamine or the like in a dry aprotic solvent such as pyridine, acetonitrile, tetrahydrofuran or dichloromethane between −30° C. and 80° C.

Compounds of formula I-1 wherein A4 is >C(═O) can be obtained from intermediate amine II-1 through reaction with a carboxylic acid derivative III (L0=COOH), in the presence of an activating agent such as N,N'-dicyclohexylcarbodiimide or N-(3-dimethylaminopropyl)-N'-ethylcarbodiimide hydrochloride, with the optional addition of 1-hydroxybenzotriazole. Other suitable coupling agents may be utilized such as O-(7-azabenzotriazol-1-yl)-N,N,N',N'-tetramethyluronium hexafluorophosphate, 2-ethoxy-1-ethoxycarbonyl-1,2-dihydroquinoline, carbonyldiimidazole or diethylphosphorylcyanide. Optionally, a base like triethylamine, N,N-diisopropylethylamine or pyridine can be added to perform the coupling. The peptidic coupling is conducted at a temperature between −20° C. and 100° C., in an inert solvent, preferably a dry aprotic solvent like dichloromethane, acetonitrile, N,N-dimethylformamide and chloroform. Alternatively, the carboxylic acid can be activated by conversion into its corresponding acid chloride (by reaction with oxalyl chloride or thionyl chloride) or its corresponding activated ester, such as the N-hydroxysuccinimidyl ester (Org. Process Res. & Dev., 2002, 863) or the benzothiazolyl thioester (J. Antibiotics, 2000, 1071). The generated activated entity can react at a temperature between −20° C. and 100° C. with compound of formula II-1 in an aprotic solvent like dichloromethane, chloroform, acetonitrile, N,N-dimethylformamide and tetrahydrofuran to generate compound of formula I-1. Optionally, a base like triethylamine, N,N-diisopropylethylamine, pyridine, sodium hydroxide, sodium carbonate or potassium carbonate can be added to perform the coupling.

In Scheme 1, coupling of compounds of general formulae IV and V-1, followed by a deprotection step and finally introduction of the A4-G substituent allows the generation of compounds of formula I-1. Alternatively, the protecting group PG1 of compounds of formula V-1 can be removed according to the methods described above and the product of this reaction can then be reacted with one of the compounds of formula III as defined above. Subsequently, these intermediates are converted into compounds of formula I-1 following the methods described above for the synthesis of compounds of formula VI-1.

Scheme 2

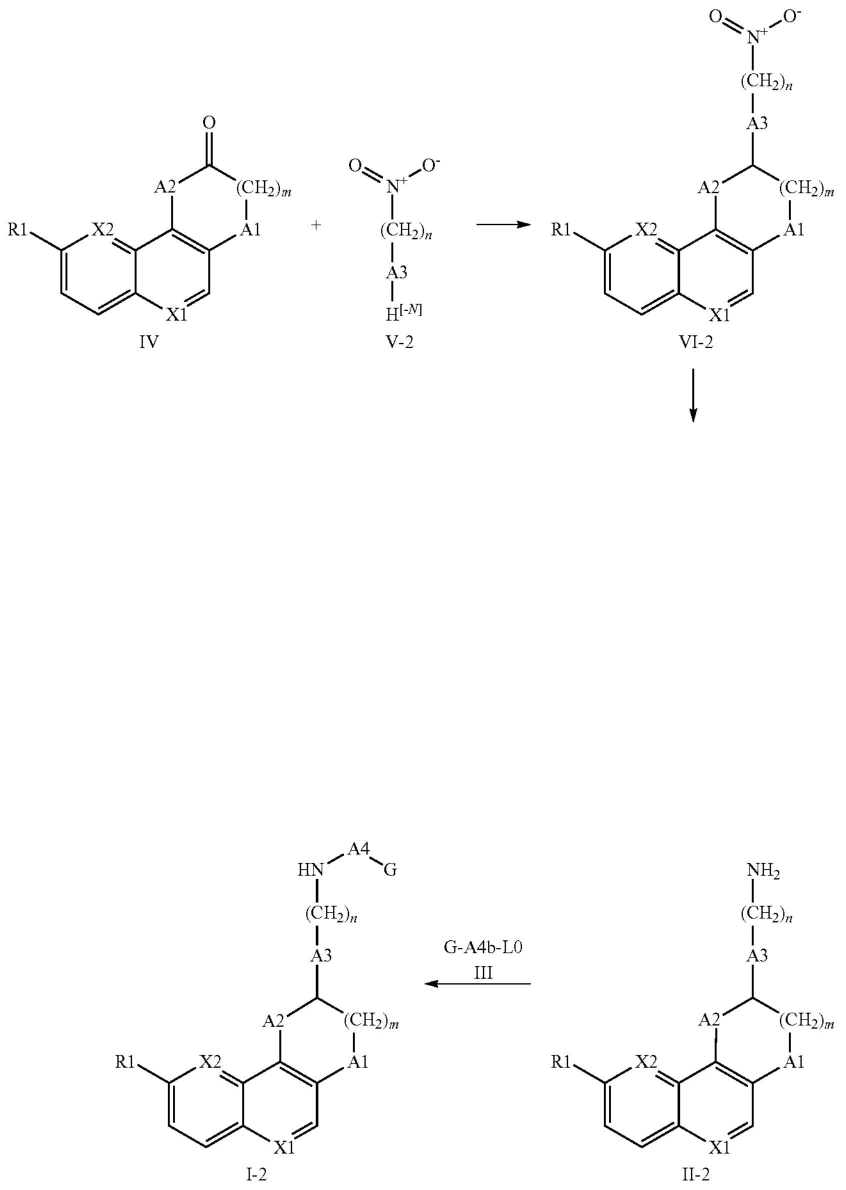

In Scheme 2, all the symbols have the same meaning as in formula I or in Scheme 1.

Reduction of nitro compounds of formula VI-2 to generate amino compounds of formula II-2 is performed using standard methods. Typical reducing agents which can be used for such reaction are an alkali metal hydride such as lithium aluminium hydride or sodium borohydride in presence of cobalt(II) chloride or nickel(II) chloride, or a metal such as iron or zinc in acidic medium such as hydrochloric acid or acetic acid. Alternatively, the nitro group can be reduced to the amine by hydrogenation over a noble metal catalyst such as palladium on activated carbon, Raney nickel or platinum oxide. The catalytic hydrogenation reaction can be carried out in a solvent such as ethanol, methanol or ethyl acetate at ambient temperature. In addition further reagents such as aluminium amalgam or ferrous sulphate may also be used for the nitro group reduction.

In Scheme 2, for all the other steps the methods described above with Scheme 1 can be followed for the preparation of compounds of formula I-2.

Alternatively and as in the case of Scheme 1, the nitro group of compounds of formula V-2 can be reduced according to the methods described above and the product of this reaction can then be reacted with one of the compounds of formula III as defined above. Subsequently, these intermediates are converted into compounds of formula I-2 following the methods described above for the synthesis of compounds of formula VI-2.

The compounds of formula I wherein A1 represents O and A2 is $-CH_2-$ can be obtained as summarized in Scheme 3 hereafter.

Scheme 3

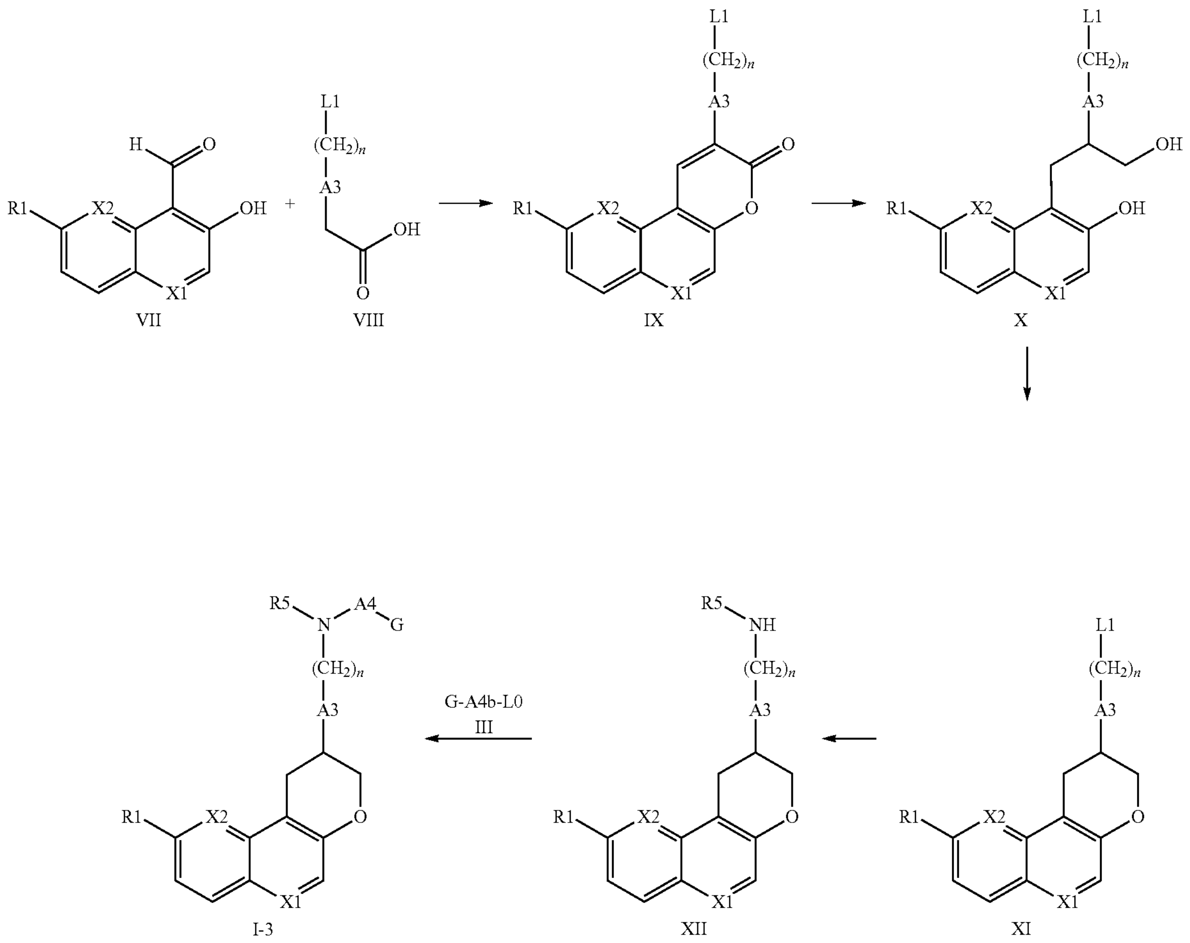

In Scheme 3, all the symbols are as defined above.

Coupling of compounds of general formulae VII and VIII allows the generation of compounds of formula IX. The reaction takes place in presence of a coupling agent such as O-(7-azabenzotriazol-1-yl)-N,N,N',N'-tetramethyluronium hexafluorophosphate and a base like triethylamine, N,N-diisopropylethylamine or 1,8-diazabicyclo[5,4,0]undec-7-ene. The coupling is conducted at a temperature between −20° C. and 100° C., in an inert solvent, preferably a dry aprotic solvent like dichloromethane, acetonitrile or N,N-dimethylformamide.

Esters of formula IX are further reduced to generate compounds of formula X. Reduction is performed with a reducing agent like boron or aluminium hydride reducing agent such as lithium aluminium hydride, lithium borohydride, sodium borohydride in a solvent such as tetrahydrofuran between −20° C. and 80° C. Alternatively, the ester function is hydrolyzed into its corresponding acid using an alkali hydroxide such as sodium hydroxide, potassium hydroxide or lithium hydroxide in water or in a mixture of water with polar protic or aprotic organic solvents such as dioxane, tetrahydrofuran or methanol between −10° C. and 80° C. The resulting carboxylic acid is further reduced into the corresponding alcohol using a borane derivative such as borane-tetrahydrofuran complex in a solvent such as tetrahydrofuran between −10° C. and 80° C.

Compounds of formula XI can be obtained from compounds of formula X via a Mitsunobu coupling (as reviewed by O. Mitsunobu, Synthesis, 1981, 1). The reaction is for example performed in the presence of diethyl or diisopropyl azodicarboxylate and triphenylphosphine, in a wide range of solvents such as N,N-dimethylformamide, tetrahydrofuran, 1,2-dimethoxyethane or dichloromethane and within a wide range of temperatures (between −20° C. and 60° C.). The reaction might also be performed using polymer-supported triphenylphosphine.

In Scheme 3, for all the other steps the methods described above for Schemes 1 and 2 can be followed for the preparation of compounds of formula I-3.

Alternatively and as in the case of Schemes 1 and 2, the protecting group PG1 or the nitro group of compounds of formula VIII can be removed or reduced, respectively, according to the methods described above and the product of this reaction can then be reacted with one of the compounds of formula III as defined above. Subsequently, these intermediates are converted into compounds of formula I-3 following the methods described above for the synthesis of compounds of formulae IX, X and XI.

The compounds of formula I wherein A1 represents —O—, —S— or —N—R3 and A2 is —O— or —N—R4 can be obtained as summarized in Scheme 4 hereafter.

Scheme 4

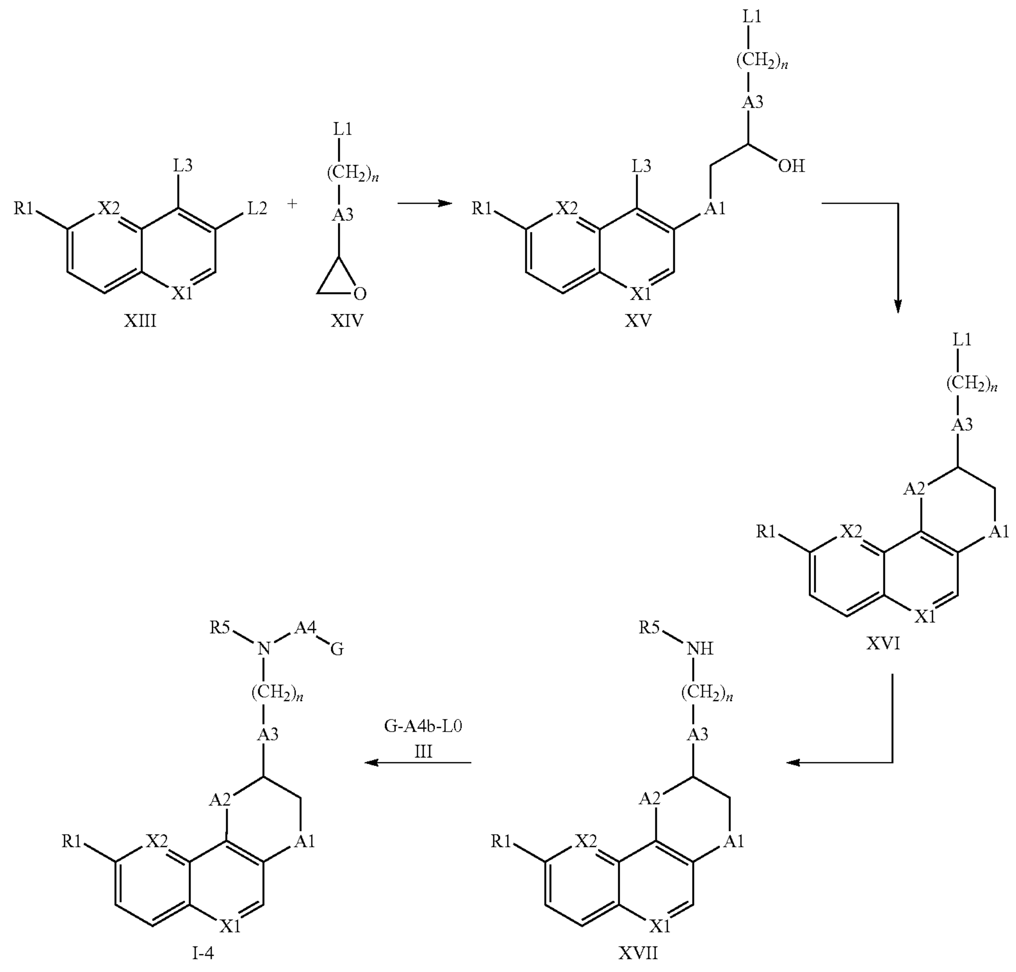

In Scheme 4, X1, X2, R1, R5, A1, A3, A4, G and n are as in formula I,

L1 is as defined above,

A2 is —O— or —N—R4,

L2 is —OH, —SH or —NHR3,

L3 is a halogen atom or —N(R4)PG2 wherein PG2 is an amino protecting group (such as allyloxycarbonyl, benzyloxycarbonyl, 9-fluorenylmethylcarbonyl, tert-butoxycarbonyl or benzyl).

The reaction between compounds of formula XIII and epoxides of formula XIV to generate compounds of formula XV is conducted in the absence or in the presence of a base such as potassium carbonate, ammonium chloride, triethylamine, N,N-diisopropylethylamine, or alternatively in the absence or in the presence of a Lewis acid such as stannic chloride or boron trifluoride, in a wide range of solvents such as N,N-dimethylformamide, carbon tetrachloride, dichloromethane, ethanol and within a wide range of temperatures (between 0° C. and 120° C.).

Compounds of formula XVI wherein A2 is —O— can be obtained from compounds of formula XV wherein L3 is a halogen atom. The intramolecular reaction is performed in presence of a base such as sodium hydride in a solvent such as dichloromethane, tetrahydrofuran or N,N-dimethylformamide at a temperature ranging between −20° C. and 80° C.

Compounds of formula XVI wherein A2 is —N—R4 can be obtained from compounds of formula XV wherein L3 is —N(R4)PG2. The alcohol is first transformed into its corresponding ketone through oxidation under Swern (see D. Swern et al., J. Org. Chem., 1978, 43, 2480-2482), Dess Martin (see D. B. Dess and J. C. Martin, J. Org. Chem., 1983, 48, 4155) or Jones (see E. R. H. Jones et al., J. Chem. Soc., 1953, 457 and 2548 and 3019) conditions respectively. Further methods are described in Comprehensive Organic Transformations. A guide to functionnal Group Preparations; 2$^{nd}$ Edition, R. C. Larock, Wiley-VC; New York, Chichester, Weinheim, Brisbane, Singapore, Toronto, 1999. Section aldehydes and ketones, p. 1235-1236 and 1238-1246. This oxidation step is followed by the removal of the protecting group PG2 following standard conditions previously described for the preparation of compounds of formula II-1. At that stage intramolecular reductive amination is performed following procedures previously described for the preparation of compounds of formula VI-1.

Alternatively, compounds of formula XVI wherein A2 is —N—R4 can be obtained from compounds of formula XV wherein L3 is —N(R4)PG2 by first transforming the alcohol into a leaving group like mesylate, tosylate or triflate following standard conditions previously described for the preparation of compounds of formula I-1. At that stage, the protecting group PG2 is first removed following standard conditions previously described for the preparation of compounds of formula II-1 and further cyclisation is performed in presence of a base such as potassium carbonate or sodium hydride in a solvent such as dichloromethane or N,N-dimethylformamide at a temperature ranging between −20° C. and 80° C.

In Scheme 4, for all the other steps the methods described above with Schemes 1 and 2 can be followed for the preparation of compounds of formula I-4.

The compounds of formula I wherein A1 represents —O—, —S— or —N—R3 and A2 is —$CH_2$— or —N—R4 can be obtained as summarized in Scheme 5 hereafter.

Scheme 5

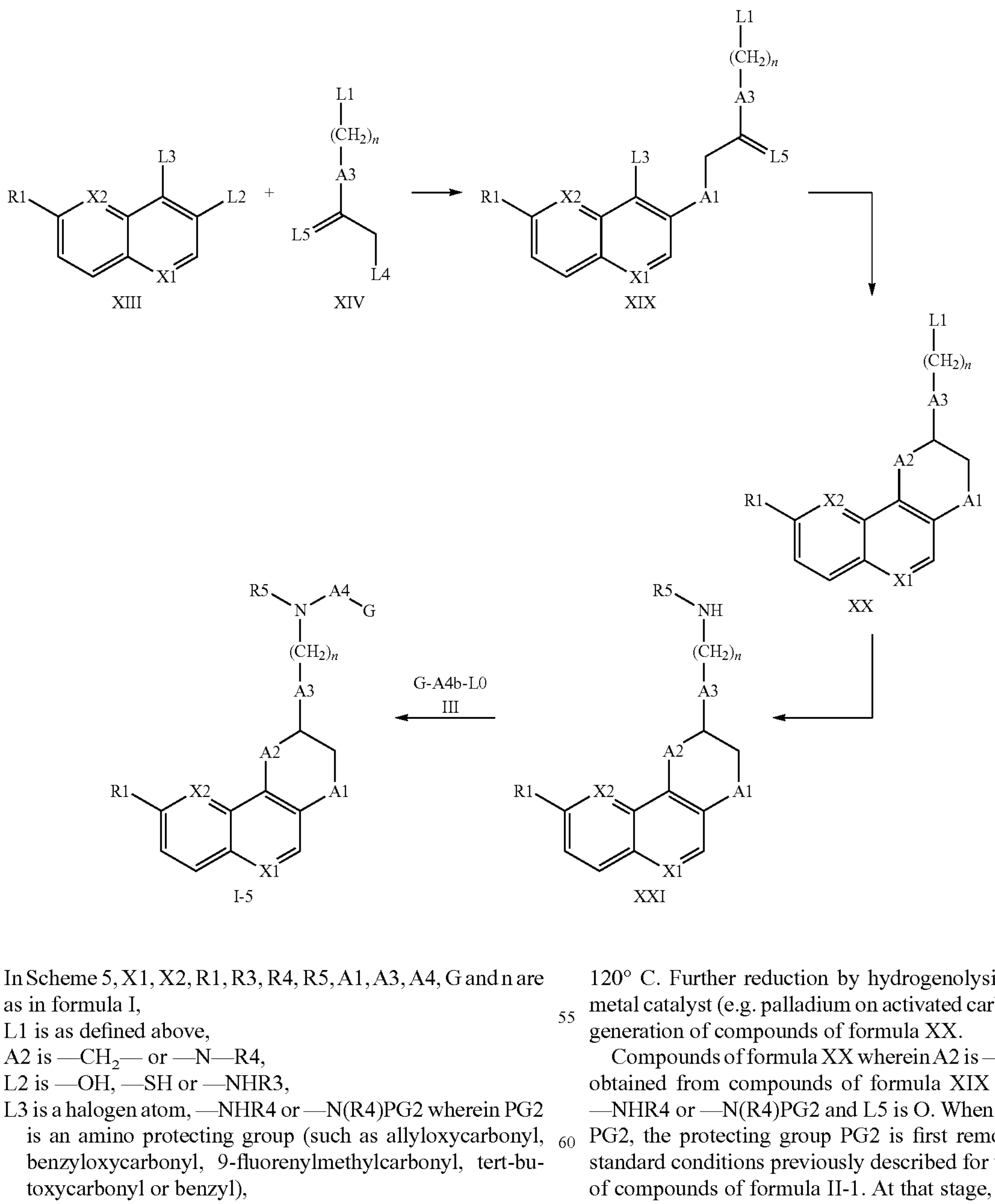

In Scheme 5, X1, X2, R1, R3, R4, R5, A1, A3, A4, G and n are as in formula I,

L1 is as defined above,

A2 is —$CH_2$— or —N—R4,

L2 is —OH, —SH or —NHR3,

L3 is a halogen atom, —NHR4 or —N(R4)PG2 wherein PG2 is an amino protecting group (such as allyloxycarbonyl, benzyloxycarbonyl, 9-fluorenylmethylcarbonyl, tert-butoxycarbonyl or benzyl), L4 is a halogen atom, L5 is $CH_2$ or O.

The reaction between compounds of formula XIII and halogenides of formula XVIII to generate compounds of formula XIX is conducted in presence of a base such as potassium carbonate, cesium carbonate, triethylamine or sodium hydride in a dry aprotic solvent such as dichloromethane or N,N-dimethylformamide at a temperature ranging between −20° C. and 80° C.

Compounds of formula XX wherein A2 is —$CH_2$— can be obtained from compounds of formula XIX wherein L3 is a halogen atom and L5 is $CH_2$. The intramolecular coupling reaction is performed in presence of a palladium catalyst such as palladium(II)acetate and a base such as triethylamine in a solvent such as N,N-dimethylformamide, dichloromethane, tetrahydrofuran at a temperature ranging between 20° C. and 120° C. Further reduction by hydrogenolysis over a noble metal catalyst (e.g. palladium on activated carbon) allows the generation of compounds of formula XX.

Compounds of formula XX wherein A2 is —N—R4 can be obtained from compounds of formula XIX wherein L3 is —NHR4 or —N(R4)PG2 and L5 is O. When L3 is —N(R4)PG2, the protecting group PG2 is first removed following standard conditions previously described for the preparation of compounds of formula II-1. At that stage, intramolecular reductive amination is performed following procedures previously described for the preparation of compounds of formula VI-1.

Alternatively, compounds of formula XX wherein A2 is —N—R4 can be obtained from compounds of formula XIX wherein L3 is —NHR4 or —N(R4)PG2 and L5 is O by first reducing the ketone to the corresponding alcohol using a boron or aluminium hydride reducing agent such as sodium borohydride, lithium borohydride or lithium aluminium hydride in a solvent such as tetrahydrofuran or diethyl ether between −20° C. and 40° C. Activation of the generated hydroxyl group, followed by removal of the protecting group PG2 and cyclisation, respectively (as previously described for the preparation of compounds of formula XVI in Scheme 4) allows the generation of the expected compounds of formula XX.

In Scheme 5, for all the other steps the methods described above with Schemes 1 and 2 can be followed for the preparation of compounds of formula I-5.

The compounds of formula I wherein A1 is —O— and A2 is —$CH_2$— can be obtained as summarized in Scheme 6 hereafter.

generation of compounds of formula XXIII. The reaction takes place in presence of a catalytic amount of a chiral secondary amine such as L-proline at a temperature between −20° C. and 40° C. in an aprotic solvent like acetone, N,N-dimethylformamide or dimethyl sulfoxide (see Z. G. Hajos and D. P. Parrish, J. Org. Chem., 1974, 39, 1615; B. List, R. A. Lerner and C. F. Barbas, J. Am. Chem. Soc., 2000, 122, 2395). Acetylation of compounds of formula XXIII to generate compounds of formula XXIV is performed in presence of acetic anhydride and an organic base such as pyridine or triethylamine with or without solvent between 20° C. and 120° C.

Compounds of formula XXIV are further submitted to an hydrogenolysis over a noble metal catalyst (e.g. palladium or palladium hydroxide on activated carbon), followed by a reduction step (following standard conditions previously described for the preparation of compounds of formula X in Scheme 3) to generate compounds of formula X.

Scheme 6

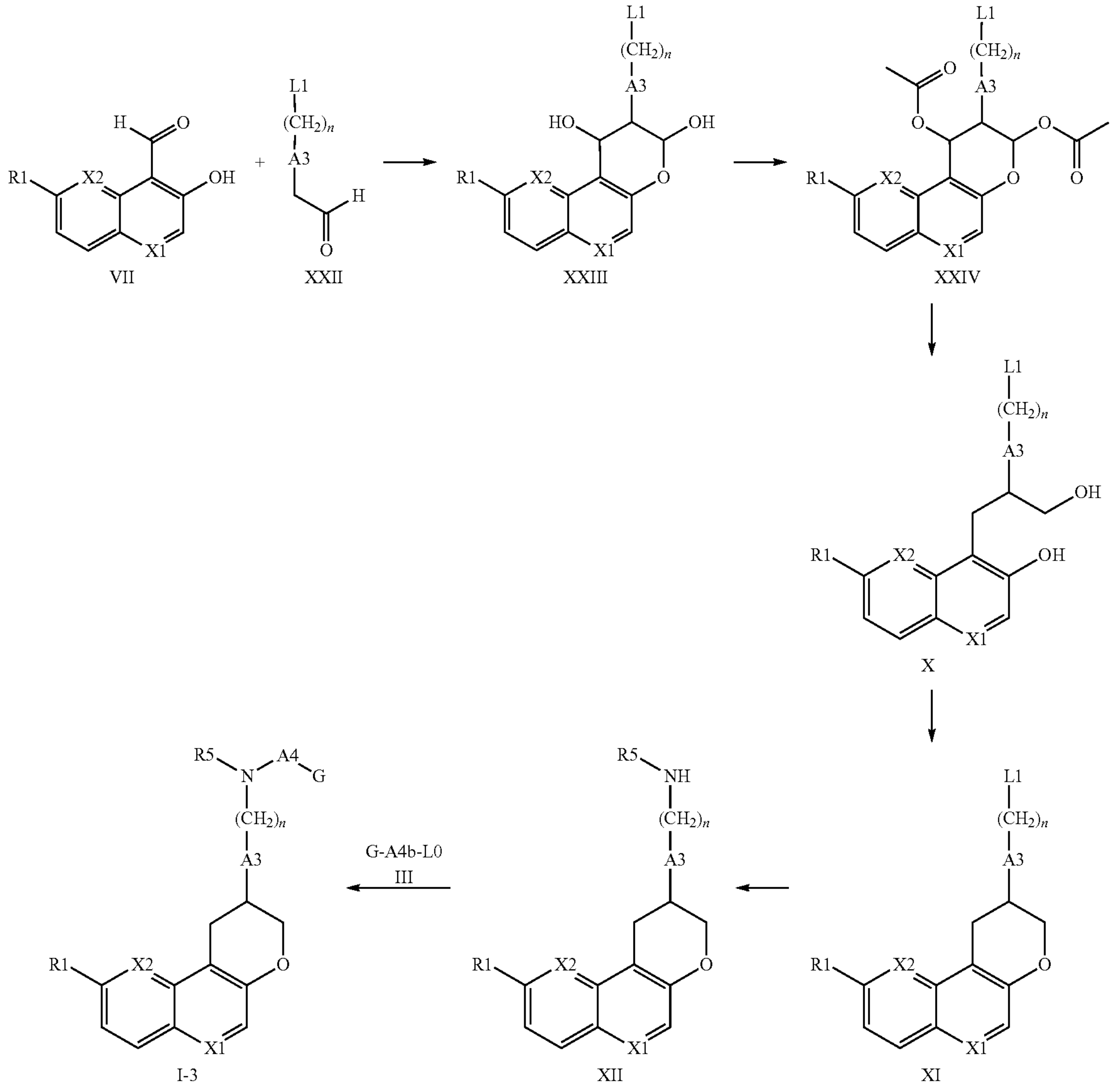

In Scheme 6, all the symbols are as defined above.

Aldol reaction between the electrophilic compounds of formula VII and compounds of formula XXII allows the In Scheme 6, for all the other steps the methods described above with Schemes 1 to 3 can be followed for the preparation of compounds of formula I-3.

The compounds of formula I wherein A1 is —N—R3 and A2 is —O— can be obtained as summarized in Scheme 7 hereafter.

Scheme 7

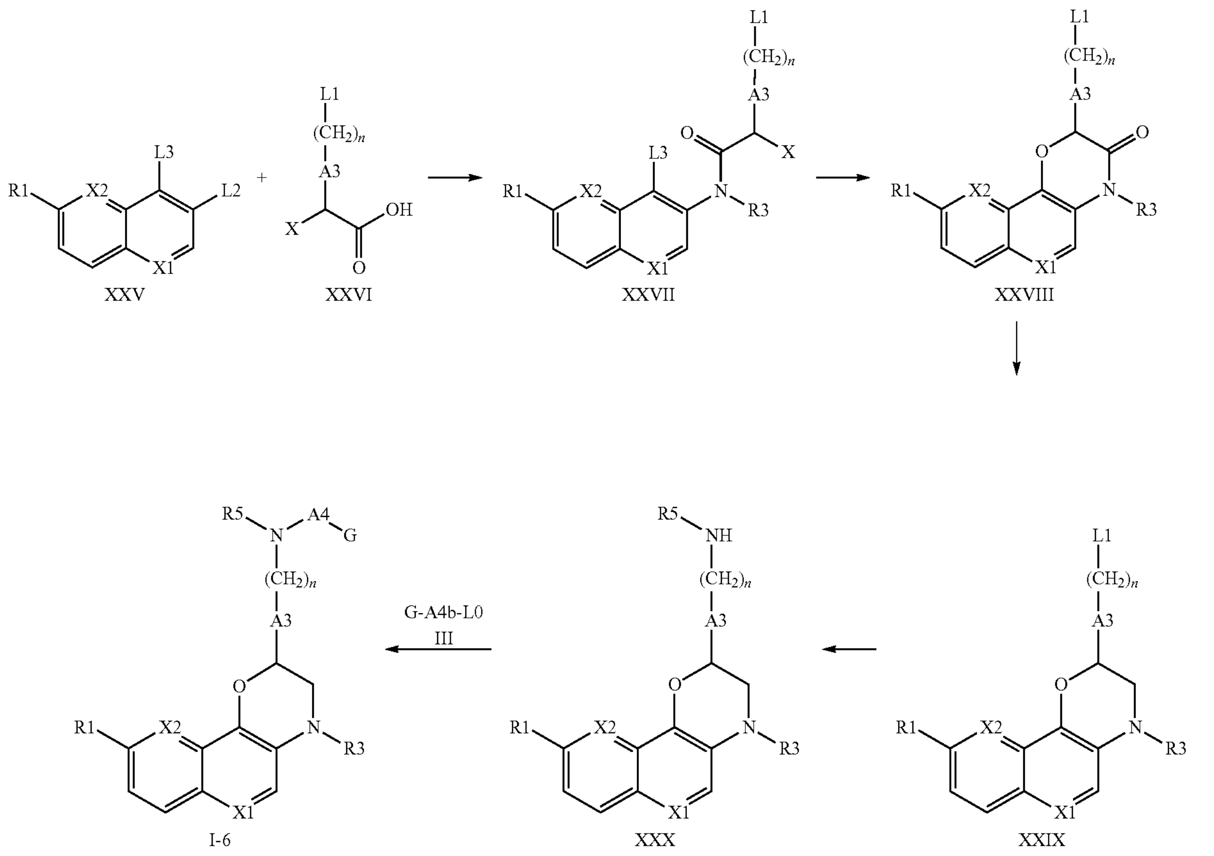

In Scheme 7, X1, X2, A3, R1, R3, R5, A4, G and n are as in formula I,

L1 is as defined above,

L2 is —NHR3 or —N(R3)PG2 wherein PG2 is an amino protecting group (such as allyloxycarbonyl, benzyloxycarbonyl, 9-fluorenylmethylcarbonyl, tert-butoxycarbonyl or benzyl), L3 is —OH or —OPG3 wherein PG3 is a phenol protecting group (such as benzyl, allyl, tetrahydropyranyl, tert-butyl dimethylsilyl).

X is a halogen atom,

Compounds of formula XXVII can be obtained from compounds of formulae XXV and XXVI. When L2 is —N(R3)PG2, the protecting group PG2 is first removed following standard conditions previously described for the preparation of compounds of formula II-1. At that stage, peptidic coupling is performed following the methods described above for the synthesis of compounds of formula I-1.

Compounds of formula XXVIII can be obtained from compounds of formula XXVII. When L3 is —OPG3, the protecting group PG3 is first removed following standard conditions. For example the benzyl group is removed by hydrogenolysis over a noble metal catalyst (e.g. palladium or palladium hydroxide on activated carbon); the allyl group is removed in presence of a palladium salt such as palladium acetate or tetrakis(triphenylphosphine)palladium(0) and an allyl cation scavenger such as morpholine, pyrrolidine, dimedone or tributylstannane between 0° C. and 70° C. in a solvent such as tetrahydrofuran; the tetrahydropyranyl group is removed in presence of aqueous oxalic acid between 50° C. and 90° C. in a solvent such as methanol; the tert-butyl dimethylsilyl group is removed either using fluoride anion sources such as tetra-n-butylammonium fluoride in a solvent such as tetrahydrofuran or N,N-dimethylformamide or in hydrofluoric acid in acetonitrile between 0° C. and 40° C. Further general methods to remove phenol protecting groups have been described in *Protective Groups in Organic Synthesis*, 3rd Edition, by T. W. Greene and P. G. M. Wuts, published by John Wiley & Sons, 1999.

Further intramolecular substitution is performed at a temperature between −20° C. and 100° C. in a dry aprotic solvent like dichloromethane, acetonitrile, N,N-dimethylformamide, dimethyl sulfoxide or tetrahydrofuran in the presence of an inorganic base such as potassium carbonate, cesium carbonate or sodium hydride, or an organic base such as triethylamine or N,N-diisopropylethylamine.

The generated amides of formula XXVIII are reduced with diborane, borane-tetrahydrofuran or borane dimethyl sulfide complexes in a solvent such as tetrahydrofuran between −10° C. and 60° C. The reaction is further treated with diluted hydrochloric acid between 0° C. and 50° C. to generate compounds of formula XXIX.

In Scheme 7, for all the other steps the methods described above with Schemes 1 and 2 can be followed for the preparation of compounds of formula I-6.

The compounds of formula I wherein A1 represents —N—R3 and A2 is —$CH_2$— can also be obtained as summarized in Scheme 8 hereafter.
Scheme 8
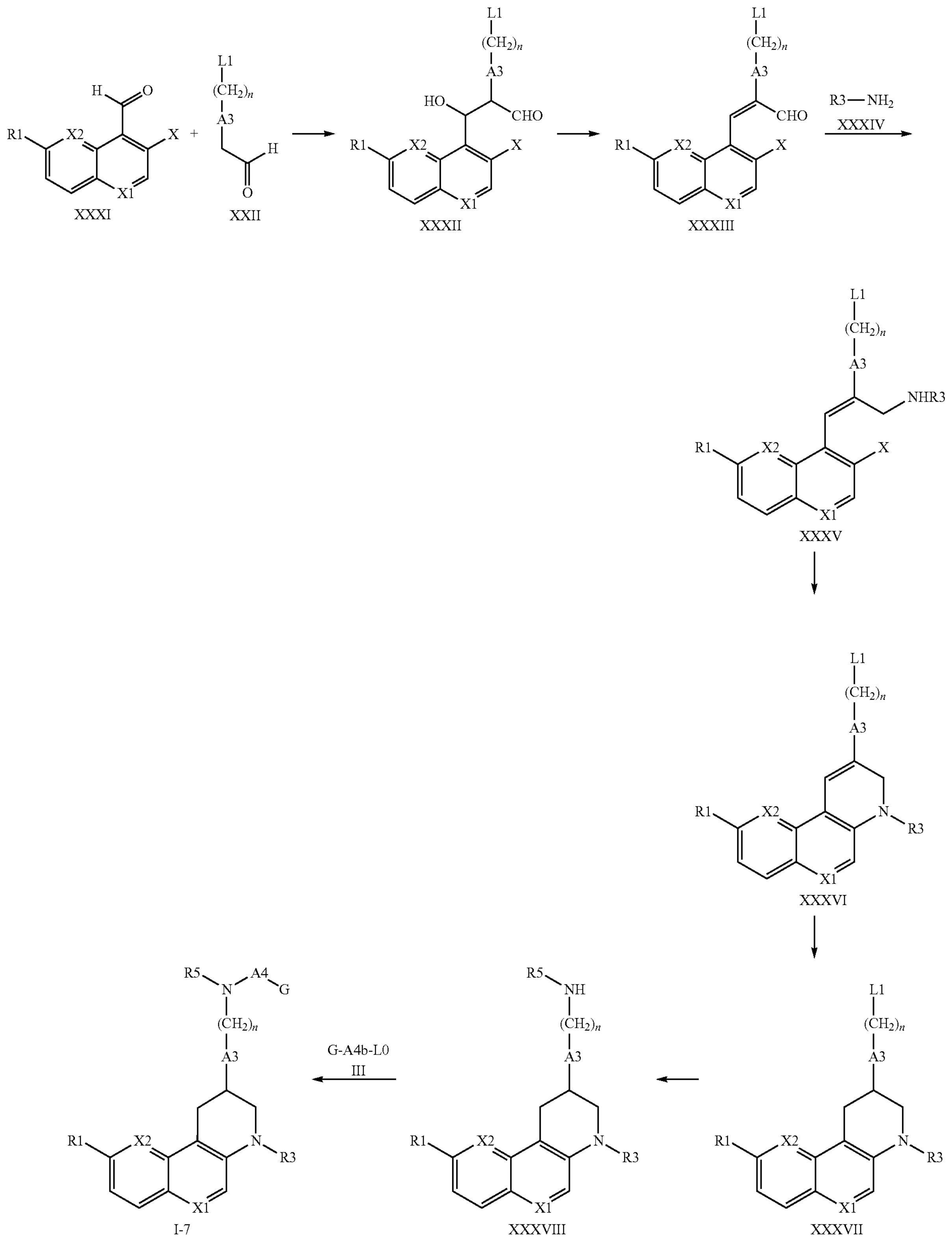

In Scheme 8, X is a halogen atom and all the other symbols are as defined above.

Compounds of formula XXXII can be obtained from compounds of formulae XXXI and XXII following the aldol reaction conditions previously described for the preparation of compounds of formula XXIII. Further acetylation following reaction conditions previously described for the preparation of compounds of formula XXIV led to the generation of the elimination products of formula XXXIII.

At that stage reductive amination between aldehydes of formula XXXIII and amines of formula XXXIV is performed following the methods described above for the synthesis of compounds of formula VI-1.

Compounds of formula XXXVI are then generated by intramolecular cyclisation in presence of an inorganic base such as potassium or cesium carbonate, sodium hydride or sodium hydroxide in a solvent such as tetrahydrofuran, N,N-dimethylformamide or acetone at a temperature ranging from −20° C. and 100° C.

The unsaturated derivatives of formula XXXVI dissolved in a solvent such as methanol, ethyl acetate of tetrahydrofuran are hydrogenated over a noble metal catalyst such as palladium or palladium hydroxide on activated carbon, platinum oxide or Raney nickel to generate compounds of formula XXXVII. Alternatively the reduction can be performed by catalytic transfer hydrogenation using palladium on activated carbon and ammonium formate as hydrogen source.

In Scheme 8, for all the other steps the methods described above with Schemes 1 and 2 can be followed for the preparation of compounds of formula I-7.

Unless otherwise stated the required starting compounds of formula IV, VII, XIII, XXV and XXXI are prepared following or adapting procedures described in the scientific literature, such as J. Org. Chem., 1953, 18(5), p. 552; J. Med. Chem., 1988, 31(3), p. 688; Synthesis, 2004, 1, p. 121; Organic Synthesis Coll., 1960, vol. 40, p. 54; PCT Pub. No. WO93/20055, WO2005/004808.

Unless otherwise stated the required starting derivatives of formula V, VIII and XXII are commercially available or are prepared following or adapting synthetic procedures described in the scientific literature, such as J. Med. Chem., 2007, 50(15), p. 3561; PCT Pub. No. WO2009/012647, WO2008/003690, WO2005/077932, US2005/0101644, Unless otherwise stated compounds of formula III-1, III-2 and III-3 are commercially available or may be obtained by procedures described in the patent literature, such as PCT Pub. No. WO2007/093507, WO2007/052843, WO2006/105289, WO2006/038734, WO2006/021448, WO2004/058144, WO2004/002992, WO02/34754.

When an optically active form of a compound of the invention is required, it may be obtained by carrying out one of the above procedures using a pure enantiomer or diastereomer as a starting material, or by resolution of a mixture of the enantiomers or diastereomers of the final product or intermediate using a standard procedure. The resolution of enantiomers may be achieved by chromatography on a chiral stationary phase, such as REGIS PIRKLE COVALENT (R—R) WHELK-02, 10 μm, 100 Å, 250×21.1 mm column. Alternatively, resolution of stereoisomers may be obtained by preparation and selective crystallization of a diastereomeric salt of a chiral intermediate or chiral product with a chiral acid, such as camphorsulfonic acid. Alternatively a method of stereoselective synthesis may be employed, for example by using a chiral variant of a protecting group, a chiral catalyst or a chiral reagent where appropriate in the reaction sequence.

Enzymatic techniques may also be used for the preparation of optically active compounds and/or intermediates.

Further aspects of the invention include

- pharmaceutical compositions comprising a compound of formula (I) or a pharmaceutically acceptable salt, a hydrate or solvate thereof and a pharmaceutically acceptable carrier;
- the compounds of formula (I) or a pharmaceutically acceptable salt, a hydrate or solvate thereof for use as a medicament, in particular a medicament for the treatment of bacterial infections; and
- the use of a compound of formula (I) or a pharmaceutically acceptable salt, a hydrate or solvate thereof for the preparation of medicaments for the treatment of infectious diseases caused by bacteria.

All listed compounds except examples 25 and 56 shown in Table 1 below are particularly advantageous for the treatment of infections by *Staphylococcus aureus* and/or *Staphylococcus epidermidis* and exhibit a MIC for said strains of generally ≤8 mg/L.

The compounds of number 1-19; 50; 54-55; 57; 59; 61-65; 67-75; 77-78 shown in Table 1 below are particularly advantageous for the treatment of infections by *Staphylococcus aureus* and/or *Staphylococcus epidermidis* and/or *Streptococcus pneumoniae* and exhibit a MIC for said strains of generally ≤8 mg/L.

The compounds of number 1-6; 11; 17; 18; 27; 28; 35; 36; 39; 45; 46; 54; 64 shown in Table 1 below are particularly advantageous for the treatment of infections by *Staphylococcus aureus* and/or *Staphylococcus epidermidis* and/or *Streptococcus pneumoniae* and/or *Escherichia coli* and exhibit a MIC for said strains of generally ≤8 mg/L.

In general, compounds of formula (I) are administered either individually, or optionally also in combination with another desired therapeutic agent, using the known and acceptable methods. Such therapeutically useful agents may be administered, for example, by one of the following routes: orally, for example in the form of dragees, coated tablets, pills, semi-solid substances, soft or hard capsules, solutions, emulsions or suspensions; parenterally, for example in the form of an injectable solution; rectally in the form of suppositories; by inhalation, for example in the form of a powder formulation or a spray; transdermally or intranasally.

For the preparation of such tablets, pills, semi-solid substances, coated tablets, dragees and hard gelatine capsules, the therapeutically usable product may be mixed with pharmacologically inert, inorganic or organic pharmaceutical carrier substances, for example with lactose, sucrose, glucose, gelatine, malt, silica gel, starch or derivatives thereof, talcum, stearic acid or salts thereof, skimmed milk powder, and the like. For the preparation of soft capsules, pharmaceutical carrier substances such as, for example, vegetable oils, petroleum, animal or synthetic oils, wax, fat and polyols may be used.

For the preparation of liquid solutions and syrups, pharmaceutical carrier substances such as, for example, water, alcohols, aqueous saline solution, aqueous dextrose solution, polyols, glycerol, vegetable oils, petroleum and animal or synthetic oils may be used.

For suppositories, pharmaceutical carrier substances such as, for example, vegetable oils, petroleum, animal or synthetic oils, wax, fat and polyols may be used.

For aerosol formulations, compressed gases that are suitable for this purpose, such as, for example, oxygen, nitrogen and carbon dioxide may be used. The pharmaceutically acceptable agents may also comprise additives for preserving and stabilising, emulsifiers, sweeteners, flavourings, salts for altering the osmotic pressure, buffers, encapsulation additives and antioxidants.

Combinations with other therapeutic agents which are also encompassed by the present invention may comprise one, two or more other antimicrobial and anti-fungal active ingredients.

For the prevention and/or treatment of bacterial infections, the dose of the biologically active compound according to the invention may vary within wide limits and may be adjusted to individual requirements. Generally, a dose of 10 mg to 4000 mg per day is suitable, a preferred dose being from 50 to 3 000 mg per day. In suitable cases, the dose may also be below or above the stated values. The daily dose may be administered as a single dose or in multiple doses. A typical individual dose contains approximately 50 mg, 100 mg, 250 mg, 500 mg, 1 g or 2 g of the active ingredient.

Examples

Particular embodiments of the invention are described in the following Examples, which serve to illustrate the invention in more detail:

All reagents and solvents are generally used as received from the commercial supplier; reactions are routinely performed with anhydrous solvents in well-dried glassware under an argon or nitrogen atmosphere;

evaporations are carried out by rotary evaporation under reduced pressure and work-up procedures are carried out after removal of residual solids by filtration;

all temperatures are given in ° C.; unless otherwise noted, operations are carried out at room temperature, that is typically in the range 18-25° C.;

column chromatography (by the flash procedure) is used to purify compounds and is performed using Merck silica gel 60 (70-230 mesh ASTM) unless otherwise stated; in general, the course of reactions is followed by TLC, HPLC, or LC/MS and reaction times are given for illustration only; yields are given for illustration only and are not necessarily the maximum attainable;

the structure of the final products of the invention is generally confirmed by NMR and mass spectral techniques. Proton NMR spectra are recorded on a Brucker 400 MHz spectrometer. Chemical shifts (δ) are reported in ppm relative to $Me_4Si$ as internal standard, and J values are in Hertz (Hz). Each peak is denoted as a broad singlet (br), singlet (s), doublet (d), doublet of doublets (dd), triplet of doublets (td) or multiplet (m). Mass spectra are generated using a q-T of Ultima (Waters AG) mass spectrometer in the positive ESI mode. The system is equipped with the standard Lockspray interface;

each intermediate is purified to the standard required for the subsequent stage and is characterized in sufficient detail to confirm that the assigned structure is correct; analytical and preparative HPLC on non-chiral phases are performed using RP-C18 based columns;

the following abbreviations may be used:

Acetone-d6: Deuterated acetone
$CDCl_3$: Deuterated chloroform
DMSO-d6: Deuterated dimethyl sulphoxide
ELSD: Evaporative light scattering detection
HPLC: High performance liquid chromatography
J: Coupling constant
LC/MS: Liquid chromatography coupled to mass spectoscopy
MeOH-d4: Deuterated methanol
$Me_4Si$: Tetramethylsilane
MS: Mass spectroscopy
NMR: Nuclear magnetic resonance
TLC: Thin layer chromatography The following Examples refer to the compounds of formula I as indicated in Table 1:

TABLE 1

Exemplified compounds

| Example | 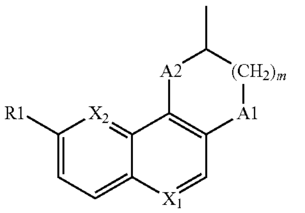 | 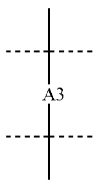 | n | R5 | A4 | G |
|---|---|---|---|---|---|---|
| 1 | 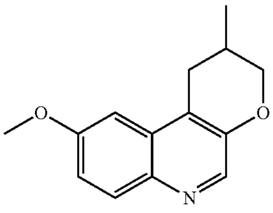 | 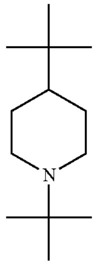 | 0 | H | C=O | 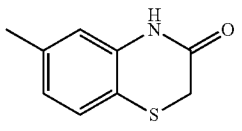 |

TABLE 1-continued
Exemplified compounds
| Example | 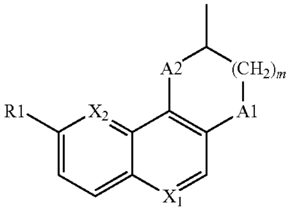 | 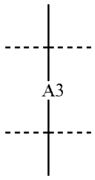 | n | R5 | A4 | G |
|---|---|---|---|---|---|---|
| 2 | 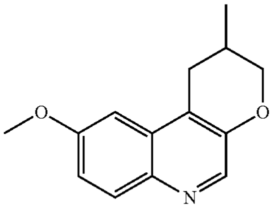 | 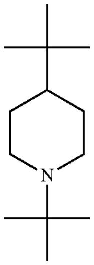 | 0 | H | —$CH_2$— | 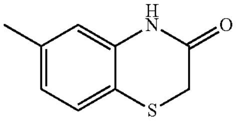 |
| 3 | 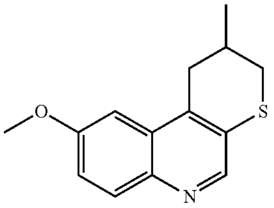 | 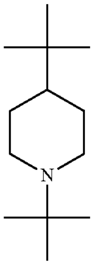 | 0 | H | —$CH_2$— | 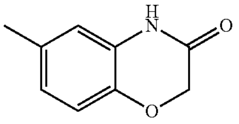 |
| 4 | 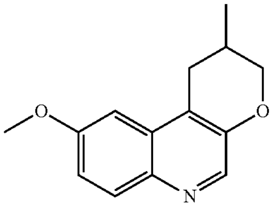 [SMILES: COc1ccc2ncc3c(c2c1)CC(C)CO3] | 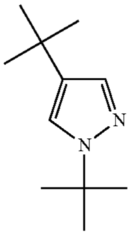 | 0 | H | C═O | 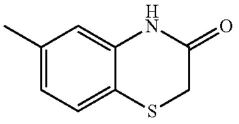 |
| 5 | 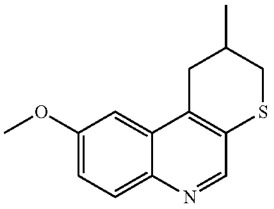 | 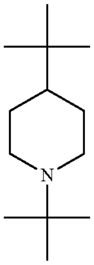 | 0 | H | —$CH_2$— | 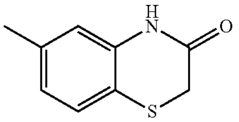 |
| 6 | 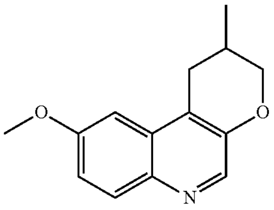 [SMILES: COc1ccc2ncc3c(c2c1)CC(C)CO3] | 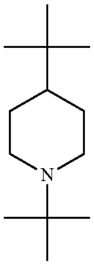 | 0 | H | C═O | 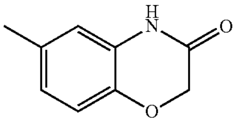 |

TABLE 1-continued
| Exemplified compounds | | | | | | |
|---|---|---|---|---|---|---|
| Example | 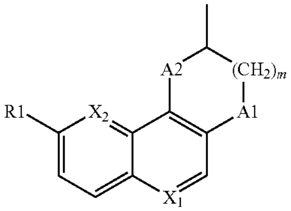 | 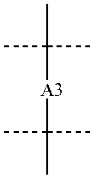 | n | R5 | A4 | G |
| 7 | 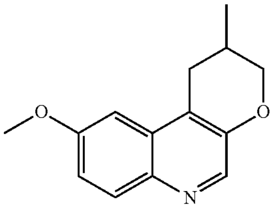 [SMILES: COc1ccc2ncc3c(c2c1)CC(C)CO3] | 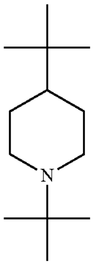 | 0 | H | C═O | 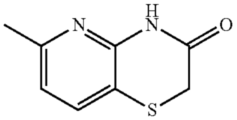 |
| 8 | 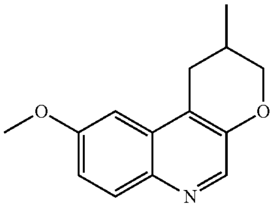 [SMILES: COc1ccc2ncc3c(c2c1)CC(C)CO3] | 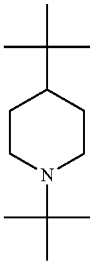 | 0 | H | C═O | 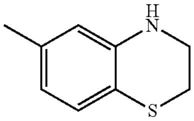 |
| 9 | 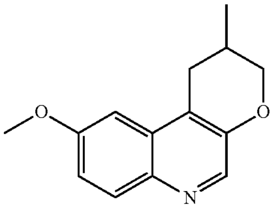 [SMILES: COc1ccc2ncc3c(c2c1)CC(C)CO3] | 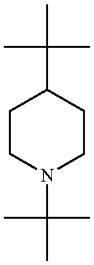 | 0 | H | C═O | 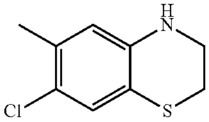 |
| 10 | 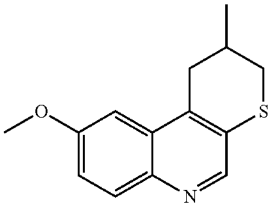 [SMILES: COc1ccc2ncc3c(c2c1)CC(C)CS3] | 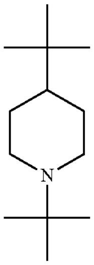 | 0 | H | C═O | 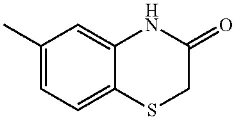 |
| 11 | 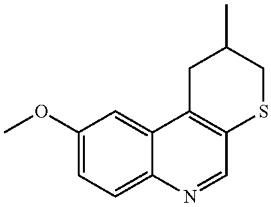 [SMILES: COc1ccc2ncc3c(c2c1)CC(C)CS3] | 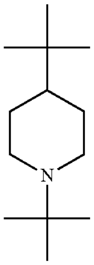 | 0 | H | $-CH_2-$ | 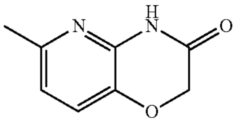 |

TABLE 1-continued
| Exemplified compounds | | | | | | |
|---|---|---|---|---|---|---|
| Example | 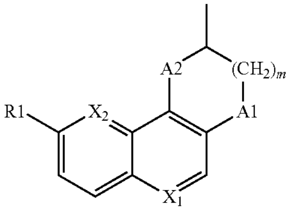 | 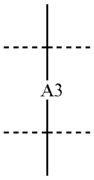 | n | R5 | A4 | G |
| 12 | 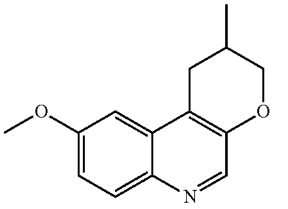 | 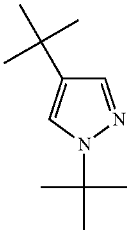 | 0 | H | $—CH_2—$ | 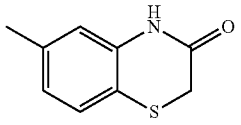 |
| 13 | 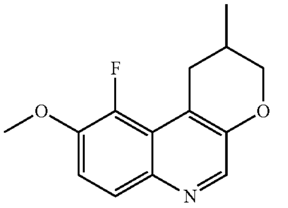 [SMILES: COc1ccc2ncc3c(c2c1F)CC(C)CO3] | 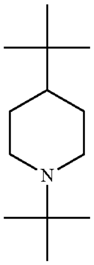 | 0 | H | C═O | 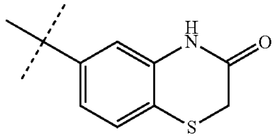 |
| 14 | 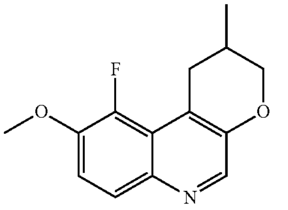 [SMILES: COc1ccc2ncc3c(c2c1F)CC(C)CO3] | 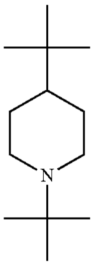 | 0 | H | C═O | 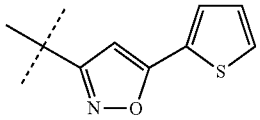 |
| 15 | 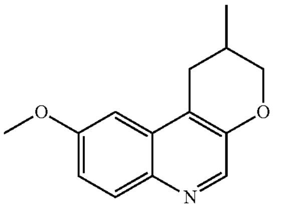 [SMILES: COc1ccc2ncc3c(c2c1)CC(C)CO3] | 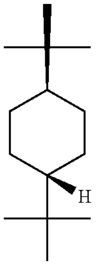 | 0 | H | C═O | 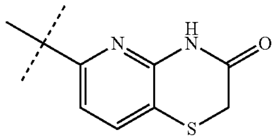 |
| 16 | 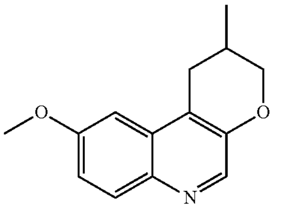 [SMILES: COc1ccc2ncc3c(c2c1)CC(C)CO3] | 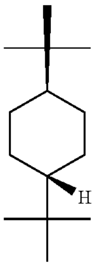 | 0 | H | C═O | 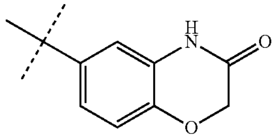 |

TABLE 1-continued
| Exemplified compounds | | | | | | |
|---|---|---|---|---|---|---|
| Example | 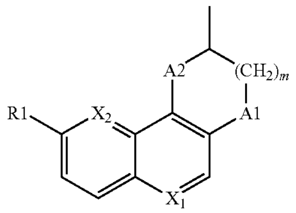 | 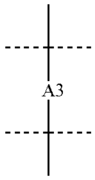 | n | R5 | A4 | G |
| 17 | 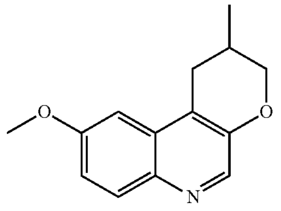 | 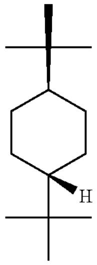 | 0 | H | —$CH_2$— | 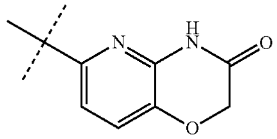 |
| 18 | 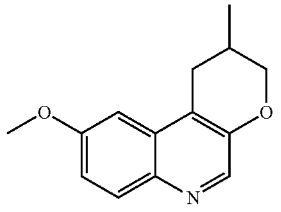 | 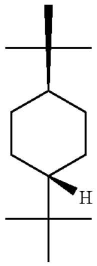 | 0 | H | —$CH_2$— | 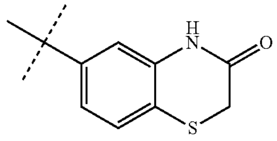 |
| 19 | 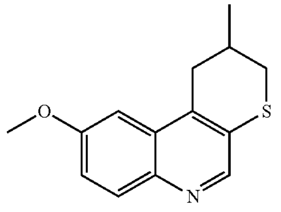 [SMILES: COc1ccc2ncc3c(c2c1)CC(C)CS3] | 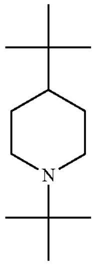 | 0 | H | C═O | 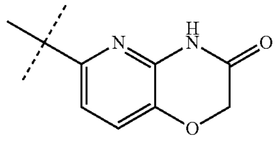 |
| 20 | 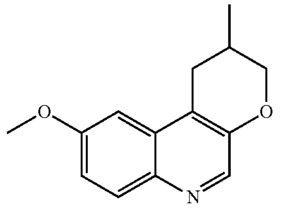 [SMILES: COc1ccc2ncc3c(c2c1)CC(C)CO3] | 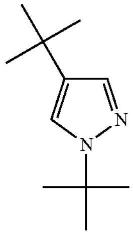 | 0 | H | $C_2H_4$—S | 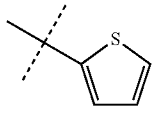 |
| 21 | 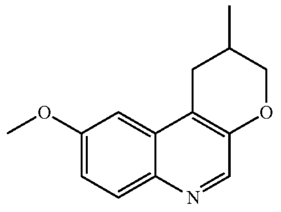 [SMILES: COc1ccc2ncc3c(c2c1)CC(C)CO3] | 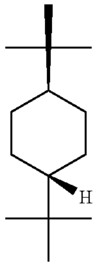 | 0 | H | C═O | 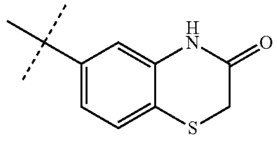 |

TABLE 1-continued
Exemplified compounds
| Example | 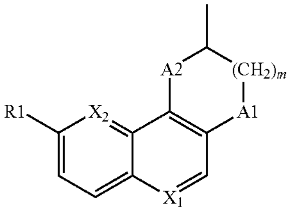 | 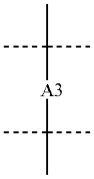 | n | R5 | A4 | G |
|---|---|---|---|---|---|---|
| 22 | 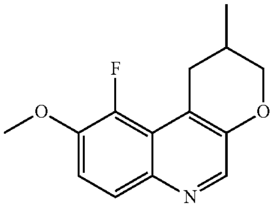 [SMILES: COc1ccc2ncc3c(c2c1F)CC(C)CO3] | 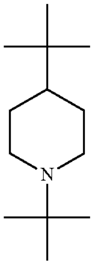 | 0 | H | C=O | 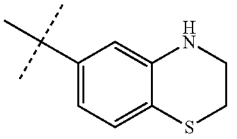 |
| 23 | 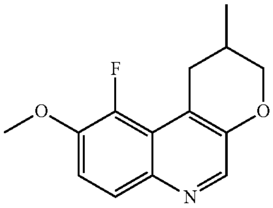 [SMILES: COc1ccc2ncc3c(c2c1F)CC(C)CO3] | 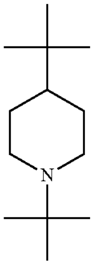 | 0 | H | C=O | 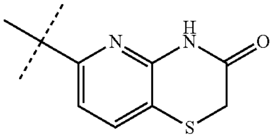 |
| 24 | 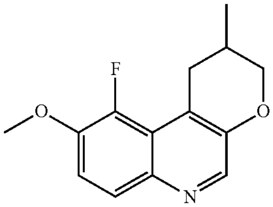 [SMILES: COc1ccc2ncc3c(c2c1F)CC(C)CO3] | 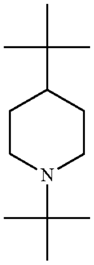 | 0 | H | C=O | 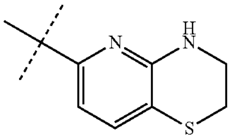 |
| 25 | 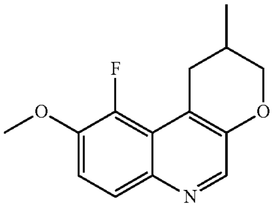 [SMILES: COc1ccc2ncc3c(c2c1F)CC(C)CO3] | 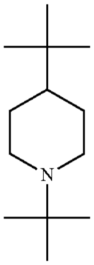 | 0 | H | C=O | 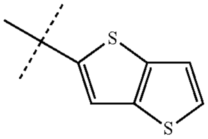 |
| 26 | 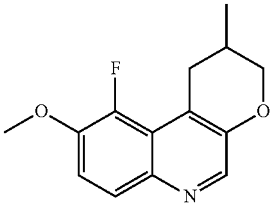 [SMILES: COc1ccc2ncc3c(c2c1F)CC(C)CO3] | 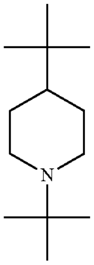 | 0 | H | C=O | 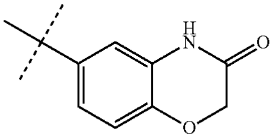 |

TABLE 1-continued
Exemplified compounds
| Example | 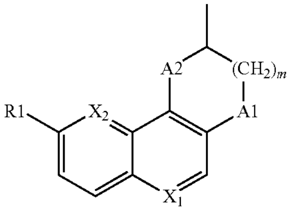 | 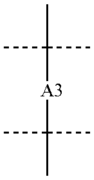 | n | R5 | A4 | G |
|---|---|---|---|---|---|---|
| 27 | 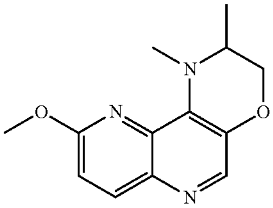 [SMILES: COc1ccc2ncc3c(c2n1)N(C)C(C)CO3] | 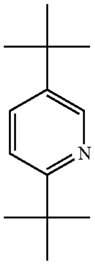 | 0 | H | C═O | 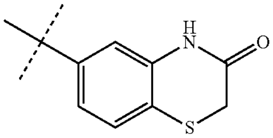 |
| 28 | 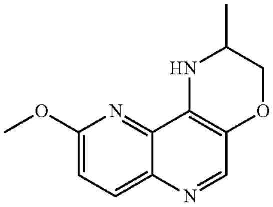 [SMILES: COc1ccc2ncc3c(c2n1)NC(C)CO3] | 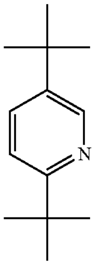 | 0 | H | C═O | 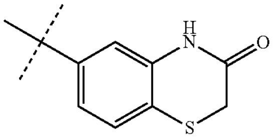 |
| 29 | 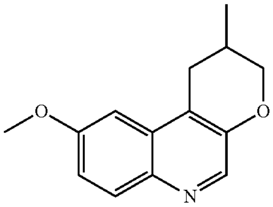 [SMILES: COc1ccc2ncc3c(c2c1)CC(C)CO3] | 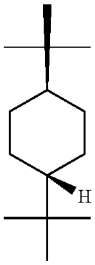 | 0 | H | C═O | 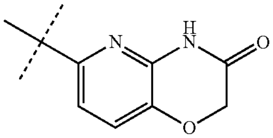 |
| 30 | 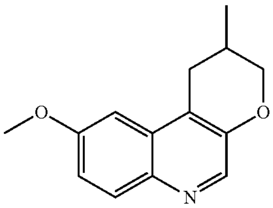 [SMILES: COc1ccc2ncc3c(c2c1)CC(C)CO3] | 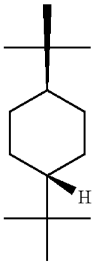 | 0 | H | C═O | 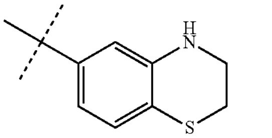 |
| 31 | 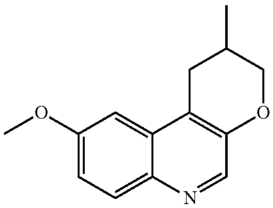 [SMILES: COc1ccc2ncc3c(c2c1)CC(C)CO3] | 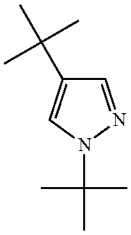 | 0 | H | C═O | 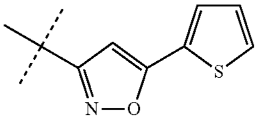 |

TABLE 1-continued
| Exemplified compounds | | | | | | |
|---|---|---|---|---|---|---|
| Example | 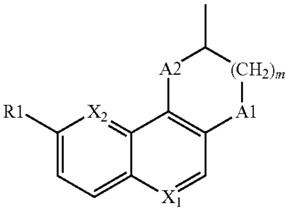 | 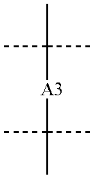 | n | R5 | A4 | G |
| 32 | 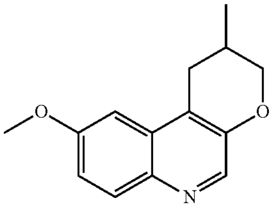 [SMILES: COc1ccc2ncc3c(c2c1)CC(C)CO3] | 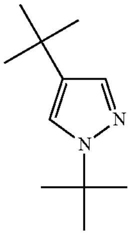 | 0 | H | C=O | 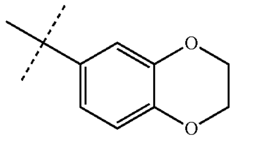 |
| 33 | 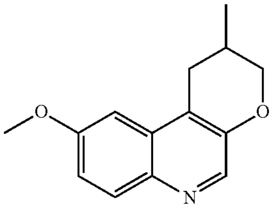 [SMILES: COc1ccc2ncc3c(c2c1)CC(C)CO3] | 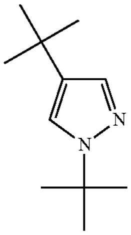 | 0 | H | C=O | 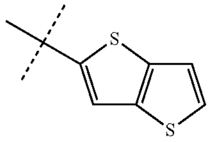 |
| 34 | 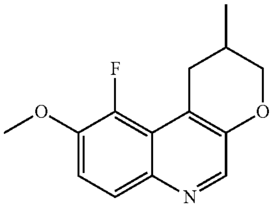 [SMILES: COc1ccc2ncc3c(c2c1F)CC(C)CO3] | 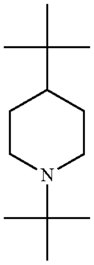 | 0 | H | C=O | 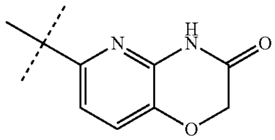 |
| 35 | 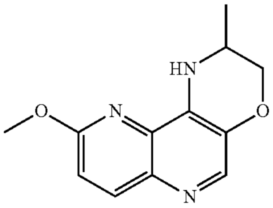 | 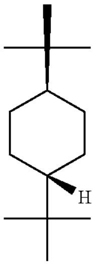 | 0 | H | C=O | 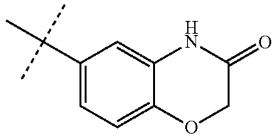 |
| 36 | 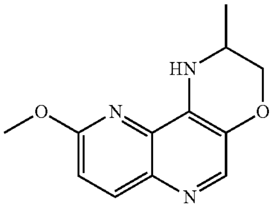 [SMILES: COc1ccc2ncc3c(c2n1)NC(C)CO3] | 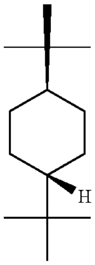 | 0 | H | C=O | 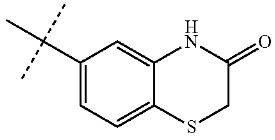 |

TABLE 1-continued
Exemplified compounds
| Example | 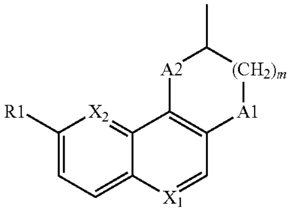 | 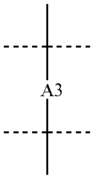 | n | R5 | A4 | G |
|---|---|---|---|---|---|---|
| 37 | 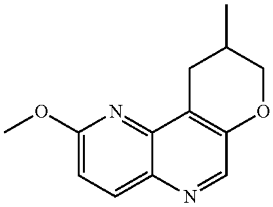 [SMILES: COc1ccc2ncc3c(c2n1)CC(C)CO3] | 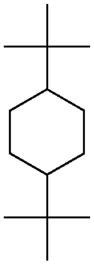 | 0 | H | C═O | 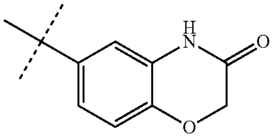 |
| 38 | 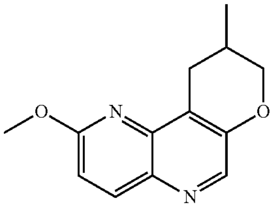 [SMILES: COc1ccc2ncc3c(c2n1)CC(C)CO3] | 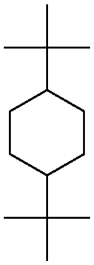 | 0 | H | C═O | 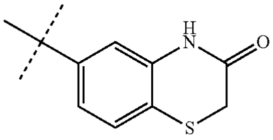 |
| 39 | 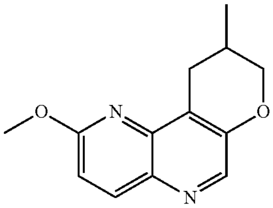 | 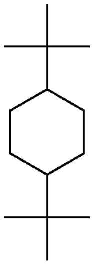 | 0 | H | —$CH_2$— | 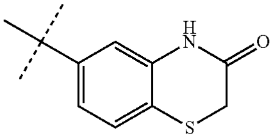 |
| 40 | 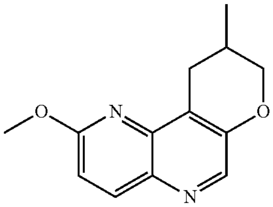 [SMILES: COc1ccc2ncc3c(c2n1)CC(C)CO3] | 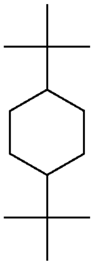 | 0 | H | C═O | 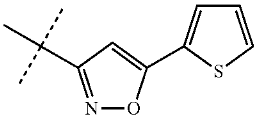 |
| 41 | 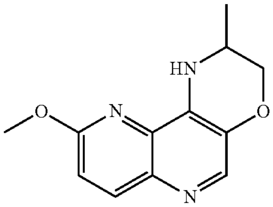 [SMILES: COc1ccc2ncc3c(c2n1)NC(C)CO3] | 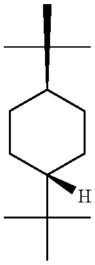 | 0 | H | C═O | 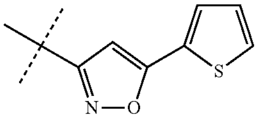 |

TABLE 1-continued
| Exemplified compounds | | | | | | |
|---|---|---|---|---|---|---|
| Example | 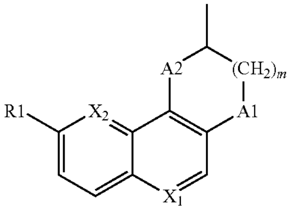 | 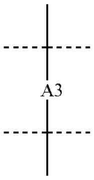 | n | R5 | A4 | G |
| 42 | 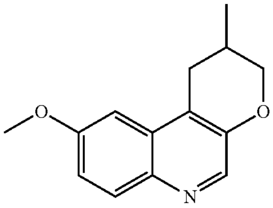 [SMILES: COc1ccc2ncc3c(c2c1)CC(C)CO3] | 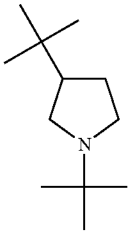 | 0 | H | C═O | 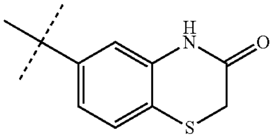 |
| 43 | 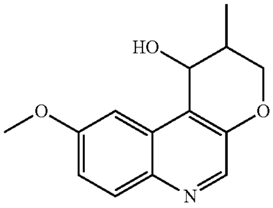 [SMILES: COc1ccc2ncc3c(c2c1)C(O)C(C)CO3] | 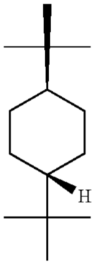 | 0 | H | C═O | 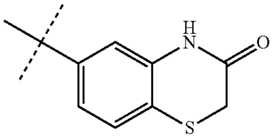 |
| 44 | 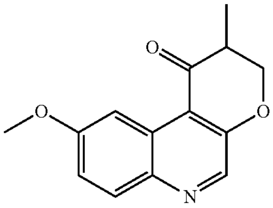 | 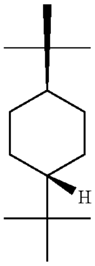 | 0 | H | C═O | 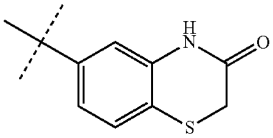 |
| 45 | 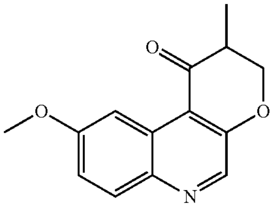 [SMILES: COc1ccc2ncc3c(c2c1)C(=O)C(C)CO3] | 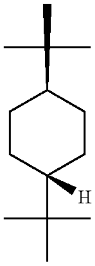 | 0 | H | $-CH_2-$ | 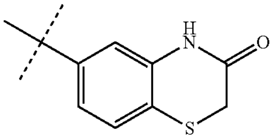 |
| 46 | 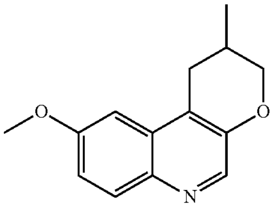 [SMILES: COc1ccc2ncc3c(c2c1)CC(C)CO3] | 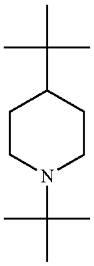 | 0 | H | C═O | 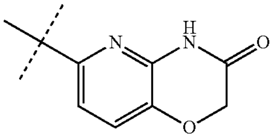 |

TABLE 1-continued
Exemplified compounds
| Example | 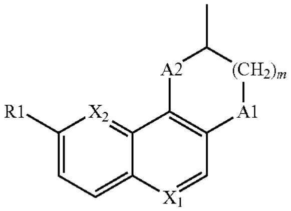 | 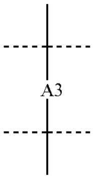 | n | R5 | A4 | G |
|---|---|---|---|---|---|---|
| 47 | 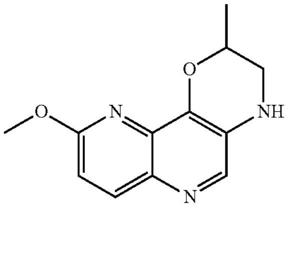 [SMILES: COc1ccc2ncc3c(c2n1)OC(C)CN3] | 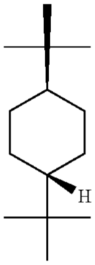 | 0 | H | C═O | 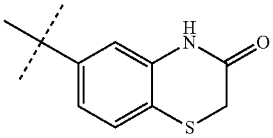 |
| 48 | 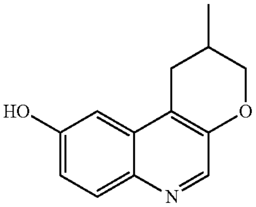 [SMILES: CC1COc2cnc3ccc(O)cc3c2C1] | 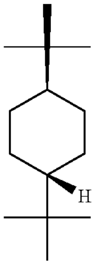 | 0 | H | C═O | 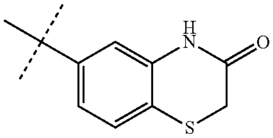 |
| 49 | 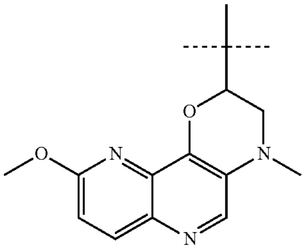 | 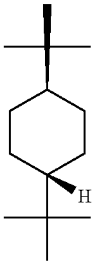 | 0 | H | C═O | 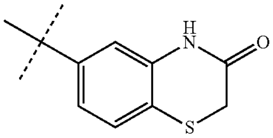 |
| 50 | 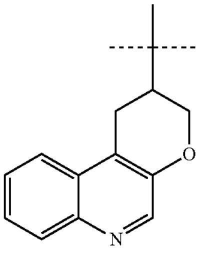 | 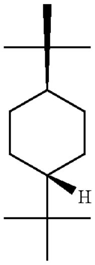 | 0 | H | C═O | 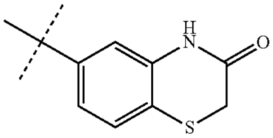 |
| 51 | 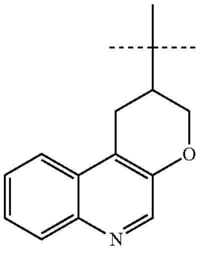 | 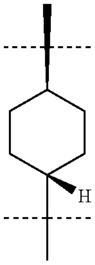 | 0 | H | C═O | 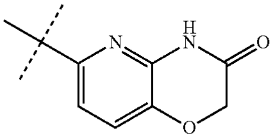 |

TABLE 1-continued
| Exemplified compounds | | | | | | |
|---|---|---|---|---|---|---|
| Example | 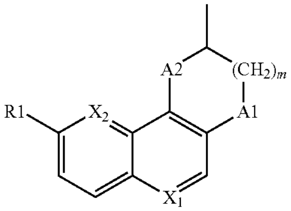 | 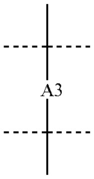 | n | R5 | A4 | G |
| 52 | 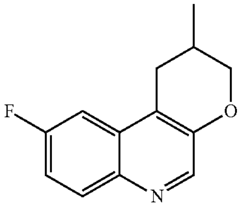 [SMILES: CC1COc2cnc3ccc(F)cc3c2C1] | 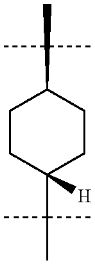 | 0 | H | C═O | 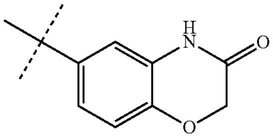 |
| 53 | 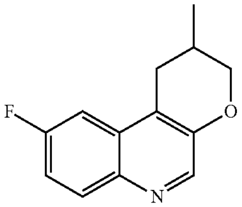 [SMILES: CC1COc2cnc3ccc(F)cc3c2C1] | 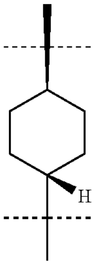 | 0 | H | C═O | 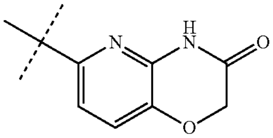 |
| 54 | 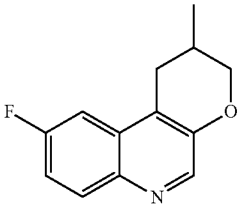 [SMILES: CC1COc2cnc3ccc(F)cc3c2C1] | 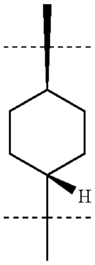 | 0 | H | $-CH_2-$ | 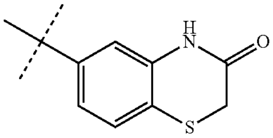 |
| 55 | 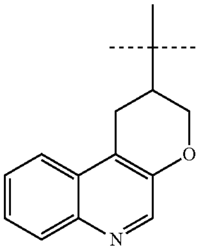 | 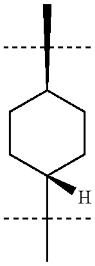 | 0 | H | C═O | 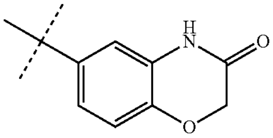 |
| 56 | 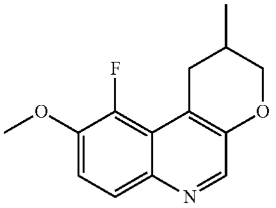 [SMILES: COc1ccc2ncc3c(c2c1F)CC(C)CO3] | 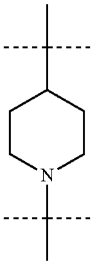 | 0 | H | C═O | 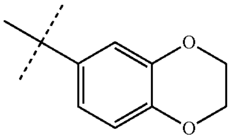 |

TABLE 1-continued
| Exemplified compounds | | | | | | |
|---|---|---|---|---|---|---|
| Example | 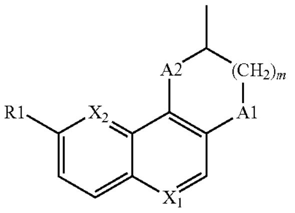 | 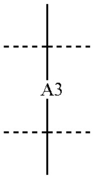 | n | R5 | A4 | G |
| 57 | 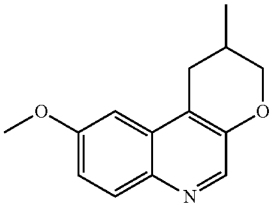 | 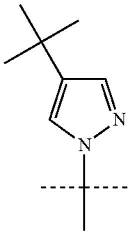 | 0 | H | —$CH_2$— | 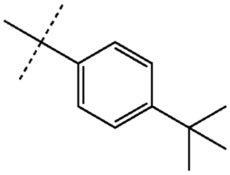 |
| 58 | 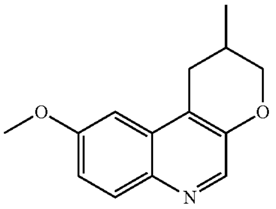 | 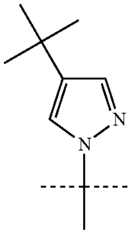 | 0 | H | —$CH_2$— | 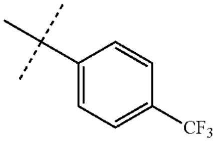 |
| 59 | 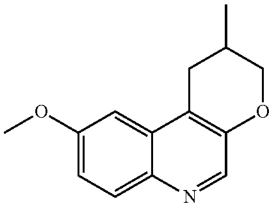 | 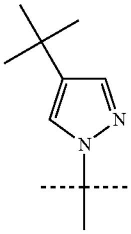 | 0 | H | —$CH_2$— | 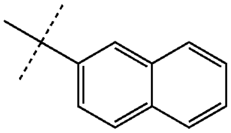 |
| 60 | 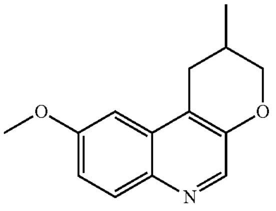 [SMILES: COc1ccc2ncc3c(c2c1)CC(C)CO3] | 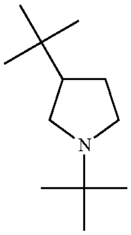 | 0 | H | C═O | 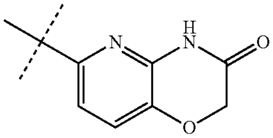 |
| 61 | 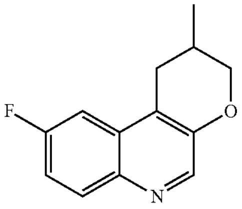 [SMILES: CC1COc2cnc3ccc(F)cc3c2C1] | 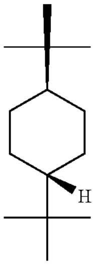 | 0 | H | C═O | 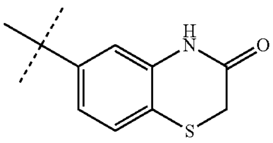 |

TABLE 1-continued
Exemplified compounds
| Example | 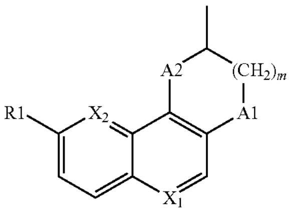 | 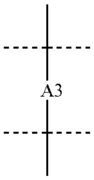 | n | R5 | A4 | G |
|---|---|---|---|---|---|---|
| 62 | 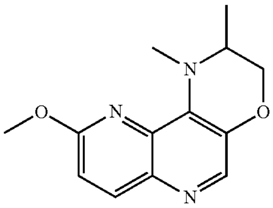 [SMILES: COc1ccc2ncc3c(c2n1)N(C)C(C)CO3] | 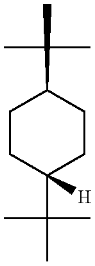 | 0 | H | C═O | 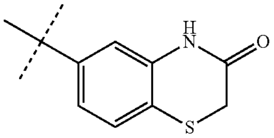 |
| 63 | 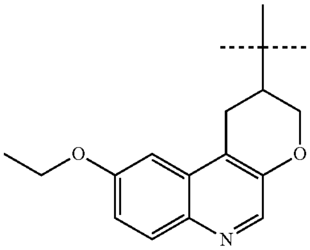 | 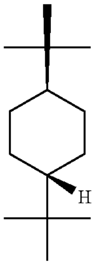 | 0 | H | C═O | 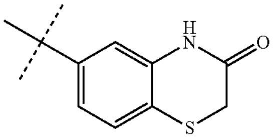 |
| 64 | 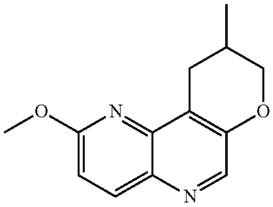 [SMILES: COc1ccc2ncc3c(c2n1)CC(C)CO3] | 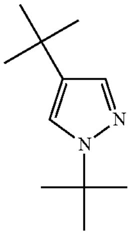 | 0 | H | C═O | 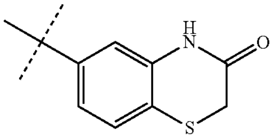 |
| 65 | 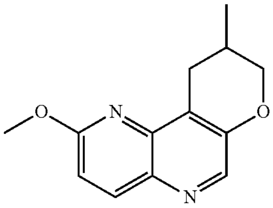 [SMILES: COc1ccc2ncc3c(c2n1)CC(C)CO3] | 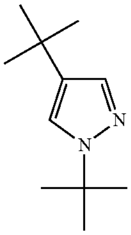 | 0 | H | C═O | 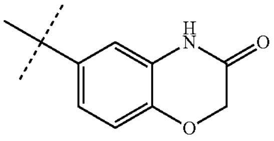 |
| 66 | 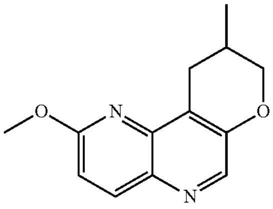 [SMILES: COc1ccc2ncc3c(c2n1)CC(C)CO3] | 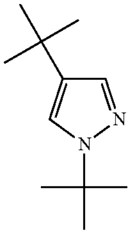 | 0 | H | C═O | 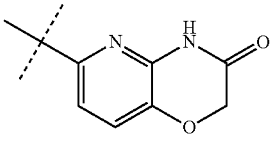 |

TABLE 1-continued
Exemplified compounds
| Example | 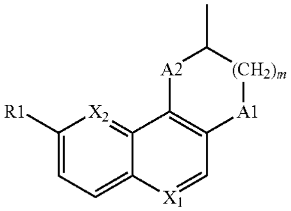 | 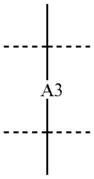 | n | R5 | A4 | G |
|---|---|---|---|---|---|---|
| 67 | 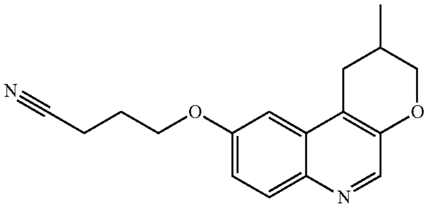 [SMILES: CC1COc2cnc3ccc(OCCCC#N)cc3c2C1] | 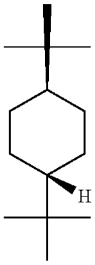 | 0 | H | C=O | 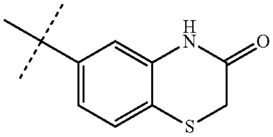 |
| 68 | 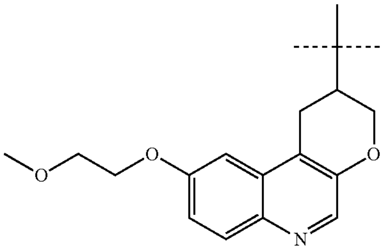 | 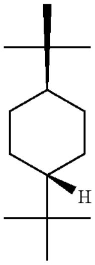 | 0 | H | C=O | 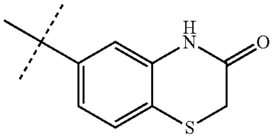 |
| 69 | 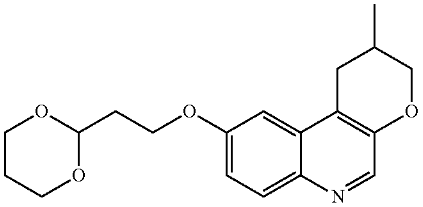 [SMILES: CC1COc2cnc3ccc(OCCC4OCCCO4)cc3c2C1] | 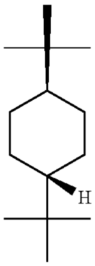 | 0 | H | C=O | 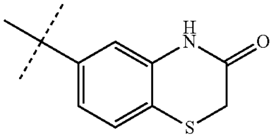 |
| 70 | 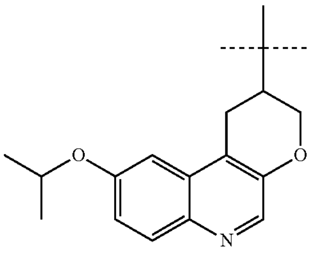 | 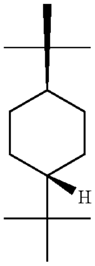 | 0 | H | C=O | 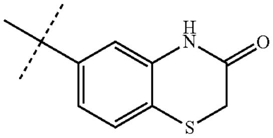 |
| 71 | 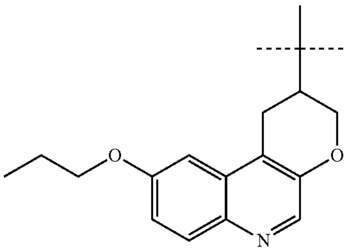 | 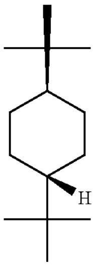 | 0 | H | C=O | 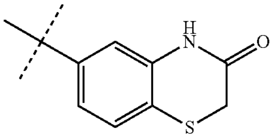 |

TABLE 1-continued
| Exemplified compounds | | | | | | |
|---|---|---|---|---|---|---|
| Example | 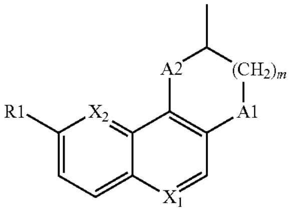 | 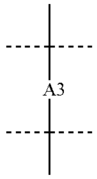 | n | R5 | A4 | G |
| 72 | 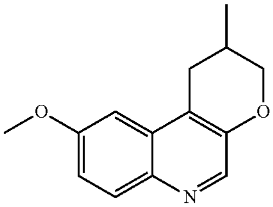 [SMILES: COc1ccc2ncc3c(c2c1)CC(C)CO3] | 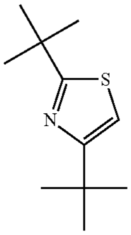 | 0 | H | C═O | 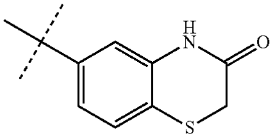 |
| 73 | 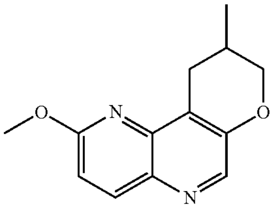 [SMILES: COc1ccc2ncc3c(c2n1)CC(C)CO3] | 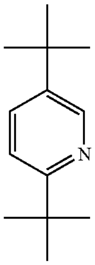 | 0 | H | C═O | 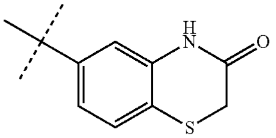 |
| 74 | 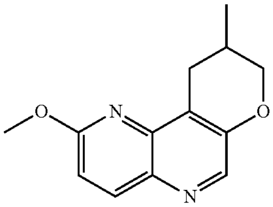 [SMILES: COc1ccc2ncc3c(c2n1)CC(C)CO3] | 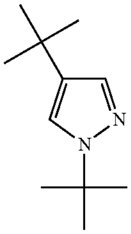 | 0 | H | $-CH_2-$ | 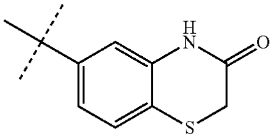 |
| 75 | 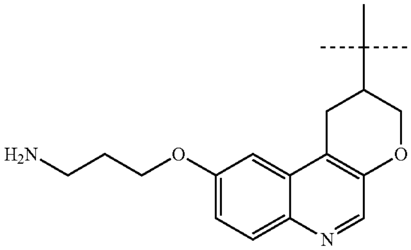 | 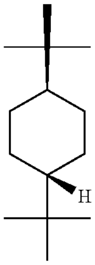 | 0 | H | C═O | 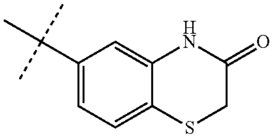 |
| 76 | 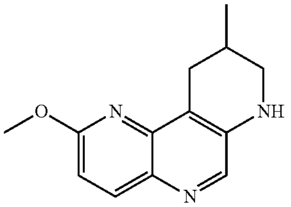 [SMILES: COc1ccc2ncc3c(c2n1)CC(C)CN3] | 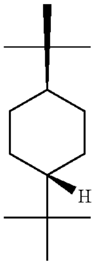 | 0 | H | C═O | 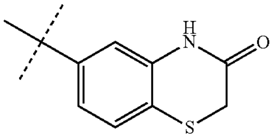 |

TABLE 1-continued
| Exemplified compounds | | | | | | |
|---|---|---|---|---|---|---|
| Example | 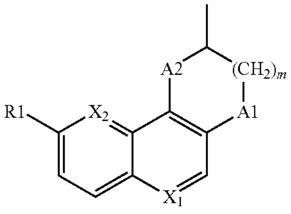 | 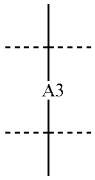 | n | R5 | A4 | G |
| 77 | 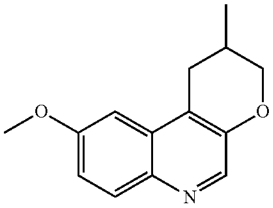 | 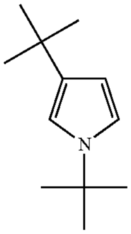 | 0 | H | C═O | 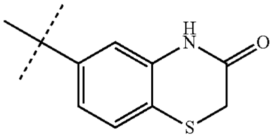 |
| 78 | 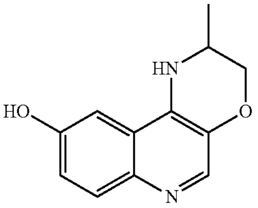 [SMILES: CC1COc2cnc3ccc(O)cc3c2N1] | 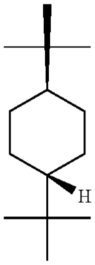 | 0 | H | C═O | 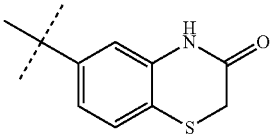 |
| 79 | 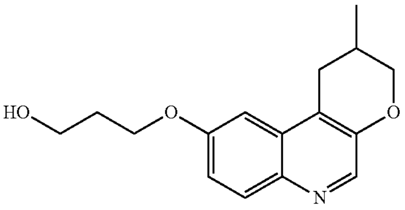 [SMILES: CC1COc2cnc3ccc(OCCCO)cc3c2C1] | 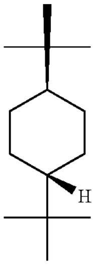 | 0 | H | C═O | 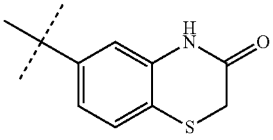 |
| 80 | 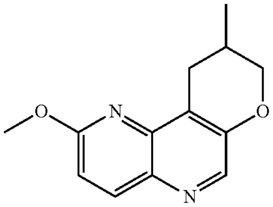 | 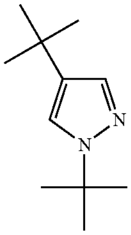 | 0 | H | —$CH_2$— | 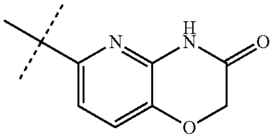 |
| 81 | 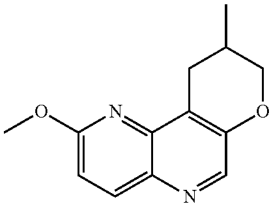 | 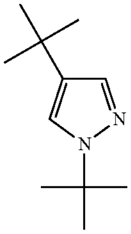 | 0 | H | —$CH_2$— | 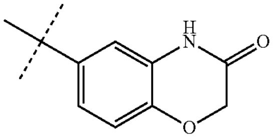 |

TABLE 1-continued

Exemplified compounds

| Example | 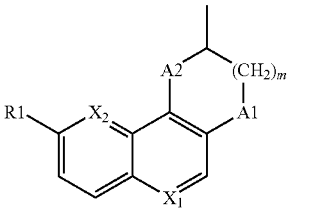 | 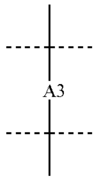 | n | R5 | A4 | G |
|---|---|---|---|---|---|---|
| 82 | 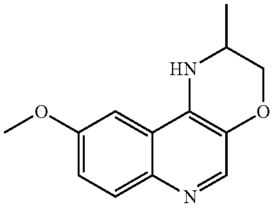 [SMILES: COc1ccc2ncc3c(c2c1)NC(C)CO3] | 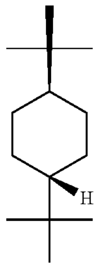 | 0 | H | C═O | 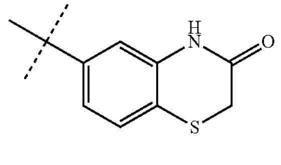 |

The numbers of the compounds of formula I used in the leftmost column of Table 1 are used in the whole application text for identifying the respective compounds.

Example 1

3-oxo-3,4-dihydro-2H-benzo[1,4]thiazine-6-carboxylic acid [1-(6-methoxy-3,4-dihydro-2H-1-oxa-9-aza-phenanthrene-3-yl)-piperidin-4-yl]-amide

Preparation of 3-chloro-2-oxo-propionic acid

A solution of 2-oxo-propionic acid (50.0 g, 568 mmol, 1.0 eq) in thionyl chloride (79.0 g, 585 mmol, 1.03 eq) is stirred at room temperature for 60 hours. The reaction mixture is dried under vacuum to afford crude 3-chloro-2-oxo-propionic acid as a light yellow viscous oil (60.0 g, 86% yield).

Preparation of 3-hydroxy-6-methoxyquinoline-4-carboxylic acid

3-Chloro-2-oxo-propionic acid (11.46 g, 91.10 mmol, 1.61 eq) is added portionwise at room temperature to a stirred solution of 5-methoxy-1H-indole-2,3-dione (10.0 g, 56.45 mmol, 1.0 eq) and potassium hydroxide (30.5 g, 543.6 mmol, 9.6 eq) in water (60 mL). After 6 days stirring at room temperature, a solution of sodium hydrogen sulfite (2.3 g, 22.10 mmol, 0.4 eq) in water (4 mL) is added and the reaction mixture is acidified by the addition of concentrated hydrochloric acid (12N, 30 mL). The resulting yellow precipitate is collected by filtration, washed with a saturated sulfur dioxide aqueous solution and water, then purified by column chromatography (silica gel, eluent:ethyl acetate:acetonitrile:methanol:water, 70:5:2.5:2.5, v/v/v/v) to afford 3-hydroxy-6-methoxyquinoline-4-carboxylic acid as a light brown solid (2.66 g, 21% yield).

$^1$H-NMR (400 MHz, DMSO-d6) δ ppm: 8.55 (s, 1H), 7.84 (d, J=8.8 Hz, 1H), 7.66 (s, 1H), 7.20 (d, J=8.8 Hz, 1H), 3.84 (s, 3H).

MS m/z (−ESI): 217.9 $[M-H]^-$.

Preparation of 3-hydroxy-6-methoxyquinoline-4-carboxylic acid methyl ester

Concentrated sulfuric acid (36N, 50 mL) is added dropwise at room temperature to a stirred suspension of 3-hydroxy-6-methoxyquinoline-4-carboxylic acid (14.5 g, 66.15 mmol, 1.0 eq) in methanol (250 mL) and the resulting mixture is heated at 65° C. for 36 hours. Solvent is then evaporated and the residue is quenched with the dropwise addition at 0° C. of saturated sodium hydrogen carbonate aqueous solution. The resulting precipitate is collected by filtration and dried under vacuum to afford 3-hydroxy-6-methoxyquinoline-4-carboxylic acid methyl ester as an off-white powder (15.0 g, 97% yield).

$^1$H-NMR (400 MHz, Acetone-d6) δ ppm: 8.56 (s, 1H), 8.00 (d, J=2.4 Hz, 1H), 7.91 (d, J=9.2 Hz, 1H), 7.23 (dd, J=2.4, 9.2 Hz, 1H), 4.16 (s, 3H), 3.95 (s, 3H).

MS m/z (+ESI): 234.0 $[M+H]^+$.

Preparation of 4-hydroxymethyl-6-methoxy-quinoline-3-ol

A solution of 3-hydroxy-6-methoxyquinoline-4-carboxylic acid methyl ester (5 g, 21.44 mmol, 1.0 eq) in tetrahydrofuran (40 mL) is added at 0° C. to a stirred solution of lithium aluminium hydride (1.63 g, 42.88 mmol, 2.0 eq) in tetrahydrofuran (200 mL). After 1 hour stirring at 0° C., the reaction mixture is cautiously quenched with ice-water (5 mL). After 30 minutes stirring at room temperature, the pH is adjusted to 6 by the addition of a 1N hydrochloric acid aqueous solution, the resulting mixture is filtered and the filtrate is concentrated to afford 4-hydroxymethyl-6-methoxy-quinoline-3-ol as a yellow solid (4 g, 90% yield).

$^1$H-NMR (400 MHz, Acetone-d6) δ ppm: 8.40 (s, 1H), 7.81 (d, J=9.2 Hz, 1H), 7.27 (d, J=2.4 Hz, 1H), 7.13 (dd, J=2.4, 9.2 Hz, 1H), 5.27 (s, 2H), 3.92 (s, 3H).

MS m/z (+ESI): 206.2 $[M+H]^+$.

Preparation of 3-hydroxy-6-methoxy-quinoline-4-carbaldehyde

Manganese dioxide (650 mg, 7.5 mmol, 10.0 eq) is added at room temperature to a stirred solution of 4-hydroxymethyl- 6-methoxy-quinoline-3-ol (220 mg, 0.75 mmol, 1.0 eq) in acetone (30 mL). After 2 hours stirring at room temperature, the reaction mixture is filtered through decalite and the filtrate is concentrated to give a residue that is purified by column chromatography (silica gel, eluent: hexane:acetone, 1:1, v/v) to afford 3-hydroxy-6-methoxy-quinoline-4-carbaldehyde as a yellow solid (85 mg, 34% yield).

$^1$H-NMR (400 MHz, Acetone-d6) δ ppm: 11.04 (s, 1H), 8.61 (s, 1H), 8.15 (d, J=2.4 Hz, 1H), 7.93 (d, J=9.2 Hz, 1H), 7.25 (dd, J=2.4, 9.2 Hz, 1H), 3.99 (s, 3H).

MS m/z (+ESI): 204.0 $[M+H]^+$.

Preparation of 6-methoxy-2H-1-oxa-9-aza-phenanthrene-3-carbonitrile 1,4-Diazabicyclo[2.2.2]octane (345 mg, 3.07 mmol, 0.25 eq) is added at room temperature to a stirred suspension of 3-hydroxy-6-methoxy-quinoline-4-carbaldehyde (2.5 g, 12.3 mmol, 1.0 eq) in acrylonitrile (25 mL) and the resulting mixture is heated under reflux for 60 hours. The reaction mixture is then cooled to room temperature and extracted with ethyl acetate (3×100 mL) and a 1N sodium hydroxide aqueous solution (50 mL). The combined organic layers are dried over sodium sulfate, filtered and concentrated to give a residue that is purified by column chromatography (silica gel, eluent: hexane:ethyl acetate, 5:1, v/v) to afford 6-methoxy-2H-1-oxa-9-aza-phenanthrene-3-carbonitrile as a light yellow solid (2.3 g, 78% yield).

$^1$H-NMR (400 MHz, Acetone-d6) δ ppm: 8.44 (s, 1H), 8.26 (s, 1H), 7.88 (d, J=9.2 Hz, 1H), 7.56 (d, J=2.4 Hz, 1H), 7.27 (dd, J=2.4, 9.2 Hz, 1H), 5.08 (s, 2H), 3.99 (s, 3H).

MS m/z (+ESI): 239.1 $[M+H]^+$.

Preparation of 6-methoxy-2H-1-oxa-9-aza-phenanthrene-3-carboxylic acid

10% sodium hydroxide aqueous solution (950 mL) is added at room temperature to a stirred solution of 6-methoxy-2H-1-oxa-9-aza-phenanthrene-3-carbonitrile (9.5 g, 39.87 mmol, 1.0 eq) in tetrahydrofuran (190 mL) and the resulting mixture is heated under reflux for 8 hours. The reaction mixture is then cooled to room temperature, acidified until pH=6 with a 2N hydrochloric acid aqueous solution, and the resulting precipitate is collected by filtration to afford 6-methoxy-2H-1-oxa-9-aza-phenanthrene-3-carboxylic acid as a yellow solid (6.7 g, 65% yield).

$^1$H-NMR (400 MHz, DMSO-d6) δ ppm: 8.43 (s, 1H), 8.12 (s, 1H), 7.82 (d, J=9.2 Hz, 1H), 7.47 (s, 1H), 7.23 (d, J=9.2 Hz, 1H), 5.05 (s, 2H), 3.97 (s, 3H).

MS m/z (+ESI): 258.1 $[M+H]^+$.

Preparation of 6-methoxy-4H-1-oxa-9-aza-phenanthrene-3-one

Triethylamine (13 μL, 0.09 mmol, 1.2 eq) is added at room temperature to a stirred solution of 6-methoxy-2H-1-oxa-9-aza-phenanthrene-3-carboxylic acid (20 mg, 0.08 mmol, 1.0 eq) in dichloromethane (1 mL), followed by a solution of diphenylphosphoryl azide (23 mg, 0.08 mmol, 1.0 eq) in toluene (1.5 mL). After 1 h30 stirring at 80° C., 6M hydrochloric acid aqueous solution (0.5 mL) is added and the resulting mixture is heated at 90° C. for 2 hours. The reaction mixture is then cooled down to room temperature and extracted with ethyl acetate (3×10 mL) and saturated sodium hydrogen carbonate aqueous solution (10 mL). The combined organic layers are dried over sodium sulfate, filtered and concentrated to give a residue that is purified by column chromatography (silica gel, eluent: ethyl acetate) to afford 6-methoxy-4H-1-oxa-9-aza-phenanthrene-3-one as a yellow semisolid (5 mg, 28% yield).

$^1$H-NMR (400 MHz, Acetone-d6) δ ppm: 8.51 (s, 1H), 7.94 (d, J=8.8 Hz, 1H), 7.26 (d, J=9.2 Hz, 1H), 7.25 (s, 1H), 4.63 (s, 2H), 3.98 (s, 5H).

MS m/z (+ESI): 230.1 $[M+H]^+$.

Preparation of [1-(6-methoxy-3,4-dihydro-2H-1-oxa-9-aza-phenanthrene-3-yl)-piperidin-4-yl]-carbamic acid tert-butyl ester A solution of piperidin-4-yl-carbamic acid tert-butyl ester (76 mg, 0.38 mmol, 1.0 eq) in 1,2-dichloroethane (1 mL) is added at room temperature to a stirred solution of 6-methoxy-4H-1-oxa-9-aza-phenanthrene-3-one (87 mg, 0.38 mmol, 1.0 eq) in tetrahydrofuran (6 mL), followed by acetic acid (5 μL, 0.08 mmol, 0.2 eq) and the resulting mixture is heated under reflux for 3 hours. The reaction mixture is then cooled down to room temperature before the addition of a solution of sodium cyanoborohydride (48 mg, 0.76 mmol, 2.0 eq) in methanol (1 mL). After 15 hours stirring at room temperature, solvents are evaporated and to give a residue that is purified by preparative HPLC to afford [1-(6-methoxy-3,4-dihydro-2H-1-oxa-9-aza-phenanthrene-3-yl)-piperidin-4-yl]-carbamic acid tert-butyl ester as a light yellow solid (10 mg, 6% yield).

$^1$H-NMR (400 MHz, DMSO-d6) δ ppm: 8.30 (s, 1H), 7.82 (d, J=9.3 Hz, 1H), 7.20 (m, 2H), 6.77 (d, J=5.6 Hz, 1H), 4.42 (d, J=10.9 Hz, 1H), 4.00 (m, 1H), 3.93 (s, 3H), 3.18 (m, 1H), 3.00 (m, 4H), 2.35 (m, 2H), 1.72 (m, 2H), 1.39 (m, 12H).

MS m/z (+ESI): 414.3 $[M+H]^+$.

Preparation of 1-(6-methoxy-3,4-dihydro-2H-1-oxa-9-aza-phenanthrene-3-yl)-piperidin-4-ylamine Trifluoroacetic acid (1.23 mL, 15.78 mmol, 15.0 eq) is added at 0° C. to a stirred solution of [1-(6-methoxy-3,4-dihydro-2H-1-oxa-9-aza-phenanthrene-3-yl)-piperidin-4-yl]-carbamic acid tert-butyl ester (500 mg, 1.05 mmol, 1.0 eq) in dichloromethane (50 mL). After 15 hours stirring at room temperature, the reaction mixture is extracted with dichloromethane (3×30 mL) and water (30 mL) and the pH is adjusted to 12 by the addition of a 1N sodium hydroxide aqueous solution. The combined organic layers are dried over sodium sulfate, filtered and concentrated to afford 1-(6-methoxy-3,4-dihydro-2H-1-oxa-9-aza-phenanthrene-3-yl)-piperidin-4-ylamine as a brown solid (325 mg, 84% yield).

$^1$H-NMR (400 MHz, DMSO-d6) δ ppm: 8.32 (s, 1H), 7.82 (d, J=9.7 Hz, 1H), 7.20 (m, 2H), 4.42 (d, J=11.3 Hz, 1H), 3.99 (m, 1H), 3.91 (s, 3H), 3.18 (m, 1H), 2.98 (m, 4H), 2.61 (m, 1H), 2.33 (m, 2H), 1.72 (m, 2H), 1.23 (m, 2H).

MS m/z (+ESI): 314.3 $[M+H]^+$.

Preparation of 3-oxo-3,4-dihydro-2H-benzo[1,4]thiazine-6-carboxylic acid [1-(6-methoxy-3,4-dihydro-2H-1-oxa-9-aza-phenanthrene-3-yl)-piperidin-4-yl]-amide 3-Oxo-3,4-dihydro-2H-benzo[1,4]thiazine-6-carboxylic acid (31 mg, 0.14 mmol, 1.0 eq) is added at room temperature to a stirred solution of 1-(6-methoxy-3,4-dihydro-2H-1-oxa-9-aza-phenanthrene-3-yl)-piperidin-4-ylamine (50 mg, 0.14 mmol, 1.0 eq) in N,N-dimethylformamide (3 mL), followed by 1-hydroxybenzotriazole (21 mg, 0.15 mmol, 1.1 eq), N-(3-dimethylaminopropyl)-N'-ethylcarbodiimide hydrochloride (31 mg, 0.16 mmol, 1.15 eq) and N,N-diisopropylethylamine (53 μL, 0.31 mmol, 2.25 eq). After 15 hours stirring at room temperature, solvent is evaporated and the residue is extracted with dichloromethane (3×10 mL) and water (10 mL). The combined organic layers are dried over sodium sulfate, filtered and concentrated to give a crude product that is purified by preparative HPLC to afford 3-oxo-3,4-dihydro-2H-benzo[1,4]thiazine-6-carboxylic acid [1-(6-methoxy-3,4-dihydro-2H-1-oxa-9-aza-phenanthrene-3-yl)-piperidin-4-yl]-amide as an off-white lyophilizated powder (24 mg, 33% yield).

$^1$H-NMR (400 MHz, DMSO-d6) δ ppm: 10.66 (br, 1H), 8.33 (s, 1H), 8.24 (d, J=7.6 Hz, 1H), 7.81 (d, J=9.0 Hz, 1H), 7.42 (m, 2H), 7.38 (m, 1H), 7.20 (m, 2H), 4.47 (d, J=11.0 Hz, 1H), 4.02 (m, 1H), 3.93 (s, 3H), 3.78 (m, 1H), 3.50 (s, 2H), 3.20 (m, 1H), 3.08 (m, 2H), 3.00 (m, 2H), 2.42 (m, 2H), 1.81 (m, 2H), 1.58 (m, 2H).

MS m/z (+ESI): 505.2 $[M+H]^+$.

Example 2

6-{[1-(6-methoxy-3,4-dihydro-2H-1-oxa-9-aza-phenanthrene-3-yl)-piperidin-4-ylamino]-methyl}-4H-benzo[1,4]thiazine-3-one 3-Oxo-3,4-dihydro-2H-benzo[1,4]thiazine-6-carbaldehyde (28 mg, 0.14 mmol 1.0 eq) is added at room temperature to a stirred solution of 1-(6-methoxy-3,4-dihydro-2H-1-oxa-9-aza-phenanthrene-3-yl)-piperidin-4-ylamine (50 mg, 0.14 mmol, 1.0 eq) in 1,2-dichloroethane (3 mL) and methanol (1.5 mL), followed by acetic acid (9 μL, 0.16 mmol, 1.15 eq) and sodium cyanoborohydride (12 mg, 0.18 mmol, 1.3 eq). After 15 hours stirring at room temperature, the reaction mixture is extracted with dichloromethane (3×10 mL) and a saturated sodium hydrogen carbonate aqueous solution (10 mL). The combined organic layers are dried over sodium sulfate, filtered and concentrated to give a residue that is purified by preparative HPLC to afford 6-{[1-(6-methoxy-3,4-dihydro-2H-1-oxa-9-aza-phenanthrene-3-yl)-piperidin-4-ylamino]-methyl}-4H-benzo[1,4]thiazine-3-one as an off-white lyophilizated solid (25 mg, 36% yield).

$^1$H-NMR (400 MHz, DMSO-d6) δ ppm: 10.50 (br, 1H), 8.32 (s, 1H), 7.82 (d, J=7.4 Hz, 1H), 7.20 (m, 3H), 6.97 (m, 2H), 4.42 (d, J=11.4 Hz, 1H), 4.00 (m, 1H), 3.91 (s, 3H), 3.68 (s, 2H), 3.42 (s, 2H), 3.10 (m, 1H), 3.00 (m, 4H), 2.40 (m, 1H), 2.30 (m, 2H), 1.82 (m, 2H), 1.29 (m, 2H).

MS m/z (+ESI): 491.2 $[M+H]^+$.

Example 3

6-{[1-(6-methoxy-3,4-dihydro-2H-1-thia-9-aza-phenanthrene-3-yl)-piperidin-4-ylamino]-methyl}-4H-benzo[1,4]oxazin-3-one

Preparation of 6-methoxy-3-trifluoromethanesulfonyloxy-quinoline-4-carboxylic acid methyl ester Trifluoromethanesulfonic anhydride (3.35 mL, 19.94 mmol, 1.5 eq) is added at room temperature to a stirred solution of 3-hydroxy-6-methoxy-quinoline-4-carboxylic acid methyl ester (3.1 g, 13.29 mmol, 1.0 eq) in dichloromethane (30 mL), followed by triethylamine (5.6 mL, 39.88 mmol, 3.0 eq). After 1 hour stirring at room temperature, solvent is removed and the residue is purified by column chromatography (silica gel, eluent: petroleum ether:ethyl acetate, 5:1, v/v) to afford 6-methoxy-3-trifluoromethanesulfonyloxy-quinoline-4-carboxylic acid methyl ester as a yellow solid (3.69 g, 76% yield).

$^1$H-NMR (400 MHz, DMSO-d6) δ ppm: 8.93 (s, 1H), 8.11 (d, J=9.2 Hz, 1H), 7.63 (dd, J=2.8, 9.2 Hz, 1H), 7.42 (d, J=2.8 Hz, 1H), 4.05 (s, 3H), 3.93 (s, 3H).

MS m/z (+ESI): 366.0 $[M+H]^+$.

Preparation of 6-methoxy-3-(4-methoxy-benzylsulfanyl)-quinoline-4-carboxylic acid methyl ester A mixture of 6-methoxy-3-trifluoromethanesulfonyloxy-quinoline-4-carboxylic acid methyl ester (3.69 g, 10.10 mmol, 1.0 eq), (4-methoxy-phenyl)-methanethiol (3.43 g, 22.22 mmol, 2.2 eq), 4,5-bis(diphenylphosphino)-9,9-dimethylxanthene (409 mg, 0.71 mmol, 0.07 eq), tris(dibenzylideneacetone)dipalladium(0) (925 mg, 1.01 mmol, 0.1 eq) and N,N-diisopropylethylamine (3.46 mL, 20.20 mmol, 2.0 eq) in dioxane (40 mL) is heated under reflux for 16 hours, then filtered through decalite and concentrated to give a residue that is purified by column chromatography (silica gel, eluent: petroleum ether:ethyl acetate, 5:1, v/v) to afford 6-methoxy-3-(4-methoxy-benzylsulfanyl)-quinoline-4-carboxylic acid methyl ester as an off-white solid (3.30 g, 88% yield).

$^1$H-NMR (400 MHz, DMSO-d6) δ ppm: 8.78 (s, 1H), 7.94 (d, J=9.2 Hz, 1H), 7.43 (d, J=9.2 Hz, 1H), 7.19 (d, J=8.2 Hz, 2H), 6.92 (s, 1H), 6.81 (d, J=8.2 Hz, 2H), 4.31 (s, 2H), 3.98 (s, 3H), 3.86 (s, 3H), 3.68 (s, 3H).

MS m/z (+ESI): 370.0 $[M+H]^+$.

Preparation of 3-mercapto-6-methoxy-quinoline-4-carboxylic acid methyl ester Mercuric acetate (30.97 g, 97.17 mmol, 1.0 eq) is added at 0° C. to a stirred solution of 6-methoxy-3-(4-methoxy-benzylsulfanyl)-quinoline-4-carboxylic acid methyl ester (35.90 g, 97.17 mmol, 1.0 eq) in trifluoroacetic acid (180 mL) and anisole (36 mL). After 45 minutes stirring at 0° C., solvents are removed to give a crude that is poured into a solution of sodium sulfide nonahydrate (75.85 g, 315.80 mmol, 3.25 eq) in ethyl acetate (300 mL), water (300 mL) and acetic acid (55.6 mL, 971.74 mmol, 10.0 eq). After 1 hour stirring at room temperature, the solution is acidified until pH=6 with a 1N hydrochloric acid aqueous solution and the resulting mixture is filtered through decalite. The organic layer is separated and the aqueous layer is extracted with ethyl acetate (3×200 mL). The combined organic layers are dried over sodium sulfate, filtered and concentrated to afford a mixture of 3-mercapto-6-methoxy-quinoline-4-carboxylic acid methyl ester and its corresponding dimer as an orange solid (24.22 g, 99.5% yield).

$^1$H-NMR (400 MHz, DMSO-d6) δ ppm: 8.93 (br, 1H), 7.99 (m, 1H), 7.49 (br, 1H), 6.97 (br, 1H), 3.97 (br, 3H), 3.85 (br, 3H).

MS m/z (+ESI): 249.2 $[M_{thiol}]^+$, 497.2 $[M_{dimer}+H]^+$.

Preparation of (3-mercapto-6-methoxy-quinoline-4-yl)-methanol

A 1.0 M solution of lithium aluminium hydride in diethyl ether (10.23 mL, 10.23 mmol) is added at 0° C. to a stirred solution of 3-mercapto-6-methoxy-quinoline-4-carboxylic acid methyl ester and its corresponding dimer (1.27 g) in tetrahydrofuran (40 mL). After 1 hour stirring at 0° C., the reaction mixture is cautiously quenched with water and a sodium hydroxide aqueous solution (15 weight percent). The resulting precipitate is collected by filtration, dissolved in water (20 mL) and the pH is adjusted to 3 with a saturated sodium hydrogen sulfate aqueous solution at 0° C. The obtained solution is extracted with ethyl acetate (3×30 mL). The combined organic layers are dried over sodium sulfate, filtered and concentrated to afford a mixture of (3-mercapto-6-methoxy-quinoline-4-yl)-methanol and its corresponding dimer as a red solid (1.11 g, 49% yield).

$^1$H-NMR (400 MHz, DMSO-d6) δ ppm: 8.37 (s, 1H), 7.56 (d, J=8.8 Hz, 1H), 7.10 (s, 1H), 6.87 (d, J=8.8 Hz, 1H), 6.77 (t, J=6.0 Hz, 1H), 4.89 (d, J=6.0 Hz, 2H), 3.81 (s, 3H).

MS m/z (+ESI): 222.0 $[M_{thiol}+H]^+$, 441.0 $[M_{dimer}+H]^+$.

Preparation of 3-mercapto-6-methoxy-quinoline-4-carbaldehyde disulfide analogue

Manganese dioxide (1.38 g, 15.89 mmol) is added at room temperature to a stirred solution of (3-mercapto-6-methoxy-quinoline-4-yl)-methanol and its corresponding dimer (500 mg) in acetone (30 mL) and the resulting suspension is heated under reflux for 8 hours. The reaction mixture is then filtered through decalite and the filtrate is concentrated to give a residue that is purified by column chromatography (silica gel, eluent: petroleum ether:ethyl acetate, 2:1, v/v) to afford 3-mercapto-6-methoxy-quinoline-4-carbaldehyde and its corresponding dimer as a yellow solid (64 mg, 13% yield).

$^1$H-NMR (400 MHz, $CDCl_3$) δ ppm: 10.94 (s, 1H), 9.14 (s, 1H), 7.90-8.12 (m, 2H), 7.41 (m, 1H), 3.96 (s, 3H).

MS m/z (+ESI): 437.0 $[M_{dimer}+H]^+$.

Preparation of 4-hydroxy-6-methoxy-3,4-dihydro-2H-1-thia-9-aza-phenanthrene-3-carboxylic acid ethyl ester 1,4-diazabicyclo[2.2.2]octane (1.04 g, 9.26 mmol) is added at room temperature to a stirred solution of (3-mercapto-6-methoxy-quinoline-4-yl)-methanol and its corresponding dimer (2.02 g) in acrylic acid ethyl ester (21.7 mL, 203.72 mmol). The reaction mixture is heated under reflux for 2 hours, cooled down to room temperature and concentrated to afford 4-hydroxy-6-methoxy-3,4-dihydro-2H-1-thia-9-aza-phenanthrene-3-carboxylic acid ethyl ester as a dark brown solid (1.47 g, 99.5% yield).

MS m/z (+ESI): 320.2 $[M+H]^+$.

Preparation of 6-methoxy-2H-1-thia-9-aza-phenanthrene-3-carboxylic acid ethyl ester Methanesulfonyl chloride (745 µL, 9.63 mmol, 3.0 eq) is added at room temperature to a stirred solution of 4-hydroxy-6-methoxy-3,4-dihydro-2H-1-thia-9-aza-phenanthrene-3-carboxylic acid ethyl ester (1.02 g, 3.21 mmol, 1.0 eq) in dichloromethane (10 mL), followed by triethylamine (2.23 mL, 16.05 mmol, 5.0 eq) and 4-(dimethylamino)pyridine (392 mg, 3.21 mmol, 1.0 eq). After 20 minutes stirring at room temperature, solvent is removed and the crude product is purified by column chromatography (silica gel, eluent: petroleum ether:ethyl acetate, 10:1, v/v) to afford 6-methoxy-2H-1-thia-9-aza-phenanthrene-3-carboxylic acid ethyl ester as a yellow solid (330 mg, 34% yield).

$^1$H-NMR (400 MHz, DMSO-d6) δ ppm: 8.68 (s, 1H), 8.16 (s, 1H), 7.89 (d, J=10.0 Hz, 1H), 7.35 (m, 2H); 4.30 (q, J=7.2 Hz, 2H), 3.95 (s, 3H), 3.79 (s, 2H), 1.32 (t, J=7.2 Hz, 3H).

MS m/z (+ESI): 302.3 $[M+H]^+$.

Preparation of 6-methoxy-2H-1-thia-9-aza-phenanthrene-3-carboxylic acid

Lithium hydroxide monohydrate (731 mg, 17.42 mmol, 15.0 eq) is added at room temperature to a stirred solution of 6-methoxy-2H-1-thia-9-aza-phenanthrene-3-carboxylic acid ethyl ester (350 mg, 1.16 mmol, 1.0 eq) in tetrahydrofuran (5 mL) and water (5 mL). After 2 hours stirring at room temperature, the reaction mixture is acidified until pH=6 with a 1N hydrochloric acid aqueous solution and the resulting precipitate is collected by filtration, dried under vacuum to afford 6-methoxy-2H-1-thia-9-aza-phenanthrene-3-carboxylic acid as a yellow solid (280 mg, 88% yield).

$^1$H-NMR (400 MHz, DMSO-d6) δ ppm: 8.68 (s, 1H), 8.15 (s, 1H), 7.88 (d, J=8.4 Hz, 1H), 7.35 (s, 1H), 7.34 (d, J=8.4 Hz, 1H), 3.94 (s, 3H), 3.76 (s, 2H).

MS m/z (−ESI): 272.2 $[M-H]^-$.

Preparation of 6-methoxy-4H-1-thia-9-aza-phenanthren-3-one

Triethylamine (255 µL, 1.85 mmol, 5.0 eq) is added at 0° C. to a stirred solution of 6-methoxy-2H-1-thia-9-aza-phenanthrene-3-carboxylic acid (100 mg, 0.37 mmol, 1.0 eq) in acetone (5 mL), followed by ethyl chloroformate (79 mg, 0.74 mmol, 2.0 eq). After 1 hour stirring at 0° C., a solution of sodium azide (50 mg, 0.74 mmol, 2.0 eq) in water (0.5 mL) is added and the resulting mixture is stirred at 0-5° C. for 1 hour. The reaction mixture is then extracted with ethyl acetate (3×10 mL). The combined organic layers are dried over sodium sulfate, filtered and concentrated to give a residue that is purified by column chromatography (silica gel, eluent: petroleum ether:ethyl acetate, 5:1, v/v) to afford the azide intermediate that is dissolved in toluene (2 mL) and the resulting solution is heated under reflux for 3 hours. Then a 10% sulfuric acid aqueous solution (1 mL) is added and the resulting mixture is heated under reflux for 3 additional hours, cooled down to room temperature and the pH is adjusted to 7-8 with a saturated sodium hydrogen carbonate aqueous solution. The solution is then extracted with ethyl acetate (3×10 mL), the combined organic layers are dried over sodium sulfate, filtered and concentrated to afford 6-methoxy-4H-1-thia-9-aza-phenanthren-3-one as a red solid (35 mg, 39% yield).

$^1$H-NMR (400 MHz, Acetone-d6) δ ppm: 8.64 (s, 1H), 7.94 (d, J=9.0 Hz, 1H), 7.36 (d, J=9.0 Hz, 1H), 7.34 (s, 1H), 4.13 (s, 2H), 4.00 (s, 3H), 3.65 (s, 2H).

MS m/z (+ESI): 246.0 $[M+H]^+$.

Preparation of [1-(6-methoxy-3,4-dihydro-2H-1-thia-9-aza-phenanthrene-3-yl)-piperidin-4-yl]-carbamic acid tert-butyl ester A solution of piperidin-4-yl-carbamic acid tert-butyl ester (2.45 g, 12.22 mmol, 2.0 eq), 6-methoxy-4H-1-thia-9-aza-phenanthren-3-one (1.50 g, 6.11 mmol, 1.0 eq) and p-toluenesulfonic acid (526 mg, 3.06 mmol, 0.5 eq) in toluene (50 mL) is heated at 120° C. for 2 hours. The resulting solution is cooled down to room temperature, solvent is removed and the crude is dissolved in dichloromethane (100 mL) and methanol (100 mL) before the addition of acetic acid (0.5 mL, 8.66 mmol, 1.4 eq) and sodium cyanoborohydride (1.24 g, 19.73 mmol, 3.2 eq). After 1 h30 stirring at room temperature, the reaction mixture is extracted with dichloromethane (3×50 mL) and a saturated sodium hydrogen carbonate aqueous solution (50 mL). The combined organic layers are dried over sodium sulfate, filtered and concentrated to give a residue that is purified by column chromatography (silica gel, eluent: petroleum ether:ethyl acetate:ammonia-7N solution in methanol, 1:1:0.05, v/v/v) to afford [1-(6-methoxy-3,4-dihydro-2H-1-thia-9-aza-phenanthrene-3-yl)-piperidin-4-yl]-carbamic acid tert-butyl ester as a light yellow solid (746 mg, 28% yield).

$^1$H-NMR (400 MHz, DMSO-d6) δ ppm: 8.33 (s, 1H), 7.80 (d, J=9.0 Hz, 1H), 7.25 (d, J=9.0 Hz, 1H), 7.19 (s, 1H), 6.75 (d, J=3.6 Hz, 1H), 3.90 (s, 3H), 2.74-3.30 (m, 8H), 2.40-2.59 (m, 1H), 2.20-2.34 (m, 1H), 1.61-1.75 (m, 2H), 1.35 (s, 9H), 1.27-1.43 (m, 2H).

MS m/z (+ESI): 430.3 $[M+H]^+$.

Preparation of 1-(6-methoxy-3,4-dihydro-2H-1-thia-9-aza-phenanthrene-3-yl)-piperidin-4-ylamine The titled compound is prepared as a light brown solid (211 mg, 88% yield) following Scheme 1 and in analogy to Example 1 using [1-(6-methoxy-3,4-dihydro-2H-1-thia-9-aza-phenanthrene-3-yl)-piperidin-4-yl]-carbamic acid tert-butyl ester (318 mg, 0.69 mmol, 1.0 eq) as starting material.

MS m/z (+ESI): 330.3 [M+H]

Preparation of 6-{[1-(6-methoxy-3,4-dihydro-2H-1-thia-9-aza-phenanthrene-3-yl)-piperidin-4-ylamino]-methyl}-4H-benzo[1,4]oxazin-3-one The titled compound is prepared as a light yellow solid (21 mg, 28% yield) following Scheme 1 and in analogy to Example 2 using 1-(6-methoxy-3,4-dihydro-2H-1-thia-9-aza-phenanthrene-3-yl)-piperidin-4-ylamine (50 mg, 0.14 mmol, 1.0 eq) and 3-oxo-3,4-dihydro-2H-benzo[1,4]oxazine-6-carbaldehyde (27 mg, 0.14 mmol, 1.0 eq) as starting materials.

$^1$H-NMR (400 MHz, DMSO-d6) δ ppm: 10.67 (br, 1H), 8.38 (s, 1H), 7.82 (d, J=9.0 Hz, 1H), 7.26 (m, 2H), 6.89 (m, 3H), 4.52 (s, 2H), 3.91 (s, 3H), 3.68 (s, 2H), 2.98-3.28 (m, 7H), 2.88 (m, 1H), 2.41 (m, 1H), 2.29 (m, 1H), 1.88 (m, 2H), 1.31 (m, 2H).

MS m/z (+ESI): 491.6 [M+H]

Example 4

3-oxo-3,4-dihydro-2H-benzo[1,4]thiazine-6-carboxylic acid [1-(6-methoxy-3,4-dihydro-2H-1-oxa-9-aza-phenanthrene-3-yl)-1H-pyrazol-4-yl]-amide Preparation of (4-nitro-pyrazol-1-yl)-acetic acid Bromo-acetic acid (1.23 g, 8.84 mmol, 2.0 eq) is added at room temperature to a stirred solution of 4-nitro-1H-pyrazole (500 mg, 4.42 mmol, 1.0 eq) in tetrahydrofuran (50 mL), followed by potassium carbonate (6.15 g, 44.2 mmol, 10.0 eq). The reaction mixture is heated under reflux for 2 hours, solvent is then evaporated, the residue is extracted with ethyl acetate (3×40 mL) and water (40 mL), and the pH is adjusted to 4 by the addition of a 0.1N hydrochloric acid aqueous solution. The combined organic layers are dried over sodium sulfate, filtered and concentrated to afford (4-nitro-pyrazol-1-yl)-acetic acid as a light yellow solid (589 mg, 78% yield).

$^1$H-NMR (400 MHz, DMSO-d6) δ ppm: 13.30 (br, 1H), 8.85 (s, 1H), 8.27 (s, 1H), 5.04 (s, 2H).

MS m/z (+ESI): 172.2 $[M+H]^+$.

Preparation of 6-methoxy-3-(4-nitro-pyrazol-1-yl)-1-oxa-9-aza-phenanthren-2-one

Sodium hydrogen carbonate (4.96 g, 59.06 mmol, 3.0 eq) is added at room temperature to a stirred solution of (4-nitro-pyrazol-1-yl)-acetic acid (3.77 g, 21.65 mmol, 1.1 eq) and O-(7-azabenzotriazol-1-yl)-N,N,N',N'-tetramethyluronium hexafluorophosphate (14.97 g, 39.37 mmol, 2.0 eq) in N,N-dimethylformamide (200 mL). After 1 h30 stirring at room temperature 3-hydroxy-6-methoxy-quinoline-4-carbaldehyde (4.0 g, 19.69 mmol, 1.0 eq) is added and the resulting mixture is stirred at room temperature for 3 hours before the addition of 1,8-diazabicyclo[5,4,0]undec-7-ene (11.8 mL, 78.74 mmol, 4.0 eq). After 48 hours stirring at room temperature, the reaction mixture is poured into water (1000 mL) and the resulting solid is collected by filtration to afford 6-methoxy-3-(4-nitro-pyrazol-1-yl)-1-oxa-9-aza-phenanthren-2-one as a yellow solid (4.0 g, 57% yield).

$^1$H-NMR (400 MHz, DMSO-d6) δ ppm: 9.38 (s, 1H), 9.37 (s, 1H), 8.95 (s, 1H), 8.27 (s, 1H), 8.01 (d, J=8.8 Hz, 1H), 7.96 (m, 1H), 7.43 (s, 1H), 3.98 (s, 3H).

MS m/z (+ESI): 339.1 $[M+H]^+$.

Preparation of 4-[3-hydroxy-2-(4-nitro-pyrazol-1-yl)-propyl]-6-methoxy-quinolin-3-ol Sodium borohydride (179 mg, 4.73 mmol, 8.0 eq) is added at 0° C. to a stirred solution of 6-methoxy-3-(4-nitro-pyrazol-1-yl)-1-oxa-9-aza-phenanthren-2-one (200 mg, 0.59 mmol, 1.0 eq) in tetrahydrofuran (50 mL). After 2 hours stirring at 0° C., the reaction mixture is cautiously acidified to pH=1 with a 4N hydrochloric acid aqueous solution. Tetrahydrofuran is evaporated and the residue is extracted with ethyl acetate (3×40 mL). The combined organic layers are dried over sodium sulfate, filtered and concentrated to give a residue that is purified by column chromatography (silica gel, eluent: petroleum ethyl acetate:methanol, 20:1, v/v) to afford 4-[3-hydroxy-2-(4-nitro-pyrazol-1-yl)-propyl]-6-methoxy-quinolin-3-ol as a white solid (170 mg, 84% yield).

$^1$H-NMR (400 MHz, DMSO-d6) δ ppm: 8.90 (s, 1H), 8.39 (s, 1H), 8.16 (s, 1H), 7.72 (d, J=9.6 Hz, 1H), 7.07 (m, 2H), 4.60 (m, 1H), 3.91 (s, 3H), 3.43 (m, 2H), 2.06 (m, 2H).

MS m/z (−ESI): 343.0 $[M-H]^-$.

Preparation of 6-methoxy-3-(4-nitro-pyrazol-1-yl)-3,4-dihydro-2H-1-oxa-9-aza-phenanthrene Diethyl azodicarboxylate (250 μL, 1.87 mmol, 6.43 eq) is added at room temperature to a stirred solution of 4-[3-hydroxy-2-(4-nitro-pyrazol-1-yl)-propyl]-6-methoxy-quinolin-3-ol (100 mg, 0.29 mmol, 1.0 eq) and triphenylphosphine (122 mg, 0.46 mmol, 1.6 eq) in N,N-dimethylformamide (38 mL). After 3 hours stirring at room temperature, solvent is evaporated and the residue is extracted with ethyl acetate (3×20 mL) and water (20 mL). The combined organic layers are dried over sodium sulfate, filtered and concentrated to give a crude product that is purified by column chromatography (silica gel, eluent: petroleum ether:ethyl acetate, 1:1, v/v) to afford 6-methoxy-3-(4-nitro-pyrazol-1-yl)-3,4-dihydro-2H-1-oxa-9-aza-phenanthrene as a light yellow solid (60 mg, 63% yield).

$^1$H-NMR (400 MHz, DMSO-d6) δ ppm: 9.03 (s, 1H), 8.37 (s, 1H), 8.33 (s, 1H), 7.84 (d, J=8.8 Hz, 1H), 7.22 (m, 2H), 5.18 (m, 1H), 4.55 (d, J=6.4 Hz, 2H), 3.90 (s, 3H), 3.66 (d, J=5.2 Hz, 2H).

MS m/z (+ESI): 327.1 $[M+H]^+$.

Preparation of 1-(6-methoxy-3,4-dihydro-2H-1-oxa-9-aza-phenanthren-3-yl)-1H-pyrazol-4-olamine Ammonium chloride (4.0 g, 73.54 mmol, 6.0 eq) is added at room temperature to a stirred suspension of 6-methoxy-3-(4-nitro-pyrazol-1-yl)-3,4-dihydro-2H-1-oxa-9-aza-phenanthrene (4.0 g, 12.26 mmol, 1.0 eq) and iron powder (8.22 g, 147.10 mmol, 12.0 eq) in ethanol (600 mL). The resulting mixture is heated under reflux for 2 hours, then filtered through decalite, solvent is removed and the crude is extracted with ethyl acetate (3×200 mL) and water (200 mL). The combined organic layers are dried over sodium sulfate, filtered and concentrated to give a residue that is purified by column chromatography (silica gel, eluent: petroleum ether: ethyl acetate:methanol, 1:1:0 to 0:25:1, v/v/v) to afford 1-(6-methoxy-3,4-dihydro-2H-1-oxa-9-aza-phenanthren-3-yl)-1H-pyrazol-4-ylamine as a white solid (800 mg, 22% yield).

$^1$H-NMR (400 MHz, DMSO-d6) δ ppm: 8.36 (s, 1H), 7.83 (d, J=8.8 Hz, 1H), 7.20 (m, 2H), 7.10 (s, 1H), 6.95 (s, 1H), 4.83 (m, 1H), 4.33-4.45 (m, 2H), 3.82-3.93 (m, 5H), 3.52 (m, 2H).

MS m/z (+ESI): 297.2 [M+H]$^+$.

Preparation of 3-oxo-3,4-dihydro-2H-benzo[1,4]thiazine-6-carboxylic acid [1-(6-methoxy-3,4-dihydro-2H-1-oxa-9-aza-phenanthrene-3-yl)-1H-pyrazol-4-yl]-amide The titled compound is prepared as a white solid (95 mg, 58% yield) following Scheme 3 and in analogy to Example 1 using 1-(6-methoxy-3,4-dihydro-2H-1-oxa-9-aza-phenanthrene-3-yl)-1H-pyrazol-4-ylamine (100 mg, 0.34 mmol, 1.0 eq) and 3-oxo-3,4-dihydro-2H-benzo[1,4]thiazine-6-carboxylic acid (85 mg, 0.40 mmol, 1.2 eq) as starting materials.

$^1$H-NMR (400 MHz, Acetone-d6) δ ppm: 10.73 (s, 1H), 10.4 (s, 1H), 8.38 (s, 1H), 8.13 (s, 1H), 7.85 (d, J=8.8 Hz, 1H), 7.67 (s, 1H), 7.45 (m, 3H), 7.22 (m, 2H), 5.07 (m, 1H), 4.49 (s, 2H), 3.90 (s, 3H), 3.59 (m, 2H), 3.51 (m, 2H).

MS m/z (+ESI): 488.2 [M+H]$^+$.

Example 13

3-oxo-3,4-dihydro-2H-benzo[1,4]thiazine-6-carboxylic acid [1-(5-fluoro-6-methoxy-3,4-dihydro-2H-1-oxa-9-aza-phenanthren-3-yl)-piperidin-4-yl]-amide Preparation of 5,5-difluoro-3-hydroxy-6-oxo-5,6-dihydro-quinoline-4-carboxylic acid methyl ester 3-Hydroxy-6-methoxy-quinoline-4-carboxylic acid methyl ester (12.0 g, 51.45 mmol, 1.0 eq) is dissolved in concentrated sulfuric acid (82 mL, 1.54 mol, 30.0 eq). The solution is cooled to 0-10° C. and fluorine gas is bubbled into the reaction for 12 hours (100 mL/min). The reaction mixture is then poured into a mixture of sodium carbonate (163 g, 1.54 mol, 30.0 eq) and ice. The resulting mixture is extracted with ethyl acetate (3×60 mL). The combined organic layers are dried over sodium sulfate, filtered and concentrated to afford 5,5-difluoro-3-hydroxy-6-oxo-5,6-dihydro-quinoline-4-carboxylic acid methyl ester as an orange solid (11.0 g, 84% yield).

$^1$H-NMR (400 MHz, DMSO-d6) δ ppm: 8.41 (s, 1H), 7.67 (d, J=10.0 Hz, 1H), 6.37 (d, J=10.0 Hz, 1H), 3.84 (s, 3H).

MS m/z (+ESI): 256.0 [M+H]$^+$.

Preparation of 3-acetoxy-5,5-difluoro-6-oxo-5,6-dihydro-quinoline-4-carboxylic acid methyl ester A solution of 5,5-difluoro-3-hydroxy-6-oxo-5,6-dihydro-quinoline-4-carboxylic acid methyl ester (11.1 g, 43.50 mmol, 1.0 eq) in acetone (100 mL) is cooled to 0° C. before the addition of acetic anhydride (8.2 mL, 87.0 mmol, 2.0 eq). After 3 hours stirring at room temperature, solvent is evaporated and the crude product is purified by column chromatography (silica gel, eluent: petroleum ether:ethyl acetate, 5:1, v/v) to afford 3-acetoxy-5,5-difluoro-6-oxo-5,6-dihydro-quinoline-4-carboxylic acid methyl ester as a white solid (5.2 g, 40% yield).

$^1$H-NMR (400 MHz, DMSO-d6) δ ppm: 8.87 (s, 1H), 7.76 (d, J=10.0 Hz, 1H), 6.63 (d, J=10.0 Hz, 1H), 3.92 (s, 3H), 2.34 (s, 3H).

MS m/z (+ESI): 298.0 [M+H]$^+$.

Preparation of 3-acetoxy-5-fluoro-6-hydroxy-quinoline-4-carboxylic acid methyl ester 10% Palladium on activated carbon (178 mg, 0.17 mmol, 0.015 eq) is added at room temperature to a stirred solution of 3-acetoxy-5,5-difluoro-6-oxo-5,6-dihydro-quinoline-4-carboxylic acid methyl ester (2.27 g, 11.32 mmol, 1.0 eq) in methanol (50 mL). The resulting mixture is stirred under hydrogen flow (1 bar) at room temperature for 2 hours. The catalyst is then removed by filtration and the solution is concentrated to afford 3-acetoxy-5-fluoro-6-hydroxy-quinoline-4-carboxylic acid methyl ester as a light yellow semisolid (2.03 g, 95% yield) which is directly engaged in the next step.

$^1$H-NMR (400 MHz, MeOH-d4) δ ppm: 8.59 (s, 1H), 7.80 (d, J=9.2 Hz, 1H), 7.49 (t, J=9.2 Hz, 1H), 3.99 (s, 3H), 2.34 (s, 3H).

MS m/z (+ESI): 280.0 [M+H]$^+$.

Preparation of 3-acetoxy-5-fluoro-6-methoxy-quinoline-4-carboxylic acid methyl ester Methanol (0.52 mL, 12.72 mmol, 3.0 eq) is added at room temperature to a stirred solution of 3-acetoxy-5-fluoro-6-hydroxy-quinoline-4-carboxylic acid methyl ester (1.18 g, 4.24 mmol, 1.0 eq) in tetrahydrofuran (50 mL), followed by triphenylphosphine (2.22 g, 12.72 mmol, 3.0 eq) and diethyl azodicarboxylate (1.48 g, 12.72 mmol, 3.0 eq). After 3 hours stirring at room temperature, solvent is evaporated to give a crude product that is purified by column chromatography (silica gel, eluent: dichloromethane:methanol, 30:1, v/v) to afford 3-acetoxy-5-fluoro-6-methoxy-quinoline-4-carboxylic acid methyl ester as a yellow oil (0.81 g, 65% yield).

$^1$H-NMR (400 MHz, MeOH-d4) δ ppm: 8.68 (s, 1H), 7.95 (d, J=9.2 Hz, 1H), 7.80 (t, J=9.2 Hz, 1H), 4.04 (s, 3H), 3.99 (s, 3H), 2.34 (s, 3H).

MS m/z (+ESI): 294.0 [M+H]$^+$.

Preparation of 5-fluoro-4-hydroxymethyl-6-methoxy-quinolin-3-ol

3-Acetoxy-5-fluoro-6-methoxy-quinoline-4-carboxylic acid methyl ester (355 mg, 1.21 mmol, 1.0 eq) is added at 0° C. to a stirred suspension of lithium aluminium hydride (138 mg, 3.63 mmol, 3.0 eq) in tetrahydrofuran (5 mL). After 2 hours stirring at 0° C., brine is used to quench the reaction and the resulting mixture is extracted with ethyl acetate (3×10 mL). The combined organic layers are dried over sodium sulfate, filtered and concentrated to give a residue that is suspended in dichloromethane:methanol (10:1, v/v) and filtered to afford 5-fluoro-4-hydroxymethyl-6-methoxy-quinolin-3-ol as an off-white solid (62 mg, 23% yield).

$^1$H-NMR (400 MHz, MeOH-d4) δ ppm: 8.40 (s, 1H), 7.73 (d, J=9.2 Hz, 1H), 7.48 (t, J=9.2 Hz, 1H), 5.24 (s, 2H), 4.00 (s, 3H).

MS m/z (+ESI): 224.1 [M+H]$^+$.

Preparation of 5-fluoro-3-hydroxy-6-methoxy-quinoline-4-carbaldehyde

Manganese dioxide (299 mg, 4.3 mmol, 10.0 eq) is added at room temperature to a stirred solution of 5-fluoro-4-hydroxymethyl-6-methoxy-quinolin-3-ol (120 mg, 0.43 mmol, 1.0 eq) in acetone (12 mL) and the resulting mixture is stirred at 35° C. for 17 hours. The solid is filtered off, washed with acetone (3×10 mL) and the filtrate is concentrated to give a residue that is purified by column chromatography (silica gel, eluent: ethyl acetate:hexane, 1:3, v/v) to afford 5-fluoro-3-hydroxy-6-methoxy-quinoline-4-carbaldehyde as a yellow solid (40 mg, 42% yield).

$^1$H-NMR (400 MHz, DMSO-d6) δ ppm: 12.40 (s, 1H), 10.71 (s, 1H), 8.66 (s, 1H), 7.89 (d, J=9.2 Hz, 1H), 7.64 (t, J=9.2 Hz, 1H), 3.99 (s, 3H).

MS m/z (+ESI): 222.1 $[M+H]^+$.

Preparation of 3-oxo-3,4-dihydro-2H-benzo[1,4]thiazine-6-carboxylic acid [1-(5-fluoro-6-methoxy-3,4-dihydro-2H-1-oxa-9-aza-phenanthren-3-yl)-piperidin-4-yl]-amide The titled compound is prepared as a light brown solid following Scheme 1 and in analogy to Example 1 using 5-fluoro-3-hydroxy-6-methoxy-quinoline-4-carbaldehyde, piperidin-4-yl carbamic acid tert-butyl ester and 3-oxo-3,4-dihydro-2H-benzo[1,4]thiazine-6-carboxylic acid as starting materials.

$^1$H-NMR (400 MHz, DMSO-d6) δ ppm: 10.65 (s, 1H), 8.38 (s, 1H), 8.23 (d, J=7.7 Hz, 1H), 7.77 (dd, J=1.5, 9.2 Hz, 1H), 7.57 (t, J=9.0 Hz, 1H), 7.37-7.47 (m, 3H), 4.45 (m, 1H), 4.08 (m, 1H), 3.97 (s, 3H), 3.77 (m, 1H), 3.50 (s, 2H), 3.40 (m, 1H), 3.25 (m, 1H), 3.07 (m, 1H), 2.98 (m, 2H), 2.30-2.49 (m, 2H), 1.80 (m, 2H), 1.55 (m, 2H).

MS m/z (+ESI): 523.4 $[M+H]^+$.

Example 15

3-oxo-3,4-dihydro-2H-pyrido[3,2-b][1,4]thiazine-6-carboxylic acid [trans-4-(6-methoxy-3,4-dihydro-2H-1-oxa-9-aza-phenanthren-3-yl)-cyclohexyl]-amide Preparation of [trans-4-(2,4-dihydro-6-methoxy-3,4-dihydro-2H-1-oxa-9-aza-phenanthren-3-yl)-cyclohexyl]-carbamic acid tert-butyl ester A solution of [trans-4-(2-oxo-ethyl)-cyclohexyl]-carbamic acid tert-butyl ester (1.80 g, 8.86 mmol, 1.0 eq), 3-hydroxy-6-methoxy-quinoline-4-carbaldehyde (2.14 g, 8.86 mmol, 1.0 eq) and L-proline (408 mg, 3.54 mmol, 0.04 eq) in dimethyl sulfoxide (23 mL) and water (2.3 mL) is stirred at room temperature for 14 hours. The reaction mixture is then extracted with dichloromethane (230 mL) and water (230 mL). The organic layer is washed with brine (230 mL), dried over magnesium sulfate, filtered and concentrated to give a residue that is purified by column chromatography (silica gel, eluent: dichloromethane:methanol, 25:1, v/v) to afford [trans-4-(2,4-dihydro-6-methoxy-3,4-dihydro-2H-1-oxa-9-aza-phenanthren-3-yl)-cyclohexyl]-carbamic acid tert-butyl ester as a light yellow solid (2.80 g, 71% yield).

MS m/z (+ESI): 445.2 $[M+H]^+$.

Preparation of acetic acid 4-acetoxy-3-(trans-4-tert-butoxycarbonylamino-cyclohexyl)-6-methoxy-3,4-dihydro-2H-1-oxa-9-aza-phenanthren-2-yl ester Acetic anhydride (5.3 mL, 56.2 mmol, 10.1 eq) is added at room temperature to a stirred solution of [trans-4-(2,4-dihydro-6-methoxy-3,4-dihydro-2H-1-oxa-9-aza-phenanthren-3-yl)-cyclohexyl]-carbamic acid tert-butyl ester (2.5 g, 5.55 mmol, 1.0 eq) in pyridine (50 mL) and the resulting mixture is stirred at 50° C. for 14 hours. Pyridine is removed under reduced pressure, the crude is dissolved in ethyl acetate (100 mL) and the resulting solution is successively washed with a saturated sodium hydrogen carbonate aqueous solution (2×100 mL), a 1N hydrochloric acid aqueous solution (2×100 mL) and brine (100 mL). The organic layer is dried over magnesium sulfate, filtered and concentrated to afford the crude product as a yellow semisolid that is purified by column chromatography (silica gel, eluent: dichloromethane:methanol, 25:1, v/v) to afford acetic acid 4-acetoxy-3-(trans-4-tert-butoxycarbonylamino-cyclohexyl)-6-methoxy-3,4-dihydro-2H-1-oxa-9-aza-phenanthren-2-yl ester as a light yellow solid (2.3 g, 77% yield).

MS m/z (+ESI): 529.2 $[M+H]^+$.

Preparation of acetic acid 3-(trans-4-tert-butoxycarbonylamino-cyclohexyl)-6-methoxy-3,4-dihydro-2H-1-oxa-9-aza-phenanthren-2-yl ester 10% Palladium on activated carbon (500 mg, 4.70 mmol, 1.09 eq) is added at room temperature to a stirred solution of acetic acid 4-acetoxy-3-(trans-4-tert-butoxycarbonylamino-cyclohexyl)-6-methoxy-3,4-dihydro-2H-1-oxa-9-aza-phenanthren-2-yl ester (2.3 g, 4.29 mmol, 1.0 eq) in methanol (60 mL). The reaction mixture is stirred at room temperature under hydrogen flow (10 bars) for 72 hours. The catalyst is then removed by filtration and the solution is concentrated to afford acetic acid 3-(trans-4-tert-butoxycarbonylamino-cyclohexyl)-6-methoxy-3,4-dihydro-2H-1-oxa-9-aza-phenanthren-2-yl ester as a yellow semisolid (1.45 g, 71% yield) which is directly engaged in the next step.

MS m/z (+ESI): 471.1 $[M+H]^+$.

Preparation of {trans-4-[2-hydroxy-1-(3-hydroxy-6-methoxy-quinolin-4-ylmethyl)-ethyl]-cyclohexyl}-carbamic acid tert-butyl ester Sodium borohydride (920 mg, 24.2 mmol, 6.0 eq) is added at room temperature to a stirred solution of acetic acid 3-(trans-4-tert-butoxycarbonylamino-cyclohexyl)-6-methoxy-3,4-dihydro-2H-1-oxa-9-aza-phenanthren-2-yl ester (1.90 g, 4.04 mmol, 1.0 eq) in ethanol (120 mL). After 1 hour stirring at room temperature, the reaction mixture is acidified with a 1N hydrochloric acid aqueous solution to pH 4. Solvent is evaporated and the residue is purified by column chromatography (silica gel, eluent: dichloromethane:methanol, 25:1 to 15:1, v/v) to afford {trans-4-[2-hydroxy-1-(3-hydroxy-6-methoxy-quinolin-4-ylmethyl)-ethyl]-cyclohexyl}-carbamic acid tert-butyl ester as a white solid (1.26 g, 65% yield).

1H NMR (400 MHz, DMSO-d6), δ (ppm): 8.34 (s, 1H), 7.74 (m, 1H), 7.24 (s, 1H), 7.10 (m, 1H), 6.73 (m, 1H), 3.83 (s, 3H), 3.56 (m, 1H), 3.23, 3.32 (2m, 2H), 2.84, 2.94 (2m, 2H), 1.34-1.71 (4m, 10H), 1.34 (s, 9H).

MS m/z (+ESI): 431.3 $[M+H]^+$.

Preparation of [trans-4-(6-methoxy-3,4-dihydro-2H-1-oxa-9-aza-phenanthren-3-yl)-cyclohexyl]-carbamic acid tert-butyl ester Diisopropylazodicarboxylate (0.76 g, 3.80 mmol, 1.7 eq) is added at room temperature to a stirred solution of {trans-4-[2-hydroxy-1-(3-hydroxy-6-methoxy-quinolin-4-ylm-ethyl)-ethyl]-cyclohexyl}-carbamic acid tert-butyl ester (1.08 g, 2.26 mmol, 1.0 eq) and triphenylphosphine (1.90 g, 7.53 mmol, 3.33 eq) in tetrahydrofuran (120 mL). After 1 hour stirring at room temperature, solvent is evaporated to give a crude product that is purified by preparative HPLC to afford [trans-4-(6-methoxy-3,4-dihydro-2H-1-oxa-9-aza-phenanthren-3-yl)-cyclohexyl]-carbamic acid tert-butyl ester as a white lyophilizated powder (670 mg, 71% yield).

1H NMR (400 MHz, DMSO-d6), δ (ppm): 8.29 (s, 1H), 7.79 (d, J=10.0 Hz, 1H), 7.17 (m, 2H), 6.67 (d, J=8.4 Hz, 1H), 3.90 (s, 3H), 3.84, 4.38 (2m, 2H), 3.20 (m, 1H), 2.72, 3.05 (2m, 2H), 1.36 (s, 9H), 1.15-1.20, 1.82-1.84 (2m, 10H).

MS m/z (+ESI): 413.4 $[M+H]^+$.

Preparation of 3-oxo-3,4-dihydro-2H-pyrido[3,2-b][1,4]thiazine-6-carboxylic acid [trans-4-(6-methoxy-3,4-dihydro-2H-1-oxa-9-aza-phenanthren-3-yl)-cyclohexyl]-amide The titled compound is prepared as a white lyophilizated powder following Scheme 6 and in analogy to Example 1 using [trans-4-(6-methoxy-3,4-dihydro-2H-1-oxa-9-aza-phenanthren-3-yl)-cyclohexyl]-carbamic acid tert-butyl ester and 3-oxo-3,4-dihydro-2H-pyrido[3,2-b][1,4]thiazine-6-carboxylic acid as starting materials.

$^1$H-NMR (400 MHz, DMSO-d6) δ ppm: 10.99 (s, 1H), 8.33 (s, 1H), 7.96 (d, J=7.9 Hz, 2H), 7.82 (d, J=8.9 Hz, 1H), 7.60 (d, J=7.9 Hz, 1H), 7.21 (s, 1H), 7.19 (s, 1H), 4.44 (m, 1H), 3.93 (s, 3H), 3.86 (m, 1H), 3.76 (m, 1H), 3.63 (s, 2H), 3.12 (m, 1H), 2.76 (m, 1H), 1.83-2.10 (m, 5H), 1.20-1.48 (m, 5H).

MS m/z (+ESI): 505.2 $[M+H]^+$.

Example 20

[1-(6-methoxy-3,4-dihydro-2H-1-oxa-9-aza-phenanthren-3-yl)-1H-pyrazol-4-yl]-[2-(thiophen-2-ylsulfanyl)-ethyl]-amine Preparation of 2-(2-bromo-ethylsulfanyl)-thiophene Potassium carbonate (2.50 g, 18.07 mmol, 2.1 eq) is added at room temperature to a stirred solution of thiophene-2-thiol (813 μL, 8.61 mmol, 1.0 eq) in 1,2-dibromoethane (10 mL) and the resulting mixture is stirred at 78° C. for 3 hours. Then potassium carbonate is removed by filtration and the mother liquid is concentrated to give a crude that is purified by column chromatography (silica gel, eluent: cyclohexane 100%) to afford 2-(2-bromo-ethylsulfanyl)-thiophene as a light yellow oil (1.86 g, 95% yield).

$^1$H-NMR (400 MHz, DMSO-d6) δ ppm: 7.68 (dd, J=1.2, 5.3 Hz, 1H), 7.27 (dd, J=1.2, 3.5 Hz, 1H), 7.09 (dd, J=3.5, 5.3 Hz, 1H), 3.56 (m, 2H), 3.19 (m, 2H).

Preparation of [1-(6-methoxy-3,4-dihydro-2H-1-oxa-9-aza-phenanthren-3-yl)-1H-pyrazol-4-yl]-[2-(thiophen-2-ylsulfanyl)-ethyl]-amine 2-(2-Bromo-ethylsulfanyl)-thiophene (317 mg, 0.13 mmol, 1.0 eq) is added at room temperature to a stirred solution of 1-(6-methoxy-3,4-dihydro-2H-1-oxa-9-aza-phenanthren-3-yl)-1H-pyrazol-4-ylamine (50 mg, 0.13 mmol, 1.0 eq) in acetonitrile (6 mL), followed by triethylamine (19 μL, 0.13 mmol, 1.0 eq). After 72 hours stirring at 80° C., the reaction mixture is concentrated to give a residue that is purified by column chromatography (silica gel, eluent: cyclohexane:ethyl acetate:methanol, 1:3:0 to 0:1:0 to 0:9:1, v/v/v) to afford [1-(6-methoxy-3,4-dihydro-2H-1-oxa-9-aza-phenanthren-3-yl)-1H pyrazol-4-yl]-[2-(thiophen-2-ylsulfanyl)-ethyl]-amine as a brown viscous oil (9 mg, 14% yield).

$^1$H-NMR (400 MHz, DMSO-d6) δ ppm: 8.38 (s, 1H), 7.86 (d, J=9.0 Hz, 1H), 7.60 (dd, J=1.3, 5.3 Hz, 1H), 7.22 (m, 4H), 7.03 (m, 2H), 4.85 (m, 1H), 4.52 (m, 1H), 4.47 (m, 1H), 4.36 (m, 1H), 3.92 (s, 3H), 3.54 (m, 2H), 3.03 (m, 2H), 2.91 (m, 2H).

MS m/z (+ESI): 439.4 $[M+H]^+$.

Example 27

3-oxo-3,4-dihydro-2H-benzo[1,4]thiazine-6-carboxylic acid [6-(6-methoxy-4-methyl-3,4-dihydro-2H-1-oxa-4,5,9-triaza-phenanthren-3-yl)-pyridin-3-yl]-amide Preparation of 7,8-dibromo-2-methoxy-[1,5]naphthyridine Phosphorus tribromide (140 mg, 0.53 mmol, 1.3 eq) is added at 0° C. to a stirred suspension of 3-bromo-6-methoxy-[1,5]naphthyridin-4-ol (100 mg, 0.39 mmol, 1.0 eq) in N,N-dimethylformamide (1 mL). After 2 hours stirring at room temperature, the reaction mixture is poured into saturated sodium carbonate aqueous solution (50 mL). The resulting suspension is filtered and the cake is washed with water and methanol to afford 7,8-dibromo-2-methoxy-[1,5]naphthyridine as a white solid (100 mg, 80% yield).

$^1$H-NMR (400 MHz, DMSO-d6) δ ppm: 8.89 (s, 1H), 8.30 (d, J=8.8 Hz, 1H), 7.34 (d, J=8.8 Hz, 1H), 4.06 (s, 3H).

Preparation of benzyl-(3-bromo-6-methoxy-[1,5]naphthyridin-4-yl)-amine

Benzylamine (67 mg, 0.63 mmol, 2.0 eq) is added at room temperature to a stirred solution of 7,8-dibromo-2-methoxy-[1,5]naphthyridine (100 mg, 0.31 mmol, 1.0 eq) in N,N-dimethylformamide (10 mL), followed by potassium carbonate (87 mg, 0.63 mmol, 2.0 eq). After 2 hours stirring at 120° C., solvent is removed and the residue is extracted with ethyl acetate (3×10 mL) and water (10 mL). The combined organic layers are dried over sodium sulfate, filtered and concentrated to give the crude product that is purified by column chromatography (silica gel, eluent: petroleum ether:ethyl acetate, 5:1, v/v) to afford benzyl-(3-bromo-6-methoxy-[1,5]naphthyridin-4-yl)-amine as a light yellow solid (50 mg, 46% yield).

$^1$H-NMR (400 MHz, DMSO-d6) δ ppm: 8.52 (s, 1H), 8.11 (d, J=8.8 Hz, 1H), 7.22-7.38 (m, 5H), 7.07 (d, J=8.8 Hz, 1H), 6.25 (br, 1H), 5.30 (d, J=6.0 Hz, 2H), 3.90 (s, 3H).

MS m/z (+ESI): 344.0/346.0 $[M+H]^+$.

Preparation of 4-benzylamino-6-methoxy-[1,5]naphthyridin-3-ol

Tris(dibenzylideneacetone)dipalladium(0) (10 mg, 0.011 mmol, 0.04 eq) is added at room temperature to a stirred solution of benzyl-(3-bromo-6-methoxy-[1,5]naphthyridin-4-yl)-amine (100 mg, 0.29 mmol, 1.0 eq) in dioxane (6 mL)

and water (3 mL), followed by (4',6'-diisopropyl-3,4,5,6,2'-pentamethyl-biphenyl-2-yl)-dimethyl-phosphane (8 mg, 0.016 mmol, 0.06 eq). After 10 minutes stirring at room temperature, a solution of potassium hydroxide (82 mg, 1.46 mmol, 5.0 eq) in water (3 mL) is added and the resulting mixture is stirred at 105° C. for 16 hours. The reaction mixture is cooled down to room temperature, extracted with ethyl acetate (3×10 mL) and water (10 mL) and the pH is adjusted to 6 by the addition of a 1N hydrochloric acid aqueous solution. The combined organic layers are dried over sodium sulfate, filtered and concentrated to give the crude product that is purified by column chromatography (silica gel, eluent: dichloromethane:methanol, 5:1, v/v) to afford 4-benzylamino-6-methoxy-[1,5]naphthyridin-3-ol as a light yellow solid (30 mg, 36% yield).

$^1$H-NMR (400 MHz, DMSO-d6) δ ppm: 9.68 (br, 1H), 8.14 (s, 1H), 7.95 (d, J=8.8 Hz, 1H), 7.15-7.28 (m, 5H), 6.93 (d, J=8.8 Hz, 1H), 6.42 (t, J=3.2 Hz, 1H), 4.99 (d, J=3.2 Hz, 2H), 3.93 (s, 3H).

MS m/z (+ESI): 282.1 $[M+H]^+$.

Preparation of 4-amino-6-methoxy-[1,5]naphthyridin-3-ol

A suspension of 4-benzylamino-6-methoxy-[1,5]naphthyridin-3-ol (50 mg, 0.18 mmol, 1.0 eq) and 70% palladium hydroxide (18 mg, 0.09 mmol, 0.5 eq) in methanol (3 mL) is stirred at room temperature under hydrogen flow (10 bars) for 72 hours. The catalyst is then removed by filtration and the solution is concentrated to afford 4-amino-6-methoxy-[1,5]naphthyridin-3-ol as a grey solid (20 mg, 59% yield) which is directly engaged in the next step.

$^1$H-NMR (400 MHz, $CDCl_3$) δ ppm: 8.04 (s, 1H), 7.93 (d, J=8.8 Hz, 1H), 6.96 (d, J=8.8 Hz, 1H), 4.57 (br, 2H), 4.06 (s, 3H).

MS m/z (+ESI): 192.1 $[M+H]^+$.

Preparation of [6-(2-bromo-acetyl)-pyridin-3-yl]-carbamic acid tert-butyl ester

Aluminium chloride (55 mg, 0.42 mmol, 0.1 eq) is added at 0° C. to a stirred solution of 6-(acetyl-pyridin-3-yl)-carbamic acid tert-butyl ester (1.0 g, 4.23 mmol, 1.0 eq) in tetrahydroduran (50 mL). After 30 minutes stirring at 0° C., bromine (406 mg, 2.54 mmol, 0.7 eq) is added dropwise at 0° C. over 2.5 hours. After 2.5 hours stirring at 0° C. the reaction mixture is quenched with a saturated sodium hydrogen carbonate aqueous solution. Tetrahydrofuran is then removed and the aqueous layer is extracted with ethyl acetate (3×30 mL). The combined organic layers are washed with brine, dried over sodium sulfate, filtered and concentrated to give the crude product that is purified by column chromatography (silica gel, eluent: petroleum ether:ethyl acetate, 100:1 to 20:1, v/v) to afford [6-(2-bromo-acetyl)-pyridin-3-yl]-carbamic acid tert-butyl ester as a light yellow solid (235 mg, 14% yield).

$^1$H-NMR (400 MHz, $CDCl_3$) δ ppm: 8.48 (s, 1H), 8.08 (m, 2H), 6.80 (s, 1H), 4.79 (s, 2H), 1.54 (s, 9H).

MS m/z (+ESI): 315.3/317.3 $[M+H]^+$.

Preparation of {6-[2-(4-amino-6-methoxy-[1,5]naphthyridin-3-yloxy)-acetyl]-pyridin-3-yl}-carbamic acid tert-butyl ester Potassium carbonate (140 mg, 1.02 mmol, 1.5 eq) is added at room temperature to a stirred solution of [6-(2-bromo-acetyl)-pyridin-3-yl]-carbamic acid tert-butyl ester (220 mg, 0.70 mmol, 1.0 eq) and 4-amino-6-methoxy-[1,5]naphthyridin-3-ol (130 mg, 0.69 mmol, 1.0 eq) in N,N-dimethylformamide (10 mL). After 30 minutes stirring at room temperature, solvent is removed and the residue is extracted with ethyl acetate (3×15 mL) and water (10 mL). The combined organic layers are washed with brine, dried over sodium sulfate, filtered and concentrated to give the crude product that is purified by column chromatography (silica gel, eluent: dichloromethane:methanol, 100:1, v/v) to afford {6-[2-(4-amino-6-methoxy-[1,5]naphthyridin-3-yloxy)-acetyl]-pyridin-3-yl}-carbamic acid tert-butyl ester as a red-brown solid (90 mg, 24% yield).

$^1$H-NMR (400 MHz, $CDCl_3$) δ ppm: 8.53 (s, 1H), 8.43 (s, 1H), 8.09 (d, J=8.4 Hz, 1H), 8.05 (d, J=9.2 Hz, 1H), 7.59 (d, J=8.4 Hz, 1H), 6.96 (d, J=9.2 Hz, 1H), 6.73 (s, 1H), 6.42 (s, 1H), 4.25 (d, J=10.4 Hz, 1H), 4.12 (d, J=10.4 Hz, 1H), 4.00 (s, 3H), 1.54 (s, 9H).

MS m/z (+ESI): 426.4 $[M+H]^+$.

Preparation of [6-(6-methoxy-3,4-dihydro-2H-1-oxa-4,5,9-triaza-phenanthren-3-yl)-pyridin-3-yl]-carbamic acid tert-butyl ester Acetic acid (110 mg, 1.83 mmol, 1.7 eq) is added at room temperature to a stirred solution of {6-[2-(4-amino-6-methoxy-[1,5]naphthyridin-3-yloxy)-acetyl]-pyridin-3-yl}-carbamic acid tert-butyl ester (470 mg, 1.10 mmol 1.0 eq) in methanol (20 mL) and the resulting mixture is stirred at room temperature for 1 hour before the addition of sodium cyanoborohydride (370 mg, 5.89 mmol, 5.3 eq). After 4 hours stirring at room temperature, the reaction mixture is extracted with dichloromethane (3×10 mL) and a saturated sodium hydrogen carbonate aqueous solution (10 mL). The combined organic layers are dried over sodium sulfate, filtered and concentrated to give a residue that is purified by column chromatography (silica gel, eluent: dichloromethane:methanol, 200:1 to 50:1, v/v) to afford [6-(6-methoxy-3,4-dihydro-2H-1-oxa-4,5,9-triaza-phenanthren-3-yl)-pyridin-3-yl]-carbamic acid tert-butyl ester as a light yellow solid (222 mg, 49% yield).

$^1$H-NMR (400 MHz, $CDCl_3$) δ ppm: 8.56 (s, 1H), 8.24 (d, J=8.4 Hz, 1H), 8.10 (s, 1H), 7.98 (d, J=9.2 Hz, 1H), 7.44 (s, 1H), 7.32 (d, J=8.4 Hz, 1H), 7.15 (d, J=9.2 Hz, 1H), 6.79 (s, 1H), 5.02 (m, 1H), 4.60 (d, J=10.8 Hz, 1H), 4.23 (d, J=10.8 Hz, 1H), 4.08 (s, 3H), 1.52 (s, 9H).

MS m/z (+ESI): 410.3 $[M+H]^+$.

Preparation of [6-(6-methoxy-4-methyl-3,4-dihydro-2H-1-oxa-4,5,9-triaza-phenanthren-3-yl)-pyridin-3-yl]-carbamic acid tert-butyl ester Methyl iodide (10.5 μL, 0.17 mmol, 1.0 eq) is added at room temperature to a stirred solution of [6-(6-methoxy-3,4-dihydro-2H-1-oxa-4,5,9-triaza-phenanthren-3-yl)-pyridin-3-yl]-carbamic acid tert-butyl ester (70 mg, 0.17 mmol, 1.0 eq) in N,N-dimethylformamide (4 mL), followed by cesium carbonate (55 mg, 0.17 mmol, 1.0 eq). After 4 hours stirring at room temperature, solvent is evaporated and the residue is extracted with dichloromethane (3×10 mL) and water (10 mL). The combined organic layers are dried over sodium sulfate, filtered and concentrated to afford [6-(6-methoxy-4-methyl-3,4-dihydro-2H-1-oxa-4,5,9-triaza-phenanthren-3-yl)-pyridin-3-yl]-carbamic acid tert-butyl ester as an orange viscous oil (89 mg, 75% yield) that is directly engaged in the next step.

MS m/z (+ESI): 424.2 $[M+H]^+$.

Preparation of 3-oxo-3,4-dihydro-2H-benzo[1,4]thiazine-6-carboxylic acid [6-(6-methoxy-4-methyl-3,4-dihydro-2H-1-oxa-4,5,9-triaza-phenanthren-3-yl)-pyridin-3-yl]-amide The titled compound is prepared as a light yellow lyophilizated powder following Scheme 5 and in analogy to Example 1 using [6-(6-methoxy-4-methyl-3,4-dihydro-2H-1-oxa-4,5,9-triaza-phenanthren-3-yl)-pyridin-3-yl]-carbamic acid tert-butyl ester and 3-oxo-3,4-dihydro-2H-benzo[1,4]thiazine-6-carboxylic acid acid as starting materials.

$^1$H-NMR (400 MHz, DMSO-d6) δ ppm: 10.97 (br, 1H), 10.86 (br, 1H), 8.97 (s, 1H), 8.54 (br, 1H), 8.46 (d, J=9.6 Hz, 1H), 8.23 (dd, J=2.5, 8.5 Hz, 1H), 7.88 (br, 1H), 7.62 (dd, J=1.8, 8.1 Hz, 1H), 7.49 (t, J=8.1 Hz, 2H), 7.39 (d, J=8.6 Hz, 1H), 5.17 (br, 1H), 4.57 (m, 1H), 4.39 (m, 1H), 4.13 (s, 3H), 4.12 (s, 3H), 3.53 (s, 2H).

MS m/z (+ESI): 515.1 $[M+H]^+$.

Example 35

3-oxo-3,4-dihydro-2H-benzo[1,4]oxazine-6-carboxylic acid [trans-4-(6-methoxy-3,4-dihydro-2H-1-oxa-4,5,9-triaza-phenanthren-3-yl)-cyclohexyl]-amide Preparation of [trans-4-(methoxy-methyl-carbamoyl)-cyclohexyl]-carbamic acid benzyl ester N,O-dimethyl-hydroxylamine hydrochloride (10 mg, 0.10 mmol, 1.2 equivalent) is added at room temperature to a stirred solution of trans-4-benzyloxycarbonylamino-cyclohexanecarboxylic acid (23 mg, 0.08 mmol, 1.0 eq) in N,N-dimethylformamide (5 mL), followed by O-(7-azabenzotriazol-1-yl)-N,N,N',N'-tetramethyluronium hexafluorophosphate (63 mg, 0.16 mmol, 2.0 eq) and sodium hydrogen carbonate (15 mg, 0.18 mmol, 2.2 eq). After 12 hours stirring at room temperature, solvent is evaporated and the residue is extracted with ethyl acetate (3×10 mL) and a saturated ammonium chloride aqueous solution (10 mL). The combined organic layers are dried over sodium sulfate, filtered and concentrated to give a residue that is purified by column chromatography (silica gel, eluent: petroleum ether: ethyl acetate, 2:1, v/v) to afford [trans-4-(methoxy-methyl-carbamoyl)-cyclohexyl]-carbamic acid benzyl ester as a colorless solid (8 mg, 30% yield).

$^1$H-NMR (400 MHz, DMSO-d6) δ ppm: 7.27-7.37 (m, 5H), 7.18 (d, J=7.6 Hz, 1H), 4.98 (s, 2H), 3.64 (s, 3H), 3.22 (m, 1H), 3.05 (s, 3H), 2.53 (m, 1H), 1.12-1.90 (m, 8H).

MS m/z (+ESI): 321.1 $[M+H]^+$.

Preparation of (trans-4-acetyl-cyclohexyl)-carbamic acid benzyl ester

Methylmagnesium chloride (3M solution in tetrahydrofuran, 31 mg, 0.41 mmol, 2.2 eq) is added at −10° C. to a stirred solution of [trans-4-(methoxy-methyl-carbamoyl)-cyclohexyl]-carbamic acid benzyl ester (60 mg, 0.19 mmol, 1.0 eq) in tetrahydrofuran (5 mL). After 3 hours stirring at −10° C., solvent is evaporated and the residue is extracted with ethyl acetate (3×10 mL) and a saturated ammonium chloride aqueous solution (10 mL). The combined organic layers are dried over sodium sulfate, filtered and concentrated to give a residue that is purified by column chromatography (silica gel, eluent: petroleum ether:ethyl acetate, 2:1, v/v) to afford (trans-4-acetyl-cyclohexyl)-carbamic acid benzyl ester as a white solid (20 mg, 39% yield).

$^1$H-NMR (400 MHz, $CDCl_3$) δ ppm: 7.27-7.38 (m, 5H), 5.09 (s, 2H), 4.59 (br, 1H), 3.42-3.55 (m, 1H), 2.27 (t, J=12.0 Hz, 1H), 2.14 (s, 3H), 1.11-2.14 (m, 8H).

MS m/z (+ESI): 276.1 $[M+H]^+$.

Preparation of [trans-4-(2-bromo-acetyl)-cyclohexyl]-carbamic acid benzyl ester

Bromine (160 μL, 3.12 mmol, 1.0 eq) is added at 10° C. to a stirred solution of (trans-4-acetyl-cyclohexyl)-carbamic acid benzyl ester (850 mg, 3.12 mmol, 1.0 eq) in methanol (30 mL). After 4 hours stirring at 10° C., the reaction mixture is diluted with petroleum ether (15 mL) and the resulting precipitate is collected by filtration to afford [trans-4-(2-bromo-acetyl)-cyclohexyl]-carbamic acid benzyl ester as a white solid (920 mg, 83% yield).

$^1$H-NMR (400 MHz, $CDCl_3$) δ ppm: 7.26-7.39 (m, 5H), 5.09 (s, 2H), 4.60 (br, 1H), 3.94 (s, 2H), 3.48 (m, 1H), 2.69 (t, J=12.0 Hz, 1H), 1.13-2.14 (m, 8H).

MS m/z (+ESI): 354.3/356.3 $[M+H]^+$.

Preparation of [trans-4-(3-hydroxy-6-methoxy-3,4-dihydro-2H-1-oxa-4,5,9-triaza-phenanthren-3-yl)-cyclohexyl]-carbamic acid benzyl ester Potassium carbonate (246 mg, 1.78 mmol, 2.0 eq) is added at room temperature to a stirred solution of 4-amino-6-methoxy-[1,5]naphthyridin-3-ol (170 mg, 0.89 mmol, 1.0 eq) in N,N-dimethylformamide (20 mL), followed by [trans-4-(2-bromo-acetyl)-cyclohexyl]-carbamic acid benzyl ester (315 mg, 0.89 mmol, 1.0 eq). After 4 hours stirring at room temperature, solvent is evaporated and the residue is extracted with ethyl acetate (3×20 mL) and a saturated ammonium chloride aqueous solution (20 mL). The combined organic layers are dried over sodium sulfate, filtered and concentrated to afford [trans-4-(3-hydroxy-6-methoxy-3,4-dihydro-2H-1-oxa-4,5,9-triaza-phenanthren-3-yl)-cyclohexyl]-carbamic acid benzyl ester (2.33 g, 88% Yield).

$^1$H-NMR (400 MHz, $CDCl_3$) δ ppm: 8.07 (s, 1H), 7.94 (d, J=8.8 Hz, 1H), 7.26-7.38 (m, 5H), 6.83 (d, J=8.8 Hz, 1H), 5.99 (s, 1H), 5.08 (s, 2H), 4.72 (br, 1H), 4.21 and 3.90 (2d, J=10.4 Hz, 2H, AB system), 3.97 (s, 3H), 3.42-3.58 (m, 1H), 1.12-2.20 (m, 9H).

MS m/z (+ESI): 465.5 $[M+H]^+$.

Preparation of [trans-4-(6-methoxy-3,4-dihydro-2H-1-oxa-4,5,9-triaza-phenanthren-3-yl)-cyclohexyl]-carbamic acid benzyl ester Acetic acid (10 μL, 0.17 mmol, 5.4 eq) is added at room temperature to a stirred solution of [trans-4-(3-hydroxy-6-methoxy-3,4-dihydro-2H-1-oxa-4,5,9-triaza-phenanthren-3-yl)-cyclohexyl]-carbamic acid benzyl ester (15 mg, 0.03 mmol, 1.0 eq) in dichloromethane (3 mL) and methanol (3 mL), followed by sodium cyanoborohydride (10 mg, 0.16 mmol, 5.0 eq). After 30 minutes stirring at room temperature, the reaction mixture is extracted with ethyl acetate (3×10 mL) and a saturated ammonium chloride aqueous solution (10 mL). The combined organic layers are dried over sodium sulfate, filtered and concentrated to give a residue that is purified by column chromatography (silica gel, eluent: dichloromethane:methanol, 10:1, v/v) to afford [trans-4-(6- methoxy-3,4-dihydro-2H-1-oxa-4,5,9-triaza-phenanthren-3-yl)-cyclohexyl]-carbamic acid benzyl ester as a white solid (11 mg, 76% yield).

$^1$H-NMR (400 MHz, $CDCl_3$) δ ppm: 8.27 (s, 1H), 8.08 (d, J=8.8 Hz, 1H), 7.29-7.38 (m, 5H), 6.96 (d, J=8.8 Hz, 1H), 5.78 (br, 1H), 5.09 (s, 2H), 4.58 (br, 1H), 4.24 (m, 2H), 4.05 (s, 3H), 3.46-3.55 (m, 1H), 3.36 (m, 1H), 0.82-2.18 (m, 9H).

MS m/z (+ESI): 449.1 $[M+H]^+$.

Preparation of trans-4-(6-methoxy-3,4-dihydro-2H-1-oxa-4,5,9-triaza-phenanthren-3-yl)-cyclohexylamine 10% Palladium on activated carbon (285 mg, 2.68 mmol, 1.0 eq) is added at room temperature to a stirred solution of [trans-4-(6-methoxy-3,4-dihydro-2H-1-oxa-4,5,9-triaza-phenanthren-3-yl)-cyclohexyl]-carbamic acid benzyl ester (1.20 g, 2.68 mmol, 1.0 eq) in methanol (80 mL) and tetrahydrofuran (8 mL). The resulting mixture is stirred under hydrogen flow (1 bar) at 40° C. for 16 hours. The catalyst is then removed by filtration and the solution is concentrated to afford trans-4-(6-methoxy-3,4-dihydro-2H-1-oxa-4,5,9-triaza-phenanthren-3-yl)-cyclohexylamine as a yellow solid (620 mg, 74% yield) which is directly engaged in the next step.

MS m/z (+ESI): 315.2 $[M+H]^+$.

Preparation of 3-oxo-3,4-dihydro-2H-benzo[1,4]oxazine-6-carboxylic acid [trans-4-(6-methoxy-3,4-dihydro-2H-1-oxa-4,5,9-triaza-phenanthren-3-yl)-cyclohexyl]-amide The titled compound is prepared as an off-white solid following Scheme 5 and in analogy to Example 27 using trans-4-(6-methoxy-3,4-dihydro-2H-1-oxa-4,5,9-triaza-phenanthren-3-yl)-cyclohexylamine and 3-oxo-3,4-dihydro-2H-benzo[1,4]oxazine-6-carboxylic acid as starting materials.

MS m/z (+ESI): 490.4 $[M+H]^+$.

Example 37

3-oxo-3,4-dihydro-2H-benzo[1,4]oxazine-6-carboxylic acid [4-(6-methoxy-3,4-dihydro-2H-1-oxa-5,9-diaza-phenanthren-3-yl)-cyclohexyl]-amide Preparation of 3-chloro-6-methoxy-[1,5]naphthyridine-4-carbonitrile Copper(I) cyanide (39.3 g, 0.44 mol, 1.2 eq) is added at room temperature to a stirred solution of 8-bromo-7-chloro-2-methoxy-[1,5]naphthyridine (100 g, 0.37 mol, 1.0 eq) in N,N-dimethylformamide (1.5 L). After 8 hours stirring at 130° C., the reaction mixture is cooled down to room temperature and treated with a saturated ammonium chloride aqueous solution (1.5 L). The aqueous layer is separated and extracted with ethyl acetate (2×1.5 L). The combined organic layers are dried over sodium sulfate, filtered and concentrated to give a residue that is washed with ethanol (20 mL) to afford 3-chloro-6-methoxy-[1,5]naphthyridine-4-carbonitrile as an off-white solid (49.5 g, 62% yield).

$^1$H-NMR (400 MHz, DMSO-d6) δ ppm: 8.98 (s, 1H), 8.33 (d, J=9.2 Hz, 1H), 7.37 (d, J=9.2 Hz, 1H), 4.05 (s, 3H).

MS m/z (+ESI): 220.1 $[M+H]^+$.

Preparation of 3-benzyloxy-6-methoxy-[1,5]naphthyridine-4-carbonitrile

Sodium hydride (70 mg, 1.73 mmol, 2.0 eq) is added at −30° C. to a stirred solution of 3-chloro-6-methoxy-[1,5]naphthyridine-4-carbonitrile (190 mg, 0.87 mmol, 1.0 eq) and benzyl alcohol (187 mg, 1.73 mmol, 2.0 eq) in tetrahydrofuran (12 mL). After 2 hours stirring at −30° C., the reaction mixture is concentrated and extracted with ethyl acetate (3×20 mL) and water (20 mL). The combined organic layers are dried over sodium sulfate, filtered and concentrated to give a residue that is purified by column chromatography (silica gel, eluent: petroleum ether:ethyl acetate, 5:1, v/v) to afford 3-benzyloxy-6-methoxy-[1,5]naphthyridine-4-carbonitrile as a light yellow solid (160 mg, 64% yield).

$^1$H-NMR (400 MHz, DMSO-d6) δ ppm: 9.06 (s, 1H), 8.31 (d, J=8.8 Hz, 1H), 7.45 (m, 5H), 7.22 (d, J=8.8 Hz, 1H), 5.61 (s, 2H), 4.05 (s, 3H).

MS m/z (+ESI): 292.0 $[M+H]^+$.

Preparation of 3-benzyloxy-6-methoxy-[1,5]naphthyridine-4-carboxylic acid amide

30% Hydrogen peroxide (17.2 mmol, 5.0 eq) is added dropwise at room temperature to a stirred suspension of 3-benzyloxy-6-methoxy-[1,5]naphthyridine-4-carbonitrile (1.0 g, 3.43 mmol, 1.0 eq) and sodium hydroxide (69 mg, 0.17 mmol, 0.05 eq) in methanol (100 mL). After 1 hour stirring at 70° C., a catalytic amount of manganese dioxide is added to the reaction mixture that is concentrated to give a crude that is purified by column chromatography (silica gel, eluent: petroleum ether:ethyl acetate, 1:1, v/v) to afford 3-benzyloxy-6-methoxy-[1,5]naphthyridine-4-carboxylic acid amide as a white solid (800 mg, 75% yield).

$^1$H-NMR (400 MHz, $CDCl_3$) δ ppm: 8.67 (s, 1H), 8.12 (d, J=8.8 Hz, 1H), 7.40 (m, 5H), 6.48 (d, J=8.8 Hz, 1H), 6.48 (br, 1H), 6.02 (br, 1H), 5.40 (s, 2H), 4.06 (s, 3H).

MS m/z (+ESI): 310.0 $[M+H]^+$.

Preparation of (3-benzyloxy-6-methoxy-[1,5]naphthyridine-4-yl)-methanol

A solution of 3-benzyloxy-6-methoxy-[1,5]naphthyridine-4-carboxylic acid amide (640 mg, 2.07 mmol, 1.0 eq) in tetrahydrofuran (50 mL) is added at room temperature to a flask charged with Schwartz's reagent (800 mg, 3.1 mmol, 1.5 eq) and the resulting mixture is stirred at room temperature for 10 minutes. Solvent is removed to give a crude that is purified by column chromatography (silica gel, eluent: petroleum ether:ethyl acetate, 1:1, v/v) to afford a mixture of aldehyde and alcohol. This mixture is dissolved in methanol (20 mL) and sodium borohydride (39 mg, 1.03 mmol, 0.5 eq) is added at room temperature. After 5 minutes stirring at room temperature, solvent is removed to give a crude that is purified by column chromatography (silica gel, eluent: petroleum ether:ethyl acetate, 4:1, v/v) to afford (3-benzyloxy-6-methoxy-[1,5]naphthyridine-4-yl)-methanol as a white solid (390 mg, 64% yield).

$^1$H-NMR (400 MHz, $CDCl_3$) δ ppm: 8.65 (s, 1H), 8.18 (d, J=9.2 Hz, 1H), 7.42 (m, 5H), 7.02 (d, J=9.2 Hz, 1H), 5.33 (s, 2H), 5.28 (s, 2H), 4.07 (s, 3H).

MS m/z (+ESI): 297.1 $[M+H]^+$.

Preparation of 4-hydroxymethyl-6-methoxy-[1,5]naphthyridin-3-ol

10% Palladium on activated carbon (140 mg, 0.13 mmol, 0.1 eq) is added at room temperature to a stirred solution of (3-benzyloxy-6-methoxy-[1,5]naphthyridine-4-yl)-methanol (390 mg, 1.32 mmol, 1.0 eq) in methanol (30 mL). The resulting mixture is stirred under hydrogen flow (4 bars) at room temperature for 1 hour. The catalyst is then removed by filtration and the solution is concentrated to afford 4-hydroxymethyl-6-methoxy-[1,5]naphthyridin-3-ol as a white solid (220 mg, 81% yield).

$^1$H-NMR (400 MHz, $CD_3OD$) δ ppm: 8.38 (s, 1H), 8.07 (d, J=9.2 Hz, 1H), 6.99 (d, J=9.2 Hz, 1H), 5.30 (s, 2H), 4.06 (s, 3H).

MS m/z (+ESI): 207.1 $[M+H]^+$.

Preparation of 4-hydroxy-6-methoxy-[1,5]naphthyridine-4-carbaldehyde

Manganese dioxide (530 mg, 6.05 mmol, 5.0 eq) is added at room temperature to a stirred solution of 4-hydroxymethyl-6-methoxy-[1,5]naphthyridin-3-ol (250 mg, 1.21 mmol, 1.0 eq) in acetonitrile (10 mL) and the resulting mixture is stirred at 35° C. for 1 hour. The solid is filtered off, washed with acetone (3×10 mL) and the filtrate is concentrated to give a residue that is purified by column chromatography (silica gel, eluent: petroleum ether:ethyl acetate, 1:4, v/v) to afford 4-hydroxy-6-methoxy-[1,5]naphthyridine-4-carbaldehyde as a light yellow solid (180 mg, 73% yield).

$^1$H-NMR (400 MHz, $CDCl_3$) δ ppm: 11.89 (s, 1H), 11.19 (s, 1H), 8.66 (s, 1H), 8.17 (d, J=8.8 Hz, 1H), 7.01 (d, J=8.8 Hz, 1H), 4.09 (s, 3H).

MS m/z (+ESI): 205.1 $[M+H]^+$.

Preparation of 3-oxo-3,4-dihydro-2H-benzo[1,4]oxazine-6-carboxylic acid [4-(6-methoxy-3,4-dihydro-2H-1-oxa-5,9-diaza-phenanthren-3-yl)-cyclohexyl]-amide The titled compound is prepared as a white lyophilizated powder following Scheme 6 and in analogy to Example 15 using 4-hydroxy-6-methoxy-[1,5]naphthyridine-4-carbaldehyde, [4-(2-oxo-ethyl)-cyclohexyl]-carbamic acid tert-butyl ester and 3-oxo-3,4-dihydro-2H-benzo[1,4]oxazine-6-carboxylic acid as starting materials.

MS m/z (+ESI): 489.4 $[M+H]^+$.

Example 43

3-oxo-3,4-dihydro-2H-benzo[1,4]thiazine-6-carboxylic acid [trans-4-(4-hydroxy-6-methoxy-3,4-dihydro-2H-1-oxa-9-aza-phenanthren-3-yl)-cyclohexyl]-amide Preparation of [trans-4-(4-hydroxy-6-methoxy-3,4-dihydro-2H-1-oxa-9-aza-phenanthren-3-yl)-cyclohexyl]-carbamic acid tert-butyl ester Potassium tert-butoxide (354 mg, 3.15 mmol, 2.5 eq) is added at room temperature to a stirred solution of [trans-4-(6-methoxy-3,4-dihydro-2H-1-oxa-9-aza-phenanthren-3-yl)-cyclohexyl]-carbamic acid tert-butyl ester (2.6 g, 1.26 mmol, 1.0 eq) in dimethyl sulfoxide (45 mL) and tert-butanol (13 mL) under oxygen atmosphere. After 1 hour stirring under oxygen atmosphere, the reaction mixture is purged with nitrogen, and extracted with dichloromethane (3×200 mL) and water (200 mL). The combined organic layers are dried over sodium sulfate, filtered and concentrated to give a residue that is purified by column chromatography (silica gel, eluent: dichloromethane:methanol, 250:1 to 100:1, v/v) to afford [trans-4-(4-hydroxy-6-methoxy-3,4-dihydro-2H-1-oxa-9-aza-phenanthren-3-yl)-cyclohexyl]-carbamic acid tert-butyl ester as a white solid that is further purified by preparative HPLC to obtain a white solid (70 mg, 42% yield).

$^1$H-NMR (400 MHz, DMSO-d6) δ ppm: 8.42 (s, 1H), 7.83 (d, J=8.8 Hz, 1H), 7.47 (d, J=2.0 Hz, 1H), 7.23 (dd, J=2.0, 8.8 Hz, 1H), 6.57 (m, 1H), 5.00 (br, 1H), 4.24 and 4.36 (2m, 2H), 3.91 (s, 3H), 3.13 (m, 1H), 0.91-1.08 and 1.67-1.88 (2m, 10H), 1.33 (s, 9H).

MS m/z (+ESI): 429.3 $[M+H]^+$.

Preparation of 3-oxo-3,4-dihydro-2H-benzo[1,4]thiazine-6-carboxylic acid [trans-4-(4-hydroxy-6-methoxy-3,4-dihydro-2H-1-oxa-9-aza-phenanthren-3-yl)-cyclohexyl]-amide The titled compound is prepared as a white lyophilizated powder following Scheme 6 and in analogy to Example 15 using [trans-4-(4-hydroxy-6-methoxy-3,4-dihydro-2H-1-oxa-9-aza-phenanthren-3-yl)-cyclohexyl]-carbamic acid tert-butyl ester and 3-oxo-3,4-dihydro-2H-benzo[1,4]thiazine-6-carboxylic acid as starting materials.

MS m/z (+ESI): 520.4 $[M+H]^+$.

Example 44

3-oxo-3,4-dihydro-2H-benzo[1,4]thiazine-6-carboxylic acid [trans-4-(6-methoxy-4-oxo-3,4-dihydro-2H-1-oxa-9-aza-phenanthren-3-yl)-cyclohexyl]-amide Preparation of [trans-4-(4-hydroxy-6-methoxy-3,4-dihydro-2H-1-oxa-9-aza-phenanthren-3-yl)-cyclohexyl]-carbamic acid tert-butyl ester Pyridine chlorochromate (2.92 g, 13.5 mmol, 10.0 eq) is added at room temperature to a stirred solution of [trans-4-(4-hydroxy-6-methoxy-3,4-dihydro-2H-1-oxa-9-aza-phenanthren-3-yl)-cyclohexyl]-carbamic acid tert-butyl ester (580 mg, 1.35 mmol, 1.0 eq) in dichloromethane (40 mL). After stirring at room temperature for 15 hours, diethyl ether (1000 mL) is added and the resulting suspension is filtered. The filtrate is concentrated to give a residue that is purified by preparative HPLC to afford [trans-4-(4-hydroxy-6-methoxy-3,4-dihydro-2H-1-oxa-9-aza-phenanthren-3-yl)-cyclohexyl]-carbamic acid tert-butyl ester as a light yellow solid (280 mg, 37% yield).

$^1$H-NMR (400 MHz, DMSO-d6) δ ppm: 8.69 (d, J=2.8 Hz, 1H), 8.62 (s, 1H), 7.89 (d, J=9.1 Hz, 1H), 7.28 (d, J=2.8, 9.1 Hz, 1H), 6.64 (m, 1H), 4.71 (m, 2H), 3.89 (s, 3H), 3.14 (m, 1H), 2.58 (m, 1H), 1.34 (s, 9H), 1.04-1.24, 1.51-1.54, 1.77 (3m, 9H).

MS m/z (+ESI): 427.3 $[M+H]^+$.

Preparation of 3-oxo-3,4-dihydro-2H-benzo[1,4]thiazine-6-carboxylic acid [trans-4-(6-methoxy-4-oxo-3,4-dihydro-2H-1-oxa-9-aza-phenanthren-3-yl)-cyclohexyl]-amide The titled compound is prepared as a white lyophilizated powder following Scheme 6 and in analogy to Example 15 using [trans-4-(4-hydroxy-6-methoxy-3,4-dihydro-2H-1-oxa-9-aza-phenanthren-3-yl)-cyclohexyl]-carbamic acid tert-butyl ester and 3-oxo-3,4-dihydro-2H-benzo[1,4]thiazine-6-carboxylic acid as starting materials.

$^1$H-NMR (400 MHz, DMSO-d6) δ ppm: 10.63 (s, 1H), 8.70 (d, J=2.8 Hz, 1H), 8.65 (s, 1H), 8.19 (d, J=7.9 Hz, 1H), 7.92 (d, J=9.1 Hz, 1H), 7.40 (m, 3H), 7.31 (dd, J=2.8, 9.1 Hz, 1H), 4.77 (m, 2H), 3.92 (s, 3H), 3.75 (m, 1H), 3.49 (s, 2H), 2.67 (m, 1H), 1.29, 1.63, 1.85 (3m, 9H).

MS m/z (+ESI): 518.4 $[M+H]^+$.

Example 47

3-oxo-3,4-dihydro-2H-benzo[1,4]thiazine-6-carboxylic acid [trans-4-(6-methoxy-2,3-dihydro-1H-4-oxa-1,5,9-triaza-phenanthren-3-yl)-cyclohexyl]-amide Preparation of 4-chloro-6-methoxy-[1,5]naphthyridine-3-carboxylic acid Sodium hydroxide (5.86 g, 140.6 mmol, 2.5 eq) is added protionwise at room temperature to a stirred solution of 4-chloro-6-methoxy-[1,5]naphthyridine-3-carboxylic acid ethyl ester (15.0 g, 56.25 mmol, 1.0 eq) in tetrahydrofuran (150 mL) and water (80 mL). After 15 hours stirring at room temperature, tetrahydrofuran is removed, the aqueous layer is cooled down to 0° C. and the pH is adjusted to 3 by the addition of a 2N hydrochloric acid aqueous solution. The resulting precipitate is collected by filtration, washed with water and dried under high vacuum to afford 4-chloro-6-methoxy-[1,5]naphthyridine-3-carboxylic acid as a light red solid (12.9 g, 96% yield).

$^1$H-NMR (400 MHz, DMSO-d6) δ ppm: 8.99 (s, 1H), 8.35 (d, J=9.6 Hz, 1H), 7.41 (d, J=9.6 Hz, 1 h), 4.07 (s, 3H).

MS m/z (+ESI): 239.2 $[M+H]^+$.

Preparation of 4-benzyloxy-6-methoxy-[1,5]naphthyridine-3-carboxylic acid

Benzyl alcohol (5.78 g, 53.43 mmol, 2.5 eq) is added at −45° C. to a stirred solution of 4-chloro-6-methoxy-[1,5]naphthyridine-3-carboxylic acid (5.1 g, 21.37 mmol, 1.0 eq) in N,N-dimethylformamide (100 mL), followed by sodium hydride (2.46 g, 53.43 mmol, 2.5 eq). After 2 hours stirring at −40° C. and 24 hours stirring at room temperature, the reaction mixture is quenched with ice water, the pH is adjusted to 3-4 by the addition of a 2N hydrochloric acid aqueous solution. The resulting precipitate is collected by filtration, washed with water and dried under high vacuum to afford 4-benzyloxy-6-methoxy-[1,5]naphthyridine-3-carboxylic acid as a light red solid (6.5 g, 98% yield).

$^1$H-NMR (400 MHz, $CDCl_3$) δ ppm: 9.32 (s, 1H), 8.32 (d, J=9.2 Hz, 1H), 7.31-7.47 (m, 6H), 6.12 (s, 2H), 4.07 (s, 3H).

MS m/z (+ESI): 311.1 $[M+H]^+$.

Preparation of (4-benzyloxy-6-methoxy-[1,5]naphthyridin-3-yl)-carbamic acid tert-butyl ester Diphenylphosphoryl azide (25.0 mL, 116.0 mmol, 1.5 eq) is added at room temperature to a stirred solution of 4-benzyloxy-6-methoxy-[1,5]naphthyridine-3-carboxylic acid (24.0 g, 77.34 mmol, 1.0 eq) in N,N-dimethylformamide (300 mL), followed by tert-butanol (8.5 mL, 89.71 mmol, 1.16 eq) and triethylamine (104.5 mL, 773.4 mmol, 10.0 eq). After 30 minutes stirring at 70° C. and 2 hours at 100° C., the reaction mixture is cooled down to room temperature, solvent is removed and the residue is extracted with ethyl acetate (3×200 mL) and a saturated sodium hydrogen carbonate aqueous solution (200 mL). The combined organic layers are dried over sodium sulfate, filtered and concentrated to afford crude (4-benzyloxy-6-methoxy-[1,5]naphthyridin-3-yl)-carbamic acid tert-butyl ester that is directly engaged in the next step.

MS m/z (+ESI): 382.1 $[M+H]^+$.

Preparation of 4-benzyloxy-6-methoxy-[1,5]naphthyridin-3-ylamine

Trifluoroacetic acid (10.0 mL, 131.2 mmol, 20.0 eq) is added at 0° C. to a stirred solution of (4-benzyloxy-6-methoxy-[1,5]naphthyridin-3-yl)-carbamic acid tert-butyl ester (2.50 g, 6.55 mmol, 1.0 eq) in dichloromethane (50 mL). After 20 hours stirring at 0° C., the reaction mixture is extracted with dichloromethane (3×200 mL) and water (200 mL) and the pH is adjusted to 12 by the addition of a 1N sodium hydroxide aqueous solution. The combined organic layers are dried over sodium sulfate, filtered and concentrated to afford 4-benzyloxy-6-methoxy-[1,5]naphthyridin-3-ylamine as a light yellow solid (1.70 g, 92% yield).

$^1$H-NMR (400 MHz, DMSO-d6) δ ppm: 8.84 (s, 1H), 8.55 (d, J=9.2 Hz, 1H), 7.41 (m, 6H), 7.10 (d, J=9.2 Hz, 1H), 6.14 (s, 2H), 4.14 (s, 3H).

MS m/z (+ESI): 282.1 [M+H]

Preparation of 3-amino-6-methoxy-[1,5]naphthyridin-4-ol

10% Palladium on activated carbon (76 mg, 0.07 mmol, 0.1 eq) is added at room temperature to a stirred solution of 4-benzyloxy-6-methoxy-[1,5]naphthyridin-3-ylamine (200 mg, 0.71 mmol, 1.0 eq) in methanol (20 mL). The resulting mixture is stirred under hydrogen flow (3 bars) at room temperature for 16 hours. The catalyst is then removed by filtration and the solution is concentrated to give a residue that is purified by column chromatography (silica gel, eluent: dichloromethane:methanol, 50:1 to 10:1, v/v) to afford 3-amino-6-methoxy-[1,5]naphthyridin-4-ol as a yellow solid (39 mg, 29% yield).

$^1$H-NMR (400 MHz, DMSO-d6) δ ppm: 7.93 (d, J=8.8 Hz, 1H), 6.92 (d, J=8.8 Hz, 1H), 6.85 (s, 1H), 3.97 (s, 3H).

MS m/z (+ESI): 192.1 $[M+H]^+$.

Preparation of [trans-4-(1,3-dioxo-1,3-dihydro-isoindol-2-yl)-cyclohexyl]-acetic acid Trifluoroacetic acid (44.6 mL, 583.0 mmol, 30.0 eq) is added at room temperature to a stirred solution of (trans-4-tert-butoxycarbonylamino-cyclohexyl)-acetic acid (5.0 g, 19.4 mmol, 1.0 eq) in dichloromethane (50 mL). After 3 hours stirring at room temperature, the reaction mixture is concentrated, the resulting residue is dissolved in pyridine (150 mL) and phthalic anhydride (5.0 g, 33.0 mmol, 1.7 eq) is added at room temperature. The reaction mixture is heated to reflux for 4 hours, pyridine is then removed and acetic anhydride (40 mL) is added. The resulting mixture is heated to reflux for 3 hours, then extracted with ethyl acetate (3×200 mL) and water (200 mL). The combined organic layers are dried over sodium sulfate, filtered and concentrated to give a residue that is purified by column chromatography (silica gel, eluent: dichloromethane:methanol, 50:1 to 10:1, v/v) to afford [trans-4-(1,3-dioxo-1,3-dihydro-isoindol-2-yl)-cyclohexyl]-acetic acid as a white solid (4.82 g, 86% yield).

$^1$H-NMR (400 MHz, DMSO-d6) δ ppm: 12.04 (br, 1H), 7.93 (s, 4H), 4.00 (m, 1H), 1.07-2.39 (m, 11H).

MS m/z (−ESI): 286.1 $[M-H]^+$.

Preparation of [trans-4-(1,3-dioxo-1,3-dihydro-isoindol-2-yl)-cyclohexyl]-acetic acid A mixture of thionyl chloride (50 mL, 685.0 mmol, 50.7 eq) and [trans-4-(1,3-dioxo-1,3-dihydro-isoindol-2-yl)-cyclohexyl]-acetic acid (3.88 g, 13.5 mmol, 1.0 eq) is heated to reflux for 4 hours before the addition of bromine (761 μL, 14.85 mmol, 1.1 eq). The resulting mixture is heated to reflux for 14 hours, then concentrated to give a residue that is directly engaged in the next step.

$^1$H-NMR (400 MHz, DMSO-d6) δ ppm: 7.82 (s, 4H), 4.39 (d, J=11.6 Hz, 1H), 4.03 (m, 1H), 1.79-2.48 (m, 9H).

Preparation of 2-bromo-[trans-4-1,3-dihydro-isoindol-2-yl)-cyclohexyl]-N-(4-hydroxy-6-methoxy-[1,5]naphthyridin-3-yl)-acetamide Triethylamine (2.0 mL, 14.38 mmol, 5.0 eq) is added at room temperature to a stirred solution of [trans-4-(1,3-dioxo-1,3-dihydro-isoindol-2-yl)-cyclohexyl]-acetic acid (1.22 g, 3.17 mmol, 1.1 eq) and 3-amino-6-methoxy-[1,5]naphthyridin-4-ol (550 mg, 2.88 mmol, 1.0 eq) in tetrahydrofuran (80 mL). After 14 hours stirring at room temperature, solvent is removed to give a residue that is directly engaged in the next step (670 mg, 71% yield).

MS m/z (+ESI): 539.0/541.0 $[M+H]^+$.

Preparation of 2-[trans-4-(6-methoxy-2-oxo-2,3-dihydro-1H-4-oxa-1,5,9-triaza-phenanthren-3-yl)-cyclohexyl]-isoindole-1,3-dione Potassium carbonate (2.49 g, 18.03 mmol, 3.0 eq) is added at room temperature to a stirred solution of 2-bromo-[trans-4-(1,3-dioxo-1,3-dihydro-isoindol-2-yl)-cyclohexyl]-N-(4-hydroxy-6-methoxy-[1,5]naphthyridin-3-yl)-acetamide (3.24 g, 6.01 mmol, 1.0 eq) in N,N-dimethylformamide (30 mL). After 16 hours stirring at room temperature and 2 hours stirring at 55° C., solvent is removed and the residue is purified by column chromatography (silica gel, eluent: dichloromethane:methanol, 50:1, v/v) to afford 2-[trans-4-(6-methoxy-2-oxo-2,3-dihydro-H-1H-4-oxa-1,5,9-triaza-phenanthren-3-yl)-cyclohexyl]-isoindole-1,3-dione as a light yellow solid (1.35 g, 49% yield).

$^1$H-NMR (400 MHz, DMSO-d6) δ ppm: 11.16 (m, 1H), 8.38 (m, 1H), 8.15 (m, 1H), 7.81 (m, 4H), 7.13 (m, 1H), 4.61, 5.05 (2m, 1H), 3.99-4.16 (m, 3H), 3.58 (m, 1H), 1.56-1.99 (m, 9H).

MS m/z (+ESI): 459.4 $[M+H]^+$.

Preparation of 3-(trans-4-amino-cyclohexyl)-6-methoxy-1H-4-oxa-1,5,9-triaza-phenanthren-2-one Hydrazine hydrate (2M solution in methanol, 10 mL, 20.0 mmol, 7.96 eq) is added at room temperature to a stirred solution of 2-[trans-4-(6-methoxy-2-oxo-2,3-dihydro-1H-4-oxa-1,5,9-triaza-phenanthren-3-yl)-cyclohexyl]-isoindole-1,3-dione (1.15 g, 2.51 mmol, 1.0 eq) in dichloromethane (15 mL) and methanol (15 mL). After 16 hours stirring at room temperature and 2 hours stirring at 55° C., solvent is removed and the residue is purified by preparative HPLC to afford 3-(trans-4-amino-cyclohexyl)-6-methoxy-1H-4-oxa-1,5,9-triaza-phenanthren-2-one as a yellow solid (260 mg, 32% yield).

MS m/z (+ESI): 329.2 $[M+H]^+$.

Preparation of trans-4-(6-methoxy-2,3-dihydro-1H-4-oxa-1,5,9-triaza-phenanthren-3-yl)-cyclohexylamine Borane dimethyl sulfide complex (2M solution in tetrahydrofuran, 12.5 mL, 25.0 mmol, 10.0 eq) is added at room temperature to a stirred solution of 3-(trans-4-amino-cyclohexyl)-6-methoxy-1H-4-oxa-1,5,9-triaza-phenanthren-2-one (821 mg, 2.50 mmol, 1.0 eq) in tetrahydrofuran (80 mL). The reaction mixture is heated to reflux for 3 hours, cooled down to 0° C. and cautiously quenched with methanol (10 mL) and then evaporated to give a residue that is purified by column chromatography (silica gel, eluent: dichloromethane: methanol, 1:1, v/v) to afford trans-4-(6-methoxy-2,3-dihydro-1H-4-oxa-1,5,9-triaza-phenanthren-3-yl)-cyclohexylamine as a yellow solid (340 mg, 45% yield).

MS m/z (+ESI): 315.1 $[M+H]^+$.

Preparation of 3-oxo-3,4-dihydro-2H-benzo[1,4]thiazine-6-carboxylic acid [trans-4-(6-methoxy-2,3-dihydro-1H-4-oxa-1,5,9-triaza-phenanthren-3-yl)-cyclohexyl]-amide The titled compound is prepared as a white lyophilizated powder following Scheme 7 and in analogy to Example 1 using trans-4-(6-methoxy-2,3-dihydro-1H-4-oxa-1,5,9-triaza-phenanthren-3-yl)-cyclohexylamine and 3-oxo-3,4-dihydro-2H-benzo[1,4]thiazine-6-carboxylic acid as starting materials.

MS m/z (+ESI): 506.5 $[M+H]^+$.

Example 48

3-oxo-3,4-dihydro-2H-benzo[1,4]thiazine-6-carboxylic acid [trans-4-(6-hydroxy-3,4-dihydro-2H-1-oxa-9-aza-phenanthren-3-yl)-cyclohexyl]-amide Preparation of 3-(trans-4-amino-cyclohexyl)-3,4-dihydro-2H-1-oxa-9-aza-phenanthren-6-ol 47% Hydrobromic acid (36 mL, 0.33 mol, 75.0 eq) is added at room temperature to a stirred solution of [trans-4-(6-methoxy-3,4-dihydro-2H-1-oxa-9-aza-phenanthren-3-yl)-cyclohexyl]-carbamic acid tert-butyl ester (1.8 g, 4.36 mmol, 1.0 eq) in acetic acid (25 mL). After 18 hours stirring at 130° C., the reaction mixture is cooled down to 0° C. and the resulting precipitate is collected by filtration, washed with acetonitrile and dried under high vacuum to afford 3-(trans-4-amino-cyclohexyl)-3,4-dihydro-2H-1-oxa-9-aza-phenanthren-6-ol as a light yellow solid (1.13 g, 87% yield).

$^1$H-NMR (400 MHz, DMSO-d6) δ ppm: 10.70 (br, 1H), 8.79 (s, 1H), 7.99 (d, J=9.2 Hz, 1H), 7.84 (s, 3H) 7.43 (d, J=8.8 Hz, 1H), 7.32 (s, 1H), 4.49 (m, 1H), 3.99 (m, 1H), 3.19 (m, 1H), 2.98 (m, 1H), 2.88 (m, 1H), 1.89-2.00 (m, 5H), 1.18-1.33 (m, 5H).

MS m/z (+ESI): 299.1 $[M+H]^+$.

Preparation of 3-oxo-3,4-dihydro-2H-benzo[1,4]thiazine-6-carboxylic acid [trans-4-(6-hydroxy-3,4-dihydro-2H-1-oxa-9-aza-phenanthren-3-yl)-cyclohexyl]-amide The titled compound is prepared as a white lyophilizated powder following Scheme 6 and in analogy to Example 15 using 3-(trans-4-amino-cyclohexyl)-3,4-dihydro-2H-1-oxa-9-aza-phenanthren-6-ol and 3-oxo-3,4-dihydro-2H-benzo[1,4]thiazine-6-carboxylic acid as starting materials.

$^1$H-NMR (400 MHz, DMSO-d6+$D_2O$) δ ppm: 8.29 (s, 1H), 7.80 (d, J=9.1 Hz, 1H), 7.39 (s, 2H), 7.33 (s, 1H), 7.19 (dd, J=2.5, 9.1 Hz, 1H), 7.13 (d, J=2.3 Hz, 1H), 4.38 (m, 1H), 3.93 (m, 1H), 3.71 (m, 1H), 3.43 (s, 2H), 3.02 (m, 1H), 2.73 (m, 1H), 1.80-1.98 (m, 5H), 1.20-1.40 (m, 5H).

MS m/z (+ESI): 490.2 $[M+H]^+$.

Example 49

3-oxo-3,4-dihydro-2H-benzo[1,4]thiazine-6-carboxylic acid [trans-4-(6-methoxy-1-methyl-2,3-dihydro-1H-4-oxa-1,5,9-triaza-phenanthren-3-yl)-cyclohexyl]-amide Preparation of 2-[trans-4-(6-methoxy-1-methyl-2-oxo-2,3-dihydro-1H-4-oxa-1,5,9-triaza-phenanthren-3-yl)-cyclohexyl]-isoindole-1,3-dione Sodium carbonate (405 mg, 3.82 mmol, 3.5 eq) is added at −5° C. to a stirred solution of 2-[trans-4-(6-methoxy-2-oxo-2,3-dihydro-1H-4-oxa-1,5,9-triaza-phenanthren-3-yl)-cyclohexyl]-isoindole-1,3-dione (500 mg, 1.09 mmol, 1.0 eq) in N,N-dimethylformamide (30 mL), followed by iodomethane (408 μL, 6.55 mmol, 6.0 eq). After 14 hours stirring at −5° C., solvent is removed and the residue is extracted with ethyl acetate (3×100 mL) and water (100 mL). The combined organic layers are washed with brine, dried over sodium sulfate, filtered and concentrated to give a crude that is purified by column chromatography (silica gel, eluent: dichloromethane:methanol, 50:1, v/v) to afford 2-[trans-4-(6-methoxy-1-methyl-2-oxo-2,3-dihydro-1H-4-oxa-1,5,9-triaza-phenanthren-3-yl)-cyclohexyl]-isoindole-1,3-dione as a light red semisolid (420 mg, 81% yield).

MS m/z (+ESI): 473.2 [M+H]

Preparation of 3-(trans-4-amino-cyclohexyl)-6-methoxy-1-methyl-1H-4-oxa-1,5,9-triaza-phenanthren-2-one Hydrazine hydrate (2M solution in methanol, 3.56 mL, 7.12 mmol, 8.0 eq) is added at room temperature to a stirred solution of 2-[trans-4-(6-methoxy-1-methyl-2-oxo-2,3-dihydro-1H-4-oxa-1,5,9-triaza-phenanthren-3-yl)-cyclohexyl]-isoindole-1,3-dione (420 mg, 0.89 mmol, 1.0 eq) in dichloromethane (10 mL) and methanol (20 mL). After 16 hours stirring at room temperature and 2 hours stirring at 55° C., solvent is removed and the residue is purified by preparative HPLC to afford 3-(trans-4-amino-cyclohexyl)-6-methoxy-1H-4-oxa-1,5,9-triaza-phenanthren-2-one as a light grey solid (160 mg, 56% yield).

$^1$H-NMR (400 MHz, DMSO-d6) δ ppm: 8.66 (m, 1H), 8.15 (m, 1H), 7.15 (m, 1H), 4.81-4.89 (m, 1H), 3.98 (s, 3H), 3.44 (s, 3H), 2.82 (m, 1H), 1.08-1.78 (m, 8H), 0.80-1.00 (m, 1H).

MS m/z (+ESI): 343.2 [M+H]

Preparation of trans-4-(6-methoxy-1-methyl-2,3-dihydro-1H-4-oxa-1,5,9-triaza-phenanthren-3-yl)-cyclohexylamine Borane dimethyl sulfide complex (2M solution in tetrahydrofuran, 60.0 mL, 120.0 mmol, 24.5 eq) is added at room temperature to a stirred solution of 3-(trans-4-amino-cyclohexyl)-6-methoxy-1H-4-oxa-1,5,9-triaza-phenanthren-2-one (1.67 g, 4.88 mmol, 1.0 eq) in tetrahydrofuran (600 mL). The reaction mixture is heated to reflux for 3 hours, cooled down to 0° C. and cautiously quenched with methanol (100 mL) and then evaporated to give crude trans-4-(6-methoxy-1-methyl-2,3-dihydro-1H-4-oxa-1,5,9-triaza-phenanthren-3-yl)-cyclohexylamine that is directly engaged in the next step.

Preparation of 3-oxo-3,4-dihydro-2H-benzo[1,4]thiazine-6-carboxylic acid [trans-4-(6-methoxy-1-methyl-2,3-dihydro-1H-4-oxa-1,5,9-triaza-phenanthren-3-yl)-cyclohexyl]-amide The titled compound is prepared as an off-white lyophilizated powder following Scheme 7 and in analogy to Example 47 using trans-4-(6-methoxy-1-methyl-2,3-dihydro-1H-4-oxa-1,5,9-triaza-phenanthren-3-yl)-cyclohexylamine and 3-oxo-3,4-dihydro-2H-benzo[1,4]thiazine-6-carboxylic acid as starting materials.

MS m/z (+ESI): 520.6 $[M+H]^+$.

Example 50

3-oxo-3,4-dihydro-2H-benzo[1,4]thiazine-6-carboxylic acid [trans-4-(3,4-dihydro-2H-1-oxa-9-aza-phenanthren-3-yl)-cyclohexyl]-amide Preparation of 3-hydroxy-quinoline-4-carbaldehyde Quinolin-3-ol (500 mg, 3.44 mmol, 1.0 eq) is added at room temperature to a stirred solution of sodium hydroxide (1.6 g, 40.0 mmol, 11.6 eq) in chloroform (1 mL) and water (10 mL). After 2 hours stirring at 100° C., the reaction mixture is extracted with dichloromethane (3×20 mL) and water (20 mL) and the pH is adjusted to 4 by the addition of a 1N hydrochloric acid aqueous solution. The combined organic layers are dried over sodium sulfate, filtered and concentrated to give a residue that is purified by column chromatography (silica gel, eluent: dichloromethane:methanol, 200:1, v/v) to afford 3-hydroxy-quinoline-4-carbaldehyde as a yellow solid (60 mg, 10% yield).

$^1$H-NMR (400 MHz, DMSO-d6) δ ppm: 10.78 (s, 1H), 8.86 (d, J=8.4 Hz, 1H), 8.84 (s, 1H), 7.95 (d, J=8.4 Hz, 1H), 7.64 (t, J=7.2 Hz, 1H), 7.58 (t, J=7.2 Hz, 1H).

MS m/z (+ESI): 174.1 $[M+H]^+$.

Preparation of 3-oxo-3,4-dihydro-2H-benzo[1,4]thiazine-6-carboxylic acid [trans-4-(3,4-dihydro-2H-1-oxa-9-aza-phenanthren-3-yl)-cyclohexyl]-amide The titled compound is prepared as a white lyophilizated powder following Scheme 6 and in analogy to Example 15 using 3-hydroxy-quinoline-4-carbaldehyde, [trans-4-(2-oxo-ethyl)-cyclohexyl]-carbamic acid tert-butyl ester and 3-oxo-3,4-dihydro-2H-benzo[1,4]thiazine-6-carboxylic acid as starting materials.

$^1$H-NMR (400 MHz, DMSO-d6) δ ppm: 10.66 (s, 1H), 8.52 (s, 1H), 8.24 (d, J=7.9 Hz, 1H), 7.97 (m, 2H), 7.60 (m, 2H), 7.47 (m, 2H), 7.40 (m, 1H), 4.47 (m, 1H), 3.93 (t, J=10.3 Hz, 1H), 3.77 (m, 1H), 3.51 (s, 2H), 3.19 (m, 1H), 2.84 (m, 1H), 1.97 (m, 5H), 1.34 (m, 5H).

MS m/z (+ESI): 474.5 $[M+H]^+$.

Example 62

3-oxo-3,4-dihydro-2H-benzo[1,4]thiazine-6-carboxylic acid [trans-4-(6-methoxy-4-methyl-3,4-dihydro-2H-1-oxa-4,5,9-triaza-phenanthren-3-yl)-cyclohexyl]-amide Preparation of 2-[trans-4-(6-methoxy-3,4-dihydro-2H-1-oxa-4,5,9-triaza-phenanthren-3-yl)-cyclohexyl]-isoindole-1,3-dione Phthalic anhydride (200 mg, 1.34 mmol, 2.53 eq) is added at room temperature to a stirred solution of trans-4-(6-methoxy-3,4-dihydro-2H-1-oxa-4,5,9-triaza-phenanthren-3-yl)-cyclohexylamine (200 mg, 0.53 mmol, 1.0 eq) in pyridine (4 mL). The reaction mixture is heated to reflux for 3 hours, pyridine is then removed and acetic anhydride (1 mL) is added. The resulting mixture is heated to reflux for 2 hours, then extracted with ethyl acetate (3×10 mL) and water (5 mL). The combined organic layers are dried over sodium sulfate, filtered and concentrated to afford 2-[trans-4-(6-methoxy-3,4-dihydro-2H-1-oxa-4,5,9-triaza-phenanthren-3-yl)-cyclohexyl]-isoindole-1,3-dione as a light brown semisolid (190 mg, 69% yield).

MS m/z (+ESI): 445.3 $[M+H]^+$.

Preparation of 2-[trans-4-(6-methoxy-4-methyl-3,4-dihydro-2H-1-oxa-4,5,9-triaza-phenanthren-3-yl)-cyclohexyl]-isoindole-1,3-dione Cesium carbonate (119 mg, 0.36 mmol, 1.0 eq) is added at room temperature to a stirred solution of 2-[trans-4-(6-methoxy-3,4-dihydro-2H-1-oxa-4,5,9-triaza-phenanthren-3-yl)-cyclohexyl]-isoindole-1,3-dione (190 mg, 0.36 mmol, 1.0 eq) in N,N-dimethylformamide (3 mL), followed by iodomethane (23 μL, 0.36 mmol, 1.0 eq). After 5 hours stirring at room temperature, one additional equivalent of iodomethane is added to the reaction mixture and, after 2 hours stirring, solvent is removed to give a residue that is extracted with ethyl acetate (3×10 mL) and water (10 mL). The combined organic layers are washed with brine, dried over sodium sulfate, filtered and concentrated to give a residue that is purified by column chromatography (silica gel, eluent: cyclohexane:ethyl acetate:methanol, 1:3:0 to 0:1:0 to 0:9:1, v/v/v) to afford 2-[trans-4-(6-methoxy-4-methyl-3,4-dihydro-2H-1-oxa-4,5,9-triaza-phenanthren-3-yl)-cyclohexyl]-isoindole-1,3-dione as an orange solid (113 mg, 54% yield).

MS m/z (+ESI): 459.4 $[M+H]^+$.

Preparation of trans-4-(6-methoxy-4-methyl-3,4-dihydro-2H-1-oxa-4,5,9-triaza-phenanthren-3-yl)-cyclohexylamine Hydrazine hydrate (2M solution in methanol, 90 μL, 0.18 mmol, 1.0 eq) is added at room temperature to a stirred solution of 2-[trans-4-(6-methoxy-4-methyl-3,4-dihydro-2H-1-oxa-4,5,9-triaza-phenanthren-3-yl)-cyclohexyl]-isoindole-1,3-dione (105 mg, 0.18 mmol, 1.0 eq) in ethanol (3 mL). After 16 hours stirring at 50° C., solvent is removed to afford trans-4-(6-methoxy-4-methyl-3,4-dihydro-2H-1-oxa-4,5,9-triaza-phenanthren-3-yl)-cyclohexylamine as an orange semisolid (80 mg, 93% yield).

MS m/z (+ESI): 329.4 $[M+H]^+$.

Preparation of 3-oxo-3,4-dihydro-2H-benzo[1,4]thiazine-6-carboxylic acid [trans-4-(6-methoxy-4-methyl-3,4-dihydro-2H-1-oxa-4,5,9-triaza-phenanthren-3-yl)-cyclohexyl]-amide The titled compound is prepared as an orange semisolid following Scheme 5 and in analogy to Example 27 using trans-4-(6-methoxy-4-methyl-3,4-dihydro-2H-1-oxa-4,5,9-triaza-phenanthren-3-yl)-cyclohexylamine and 3-oxo-3,4-dihydro-2H-benzo[1,4]thiazine-6-carboxylic acid as starting materials.

MS m/z (+ESI): 520.6 $[M+H]^+$.

Example 63

3-oxo-3,4-dihydro-2H-benzo[1,4]thiazine-6-carboxylic acid [trans-4-(6-ethoxy-3,4-dihydro-2H-1-oxa-9-aza-phenanthren-3-yl)-cyclohexyl]-amide Ethyl iodide (6 μL, 0.07 mmol, 1.0 eq) is added at room temperature to a stirred solution of 3-oxo-3,4-dihydro-2H-benzo[1,4]thiazine-6-carboxylic acid [trans-4-(6-hydroxy-3,4-dihydro-2H-1-oxa-9-aza-phenanthren-3-yl)-cyclohexyl]-amide (40 mg, 0.07 mmol, 1.0 eq) in N,N-dimethylformamide (4 mL), followed by sodium hydride (55% purity, 3.2 mg, 0.07 mmol, 1.0 eq). After 2 hours stirring at room temperature, 1.0 additional equivalent of ethyl iodide and sodium hydride are added to the reaction mixture that is stirred at room temperature for one hour. Then solvent is evaporated and the crude is extracted with dichloromethane (3×10 mL) and water (10 mL). The combined organic layers are dried over sodium sulfate, filtered and concentrated to give a residue that is purified by preparative HPLC to afford 3-oxo-3,4-dihydro-2H-benzo[1,4]thiazine-6-carboxylic acid [trans-4-(6-ethoxy-3,4-dihydro-2H-1-oxa-9-aza-phenanthren-3-yl)-cyclohexyl]-amide as an off-white lyophilizated powder (11 mg, 27% yield).

$^1$H-NMR (400 MHz, DMSO-d6) δ ppm: 10.66 (s, 1H), 8.33 (s, 1H), 8.24 (d, J=7.9 Hz, 1H), 7.83 (d, J=8.9 Hz, 1H), 7.38-7.48 (m, 3H), 7.21 (m, 2H), 4.44 (m, 1H), 4.22 (m, 2H), 3.89 (m, 1H), 3.79 (m, 1H), 3.51 (s, 2H), 3.12 (m, 1H), 2.75 (m, 1H), 2.05 (m, 1H), 1.94 (m, 4H), 1.22-1.45 (m, 8H).

MS m/z (+ESI): 518.6 $[M+H]^+$.

Example 72

3-oxo-3,4-dihydro-2H-benzo[1,4]thiazine-6-carboxylic acid [4-(6-methoxy-3,4-dihydro-2H-1-oxa-9-aza-phenanthren-3-yl)-thiazol-2-yl]-amide Preparation of 6-methoxy-3,4-dihydro-2H-1-oxa-9-aza-phenanthrene-3-carboxylic acid 10% Palladium on activated carbon (140 mg, 0.14 mmol, 0.05 eq) is added at room temperature to a stirred solution of 6-methoxy-2H-1-oxa-9-aza-phenanthrene-3-carboxylic acid (700 mg, 2.72 mmol, 1.0 eq) in methanol (20 mL) and tetrahydrofuran (20 mL). The resulting mixture is stirred under hydrogen flow (3 bars) at room temperature for 48 hours. The catalyst is then removed by filtration and the solution is concentrated to afford 6-methoxy-3,4-dihydro-2H-1-oxa-9-aza-phenanthrene-3-carboxylic acid as a light yellow semisolid (520 mg, 74% yield) which is directly engaged in the next step.

$^1$H-NMR (400 MHz, DMSO-d6) δ ppm: 8.67 (s, 1H), 8.17 (d, J=9.6 Hz, 1H), 7.44 (d, J=9.6 Hz, 1H), 7.33 (s, 1H), 4.38, 4.49 (2m, 2H), 3.96 (s, 3H), 3.30, 3.36 (2m, 3H).

MS m/z (+ESI): 260.0 $[M+H]^+$.

Preparation of 2-bromo-1-(6-methoxy-3,4-dihydro-2H-1-oxa-9-aza-phenanthren-3-yl)-ethanone Triethylamine (110 μL, 0.77 mmol, 2.0 eq) is added at 0° C. to a stirred solution of 6-methoxy-3,4-dihydro-2H-1-oxa-9-aza-phenanthrene-3-carboxylic acid (100 mg, 0.39 mmol, 1.0 eq) in tetrahydrofuran (10 mL), followed by ethyl chloroformate (73 μL, 0.77 mmol, 2.0 eq). After 1 hour stirring at 0° C., a solution of diazomethane in diethyl ether (20 mL, freshly prepared) is added at 0° C. to the reaction mixture. After 2 hours stirring at 0° C., a 33% hydrobromic acid solution in acetic acid (200 μL, 1.16 mmol, 3.0 eq) is added at 0° C. to the reaction mixture. After 1 hour stirring at 0° C., solvent is removed to give a crude product that is purified by column chromatography (silica gel, eluent: petroleum ether:ethyl acetate, 3:1, v/v) to afford 2-bromo-1-(6-methoxy-3,4-dihydro-2H-1-oxa-9-aza-phenanthren-3-yl)-ethanone as a light yellow oil (33 mg, 25% yield)

$^1$H-NMR (400 MHz, DMSO-d6) δ ppm: 8.32 (s, 1H), 7.82 (d, J=8.8 Hz, 1H), 7.21 (dd, J=2.8, 8.8 Hz, 1H), 7.15 (d, J=2.8 Hz, 1H), 4.89 (s, 2H), 4.21, 4.52 (2m, 2H), 3.91 (s, 3H), 3.11-3.45 (3m, 3H).

MS m/z (+ESI): 336.8, 338.8 [M+H]$^+$.

Preparation of 4-(6-methoxy-3,4-dihydro-2H-1-oxa-9-aza-phenanthren-3-yl)-thiazol-2-ylamine Thiourea (190 mg, 2.5 mmol, 1.0 eq) is added at room temperature to a stirred solution of 2-bromo-1-(6-methoxy-3,4-dihydro-2H-1-oxa-9-aza-phenanthren-3-yl)-ethanone (850 mg, 2.5 mmol, 1.0 eq) in ethanol (200 mL) and the resulting suspension is heated to reflux for 15 minutes. Then pH of the reaction mixture is adjusted to 8-10 by the addition of a 30% aqueous ammonia solution. Solvent was removed to give the crude product that is purified by preparative HPLC to afford 4-(6-methoxy-3,4-dihydro-2H-1-oxa-9-aza-phenanthren-3-yl)-thiazol-2-ylamine as a white solid (60 mg, 13% yield).

$^1$H-NMR (400 MHz, DMSO-d6) δ ppm: 8.43 (s, 1H), 7.86 (d, J=8.8 Hz, 1H), 7.25 (d, J=8.8 Hz, 1H), 7.23 (s, 1H), 6.56 (s, 1H), 4.18, 4.50 (2m, 2H), 3.91 (s, 3H), 3.22, 3.40 (2m, 3H).

MS m/z (+ESI): 314.0 [M+H]$^+$.

Preparation of 3-oxo-3,4-dihydro-2H-benzo[1,4]thiazine-6-carboxylic acid [4-(6-methoxy-3,4-dihydro-2H-1-oxa-9-aza-phenanthren-3-yl)-thiazol-2-yl]-amide The titled compound is prepared as a white lyophilized powder following Scheme 1 and in analogy to Example 1 using 3-oxo-3,4-dihydro-2H-benzo[1,4]thiazine-6-carboxylic acid and 4-(6-methoxy-3,4-dihydro-2H-1-oxa-9-aza-phenanthren-3-yl)-thiazol-2-ylamine as starting materials.

$^1$H-NMR (400 MHz, DMSO-d6) δ ppm: 12.74 (br, 1H), 10.82 (s, 1H), 8.40 (s, 1H), 7.87 (m, 1H), 7.76 (dd, J=1.9, 8.2 Hz, 1H), 7.63 (d, J=1.8 Hz, 1H), 7.49 (d, J=7.5 Hz, 1H), 7.24 (m, 2H), 7.19 (s, 1H), 4.61 (m, 1H), 4.25 (m, 1H), 3.94 (s, 3H), 3.45-3.60 (m, 5H).

MS m/z (+ESI): 505.4 [M+H]$^+$.

Example 76

3-oxo-3,4-dihydro-2H-benzo[1,4]thiazine-6-carboxylic acid [trans-4-(6-methoxy-1,2,3,4-tetrahydro-1,5,9-triaza-phenanthren-3-yl)-cyclohexyl]-amide Preparation of 3-chloro-6-methoxy-[1,5]naphthyridine-4-carboxylic acid amide 3-Chloro-6-methoxy-[1,5]naphthyridine-4-carbonitrile (5.0 g, 22.8 mmol, 1.0 eq) is suspended in a 10% sodium hydroxide aqueous solution (125 mL) and the resulting mixture is heated to reflux for 30 minutes. The reaction mixture is then extracted with ethyl acetate (3×100 mL) and the pH is adjusted to 3-4 by the addition of a 3N hydrochloric acid aqueous solution. The combined organic layers are dried over sodium sulfate, filtered and concentrated to give the crude product that is purified by column chromatography (silica gel, eluent: ethyl acetate:petroleum ether, 1:1 to 4:1, v/v) to afford 3-chloro-6-methoxy-[1,5]naphthyridine-4-carboxylic acid amide as an off-white solid (3.44 g, 64% yield).

$^1$H-NMR (400 MHz, DMSO-d6) δ ppm: 8.83 (s, 1H), 8.30 (d, J=8.8 Hz, 1H), 7.93 and 8.05 (2s, 2H), 7.30 (d, J=8.8 Hz, 1H), 3.97 (s, 3H).

MS m/z (+ESI): 238.2 [M+H]$^+$.

Preparation of 3-chloro-6-methoxy-[1,5]naphthyridine-4-carbaldehyde

Bis(cyclopentadienyl)zirconium hydrochloride (814 mg, 3.2 mmol, 1.5 eq) is added at room temperature to a stirred solution of 3-chloro-6-methoxy-[1,5]naphthyridine-4-carboxylic acid amide (500 mg, 2.1 mmol, 1.0 eq) in tetrahydrofuran (35 mL). After 10 minutes stirring at room temperature, the reaction mixture is filtered through decalite, concentrated and purified by column chromatography (silica gel, eluent: ethyl acetate:petroleum ether, 1:8, v/v) to afford 3-chloro-6-methoxy-[1,5]naphthyridine-4-carbaldehyde as an off-white solid (185 mg, 28% yield).

$^1$H-NMR (400 MHz, $CDCl_3$) δ ppm: 11.24 (s, 1H), 8.82 (s, 1H), 8.25 (d, J=9.2 Hz, 1H), 7.19 (d, J=9.6 Hz, 1H), 4.10 (s, 3H).

MS m/z (+ESI): 223.1 [M+H]$^+$.

Preparation of {trans-4-[2-(3-chloro-6-methoxy-[1,5]naphthyridin-4-yl)-1-formyl-2-hydroxy-ethyl]-cyclohexyl}-carbamic acid tert-butyl ester A solution of [trans-4-(2-oxo-ethyl)-cyclohexyl]-carbamic acid tert-butyl ester (3.1 g, 25.1 mmol, 1.0 eq), 3-chloro-6-methoxy-[1,5]naphthyridine-4-carbaldehyde (5.6 g, 25.1 mmol, 1.0 eq) and L-proline (1.16 mg, 10.1 mmol, 0.4 eq) in dimethyl sulfoxide (100 mL) and water (15 mL) is stirred at room temperature for 16 hours. The reaction mixture is then extracted with ethyl acetate (500 mL) and water (500 mL). The organic layer is washed with brine (300 mL), dried over magnesium sulfate, filtered and concentrated to give a residue that is purified by column chromatography (silica gel, eluent: ethyl acetate:petroleum ether, 1:1, v/v) to afford {trans-4-[2-(3-chloro-6-methoxy-[1,5]naphthyridin-4-yl)-1-formyl-2-hydroxy-ethyl]-cyclohexyl}-carbamic acid tert-butyl ester as a light yellow solid (4.5 g, 39% yield).

$^1$H-NMR (400 MHz, $CDCl_3$) δ ppm: 9.85 (d, J=4.0 Hz, 1H), 8.72 (s, 1H), 8.25 (d, J=8.4 Hz, 1H), 7.15 (m, 2H), 5.86 (dd, J=4.8, 10.0 Hz, 1H), 4.37 (br, 1H), 4.01 (s, 3H), 3.38 (m, 1H), 2.62 (m, 1H), 1.10-2.07 (m, 9H), 1.43 (s, 9H).

MS m/z (+ESI): 464.2 [M+H]$^+$.

Preparation of {trans-4-[2-(3-chloro-6-methoxy-[1,5]naphthyridin-4-yl)-1-formyl-vinyl]-cyclohexyl}-carbamic acid tert-butyl ester Acetic anhydride (9.95 g, 97.5 mmol, 10.0 eq) is added at room temperature to a stirred solution of {trans-4-[2-(3-chloro-6-methoxy-[1,5]naphthyridin-4-yl)-1-formyl-2-hydroxy-ethyl]-cyclohexyl}-carbamic acid tert-butyl ester (4.5 g, 9.7 mmol, 1.0 eq) in anhydrous pyridine (100 mL). After 30 hours stirring at room temperature and 90 hours stirring at 50° C., solvent is removed and the residue is extracted with ethyl acetate (3×100 mL) and a saturated sodium hydrogen carbonate aqueous solution (100 mL). The combined organic layers are dried over sodium sulfate, filtered and concentrated to give the crude product that is purified by column chromatography (silica gel, eluent: petroleum ether:ethyl acetate:

dichloromethane, 9:2:1 to 6:2:1, v/v/v) to afford {trans-4-[2-(3-chloro-6-methoxy-[1,5]naphthyridin-4-yl)-1-formyl-vinyl]-cyclohexyl}-carbamic acid tert-butyl ester as a white solid (3.40 g, 79% yield).

$^1$H-NMR (400 MHz, $CDCl_3$) δ ppm: 9.37 (s, 1H), 8.76 (s, 1H), 8.19 (d, J=8.8 Hz, 1H), 7.33 (s, 1H), 7.13 (d, J=9.2 Hz, 1H), 4.47 (br, 1H), 3.87 (s, 3H), 3.50 (m, 1H), 2.72 (t, J=12.0 Hz, 1H), 1.10-2.20 (m, 8H), 1.45 (s, 9H).

MS m/z (+ESI): 446.1 $[M+H]^+$.

Preparation of {trans-4-[1-(benzylamino-methyl)-2-(3-chloro-6-methoxy-[1,5]naphthyridin-4-yl)-vinyl]-cyclohexyl}-carbamic acid tert-butyl ester Benzylamine (360 mg, 3.36 mmol, 3.0 eq) is added at room temperature to a stirred solution of {trans-4-[2-(3-chloro-6-methoxy-[1,5]naphthyridin-4-yl)-1-formyl-vinyl]-cyclohexyl}-carbamic acid tert-butyl ester (500 mg, 1.12 mmol, 1.0 eq) in ethanol (20 mL), followed by acetic acid (337 mg, 5.61 mmol, 5.0 eq) and sodium cyanoborohydride (352 mg, 5.61 mmol, 5.0 eq). After 2 hours stirring at room temperature, the reaction mixture is extracted with ethyl acetate (3×20 mL) and a saturated sodium hydrogen carbonate aqueous solution (20 mL). The combined organic layers are dried over sodium sulfate, filtered and concentrated to give a residue that is purified by column chromatography (silica gel, eluent: ethyl acetate:petroleum ether, 3:1 to 1:1, v/v) to afford {trans-4-[1-(benzylamino-methyl)-2-(3-chloro-6-methoxy-[1,5]naphthyridin-4-yl)-vinyl]-cyclohexyl}-carbamic acid tert-butyl ester as a light yellow solid (320 mg, 53% yield).

$^1$H-NMR (400 MHz, $CDCl_3$) δ ppm: 8.69 (s, 1H), 8.21 (d, J=9.2 Hz, 1H), 6.90-7.26 (m, 6H), 6.54 (s, 1H), 4.55 (m, 2H), 3.83 (s, 3H), 3.74 (s, 2H), 3.47 (br, 1H), 3.32 (s, 2H), 2.50 (m, 1H), 2.00-2.20 (m, 4H), 1.35-1.55 (m, 4H), 1.43 (s, 9H).

MS m/z (+ESI): 537.2 $[M+H]^+$.

Preparation of [trans-4-(1-benzyl-6-methoxy-1,2-dihydro-1,5,9-triaza-phenanthren-3-yl)-cyclohexyl]-carbamic acid tert-butyl ester A solution of sodium hydroxide (500 mg, 12.5 mmol, 33.6 eq) in water (6 mL) is added at room temperature to a stirred solution of {trans-4-[1-(benzylamino-methyl)-2-(3-chloro-6-methoxy-[1,5]naphthyridin-4-yl)-vinyl]-cyclohexyl}-carbamic acid tert-butyl ester (200 mg, 0.37 mmol, 1.0 eq) in tetrahydrofuran (6 mL). After 16 hours stirring at 60° C., tetrahydrofuran is removed and the residue is extracted with ethyl acetate (3×10 mL). The combined organic layers are dried over sodium sulfate, filtered and concentrated to give the crude product that is purified by column chromatography (silica gel, eluent: petroleum ether:ethyl acetate, 5:1 to 3:1, v/v) to afford [trans-4-(1-benzyl-6-methoxy-1,2-dihydro-1,5,9-triaza-phenanthren-3-yl)-cyclohexyl]-carbamic acid tert-butyl ester as a light yellow solid (110 mg, 59% yield).

$^1$H-NMR (400 MHz, $CDCl_3$) δ ppm: 8.23 (s, 1H), 7.93 (d, J=8.8 Hz, 1H), 7.10-7.40 (m, 6H), 6.79 (d, J=8.8 Hz, 1H), 4.40 (br, 1H), 4.19 (s, 2H), 4.09 (s, 3H), 3.93 (s, 2H), 3.45 (m, 1H), 3.05 (s, 1H), 1.10-2.20 (m, 8H), 1.43 (s, 9H).

MS m/z (+ESI): 501.3 $[M+H]^+$.

Preparation of [trans-4-(6-methoxy-1,2,3,4-tetrahydro-1,5,9-triaza-phenanthren-3-yl)-cyclohexyl]-carbamic acid tert-butyl ester 10% Palladium on activated carbon (1.20 g, 1.13 mmol, 0.94 eq) is added at room temperature to a stirred solution of [trans-4-(1-benzyl-6-methoxy-1,2-dihydro-1,5,9-triaza-phenanthren-3-yl)-cyclohexyl]-carbamic acid tert-butyl ester (600 mg, 1.20 mmol, 1.0 eq) in ethanol (60 mL). The resulting mixture is stirred under hydrogen flow (1 bar) at 60° C. for 3 hours. The catalyst is then removed by filtration and the solution is concentrated to give the crude product that is purified by column chromatography (silica gel, eluent: petroleum ether:ethyl acetate: dichloromethane, 1:3:1, v/v/v) to afford [trans-4-(6-methoxy-1,2,3,4-tetrahydro-1,5,9-triaza-phenanthren-3-yl)-cyclohexyl]-carbamic acid tert-butyl ester as an off-white solid (292 mg, 59% yield).

$^1$H-NMR (400 MHz, $CDCl_3$) δ ppm: 8.13 (s, 1H), 7.99 (d, J=8.8 Hz, 1H), 6.79 (d, J=8.8 Hz, 1H), 4.38 (br, 1H), 4.22 (br, 1H), 4.05 (s, 3H), 3.40-3.48 (m, 3H), 3.09 (m, 1H), 2.70 (m, 1H), 1.05-2.10 (m, 10H), 1.45 (s, 9H).

MS m/z (+ESI): 413.4 $[M+H]^+$.

Preparation of 3-oxo-3,4-dihydro-2H-benzo[1,4]thiazine-6-carboxylic acid [trans-4-(6-methoxy-1,2,3,4-tetrahydro-1,5,9-triaza-phenanthren-3-yl)-cyclohexyl]-amide The titled compound is prepared as an off-white lyophilizated powder following Scheme 8 and in analogy to Example 1 using [trans-4-(6-methoxy-1,2,3,4-tetrahydro-1,5,9-triaza-phenanthren-3-yl)-cyclohexyl]-carbamic acid tert-butyl ester and 3-oxo-3,4-dihydro-2H-benzo[1,4]thiazine-6-carboxylic acid as starting materials.

$^1$H-NMR (400 MHz, DMSO-d6) δ ppm: 10.67 (s, 1H), 8.23 (d, J=7.9 Hz, 1H), 8.17 (s, 1H), 7.96 (d, J=8.8 Hz, 1H), 7.44 (m, 3H), 6.78 (d, J=8.8 Hz, 1H), 6.56 (d, J=2.4 Hz, 1H), 3.99 (s, 3H), 3.76 (m, 1H), 3.52 (s, 2H), 3.42 (m, 2H), 2.99 (m, 1H), 2.58 (m, 1H), 1.97 (m, 4H), 1.62 (m, 1H), 1.29 (m, 5H).

MS m/z (+ESI): 504.5 $[M+H]^+$.

The examples listed in the following table are prepared using procedures previously described:

| Example Number | Reference Scheme | Reference for Preparation | 1H-NMR (400 MHz, DMSO- d6) δ ppm | MS m/z (+ESI) |
|---|---|---|---|---|
| 5 | 1 | Examples 2 & 3 | 10.51 (br, 1H), 8.38 (s, 1H), 7.83 (d, J = 9.0 Hz, 1H), 7.25 (m, 3H), 6.97 (m, 2H), 3.97 (s, 3H), 3.68 (s, 2H), 3.42 (s, 2H), 3.31 (s, 2H), 2.98-3.27 (m, 5H), 2.86 (m, 1H), 2.39 (m, 1H), 2.29 (m, 1H), 1.83 (m, 2H), 1.29 (m, 2H) | 507.6 $[M + H]^+$ |
| 6 | 1 | Example 1 | 10.80 (br, 1H), 8.32 (s, 1H), 8.18 (d, J = 7.8 Hz, 1H), 7.82 (d, J = 9.0 Hz, 1H), 7.35-7.48 (m, 2H), 7.21 (m, 2H), 6.98 (d, J = 8.3 Hz, 1H), 4.63 (s, 2H), | 489.6 $[M + H]^+$ |

-continued

| Example Number | Reference Scheme | Reference for Preparation | 1H-NMR (400 MHz, DMSO- d6) δ ppm | MS m/z (+ESI) |
|---|---|---|---|---|
| | | | 4.45 (d, J = 11.4 Hz, 1H), 4.03 (m, 1H), 3.93 (s, 3H), 3.79 (m, 1H), 3.23 (m, 1H), 3.10 (m, 2H), 3.03 (m, 2H), 2.44 (m, 2H), 1.81 (m, 2H), 1.56 (m, 2H) | |
| 7 | 1 | Example 1 | 11.02 (br, 1H), 8.34 (s, 1H), 8.02 (d, J = 8.1 Hz, 1H), 7.97 (m, 1H), 7.82 (d, J = 9.0 Hz, 1H), 7.59 (m, 1H), 7.23 (m, 2H), 4.48 (d, J = 10.9 Hz, 1H), 4.05 (m, 1H), 3.93 (s, 3H), 3.82 (m, 1H), 3.63 (s, 2H), 3.23 (m, 1H), 3.05 (m, 4H), 2.52 (m, 2H), 1.88 (m, 2H), 1.52 (m, 2H) | 506.6 $[M + H]^+$ |
| 8 | 1 | Example 1 | 8.33 (s, 1H), 7.98 (d, J = 7.8 Hz, 1H), 7.82 (d, J = 9.0 Hz, 1H), 7.20 (m, 2H), 6.99 (s, 1H), 6.92 (m, 2H), 6.19 (br, 1H), 4.44 (d, J = 11.4 Hz, 1H), 4.02 (m, 1H), 3.94 (s, 3H), 3.75 (m, 1H), 3.48 (m, 2H), 3.22 (m, 1H), 3.09 (m, 2H), 3.00 (m, 4H), 2.42 (m, 2H), 1.80 (m, 2H), 1.57 (m, 2H) | 491.6 $[M + H]^+$ |
| 9 | 1 | Example 1 | 8.33 (s, 1H), 8.15 (d, J = 7.8 Hz, 1H), 7.82 (d, J = 9.0 Hz, 1H), 7.20 (s, 1H), 6.99 (s, 1H), 6.92 (m, 2H), 6.19 (br, 1H), 4.44 (d, J = 11.4 Hz, 1H), 4.02 (m, 1H), 3.94 (s, 3H), 3.75 (m, 1H), 3.48 (m, 2H), 3.22 (m, 1H), 3.09 (m, 2H), 3.00 (m, 4H), 2.42 (m, 2H), 1.80 (m, 2H), 1.57 (m, 2H) | 525.6 $[M + H]^+$ |
| 10 | 1 | Examples 1 & 3 | — | 521.6 $[M + H]^+$ |
| 11 | 1 | Examples 2 & 3 | 11.17 (br, 1H), 8.38 (s, 1H), 7.82 (d, J = 9.0 Hz, 1H), 7.27 (m, 3H), 7.04 (d, J = 8.1 Hz, 1H), 4.61 (s, 2H), 3.91 (s, 3H), 3.70 (s, 2H), 2.98-3.28 (m, 7H), 2.88 (m, 1H), 2.42 (m, 1H), 2.30 (m, 1H), 1.86 (m, 2H), 1.31 (m, 2H) | 492.6 $[M + H]^+$ |
| 12 | 3 | Examples 2 & 4 | 10.55 (s, 1H), 8.36 (s, 1H), 7.48 (d, J = 9.2 Hz, 1H), 7.20 (m, 5H), 6.93 (m, 2H), 4.89 (m, 1H), 4.40 (m, 2H), 4.00 (s, 2H), 3.89 (s, 3H), 3.51 (m, 2H), 3.42 (s, 2H) | 474.3 $[M + H]^+$ |
| 14 | 1 | Example 1 | 8.72 (d, J = 8.0 Hz, 1H), 8.38 (s, 1H), 7.87 (dd, J = 1.1, 5.0 Hz, 1H), 7.78 (m, 2H), 7.57 (t, J = 9.0 Hz, 1H), 7.27 (dd, J = 3.7, 5.0 Hz, 1H), 7.18 (s, 1H), 4.44 (m, 1H), 4.08 (m, 1H), 3.97 (s, 3H), 3.80 (m, 1H), 3.40 (m, 1H), 3.23 (m, 1H), 3.08 (m, 1H), 3.00 (m, 2H), 2.31-2.47 (m, 2H), 1.80 (m, 2H), 1.61 (m, 2H) | 509.4 $[M + H]^+$ |
| 16 | 6 | Example 1 | — | 488.3 $[M + H]^+$ |
| 17 | 6 | Examples 1 & 2 | — | 475.3 $[M + H]^+$ |
| 18 | 6 | Examples 1 & 2 | 10.50 (s, 1H), 8.31 (s, 1H), 7.81 (d, J = 9.8 Hz, 1H), 7.20 (m, 3H), 6.97 (m, 2H), 4.40 (m, 1H), 3.92 (s, 3H), 3.85 (m, 1H), 3.68 (s, 2H), 3.57 (s, 2H), 3.09 (m, 1H), 2.71 (m, 1H), 2.35 (m, 1H), 1.98 (m, 3H), 1.88 (m, 2H), 1.33 (m, 1H), 0.95-1.20 (m, 4H) | 490.2 $[M + H]^+$ |
| 19 | 1 | Examples 1 & 3 | — | 506.5 $[M + H]^+$ |
| 21 | 6 | Example 1 | 10.65 (s, 1H), 8.33 (s, 1H), 8.23 (d, J = 7.9 Hz, 1H), 7.82 (d, J = 8.9 Hz, 1H), 7.37-7.48 (m, 3H), | 504.2 $[M + H]^+$ |

-continued

| Example Number | Reference Scheme | Reference for Preparation | 1H-NMR (400 MHz, DMSO- d6) δ ppm | MS m/z (+ESI) |
|---|---|---|---|---|
| | | | 7.20 (m, 2H), 4.44 (m, 1H), 3.93 (s, 3H), 3.88 (m, 1H), 3.78 (m, 1H), 3.50 (s, 2H), 3.12 (m, 1H), 2.76 (m, 1H), 2.03 (m, 1H), 1.92 (m, 4H), 1.20-1.42 (m, 5H) | |
| 22 | 1 | Example 1 | 8.37 (s, 1H), 7.97 (d, J = 7.8 Hz, 1H), 7.77 (dd, J = 1.3, 9.2 Hz, 1H), 7.56 (d, J = 8.9 Hz, 1H), 6.99 (d, J = 1.4 Hz, 1H), 6.91 (m, 2H), 6.19 (s, 1H), 4.44 (m, 1H), 4.07 (m, 1H), 3.97 (s, 3H), 3.74 (m, 1H), 3.47 (m, 2H), 3.38 (m, 1H), 3.23 (m, 1H), 3.07 (m, 1H), 2.98 (m, 4H), 2.38 (m, 2H), 1.97 (m, 2H), 1.53 (m, 2H) | 509.2 $[M + H]^+$ |
| 23 | 1 | Example 1 | 11.01 (s, 1H), 8.38 (s, 1H), 8.01 (d, J = 8.1 Hz, 1H), 7.95 (d, J = 7.9 Hz, 1H), 7.77 (dd, J = 1.3, 9.2 Hz, 1H), 7.57 (m, 2H), 4.46 (m, 1H), 4.08 (m, 1H), 3.97 (s, 3H), 3.80 (m, 1H), 3.64 (s, 2H), 3.41 (m, 1H), 3.24 (m, 1H), 2.90-3.10 (m, 3H), 2.40-2.58 (m, 2H), 1.88 (m, 2H), 1.52 (m, 2H) | 524.2 $[M + H]^+$ |
| 24 | 1 | Example 1 | 8.38 (s, 1H), 7.91 (d, J = 8.2 Hz, 1H), 7.77 (dd, J = 1.4, 9.2 Hz, 1H), 7.56 (t, J = 8.9 Hz, 1H), 7.40 (d, J = 7.7 Hz, 1H), 7.10 (d, J = 7.7 Hz, 1H), 6.97 (br, 1H), 4.45 (m, 1H), 4.08 (m, 1H), 3.97 (s, 3H), 3.74 (m, 1H), 3.62 (m, 2H), 3.35-3.45 (m, 1H), 3.18-3.28 (m, 1H), 2.92-3.07 (m, 5H), 2.43 (m, 2H), 1.85 (m, 2H), 1.50 (m, 2H) | 510.2 $[M + H]^+$ |
| 25 | 1 | Example 1 | 8.38 (s, 1H), 8.36 (s, 1H), 8.12 (d, J = 0.5 Hz, 1H), 7.83 (d, J = 5.3 Hz, 1H), 7.78 (dd, J = 1.6, 9.2 Hz, 1H), 7.57 (t, J = 9.0 Hz, 1H), 7.48 (dd, J = 0.6, 5.3 Hz, 1H), 4.45 (m, 1H), 4.09 (m, 1H), 3.97 (s, 3H), 3.77 (m, 1H), 3.40 (m, 1H), 3.25 (m, 1H), 3.10 (m, 1H), 3.00 (m, 2H), 2.33-2.48 (m, 2H), 1.85 (m, 2H), 1.56 (m, 2H) | 498.1 $[M + H]^+$ |
| 26 | 1 | Example 1 | 10.80 (s, 1H), 8.38 (s, 1H), 8.14 (d, J = 7.8 Hz, 1H), 7.77 (dd, J = 1.6, 9.2 Hz, 1H), 7.57 (t, J = 9.0 Hz, 1H), 7.42 (m, 2H), 6.98 (d, J = 8.3 Hz, 1H), 4.62 (s, 2H), 4.45 (m, 1H), 4.08 (m, 1H), 3.97 (s, 3H), 3.76 (m, 1H), 3.39 (m, 1H), 3.22 (m, 1H), 3.08 (m, 1H), 2.98 (m, 2H), 2.33-2.47 (m, 2H), 1.80 (m, 2H), 1.54 (m, 2H) | 507.2 $[M + H]^+$ |
| 28 | 5 | Example 27 | — | 501.1 $[M + H]^+$ |
| 29 | 6 | Example 1 | 11.35 (br, 1H), 8.33 (s, 1H), 7.82 (d, J = 9.2 Hz, 1H), 7.75 (d, J = 8.3 Hz, 1H), 7.61 (d, J = 8.1 Hz, 1H), 7.46 (d, J = 8.1 Hz, 1H), 7.20 (m, 2H), 4.73 (s, 2H), 4.44 (m, 1H), 3.93 (s, 3H), 3.87 (m, 1H), 3.75 (m, 1H), 3.13 (m, 1H), 2.76 (m, 1H), 1.86-2.08 (m, 5H), 1.23-1.48 (m, 5H) | 489.3 $[M + H]^+$ |
| 30 | 6 | Example 1 | 8.33 (s, 1H), 7.97 (d, J = 8.0 Hz, 1H), 7.82 (d, J = 8.9 Hz, 1H), 7.20 (m, 2H), 6.95 (m, 3H), 6.18 (br, 1H), 4.44 (m, 1H), 3.93 (s, 3H), 3.89 (m, 1H), 3.75 (m, 1H), 3.47 (m, 2H), 3.13 (m, 1H), 3.00 (m, 2H), 2.75 (m, 1H), 2.02 (m, 1H), 1.91 (m, 4H), 1.20-1.44 (m, 5H) | 490.2 $[M + H]^+$ |
| 31 | 3 | Example 4 | 10.98 (s, 1H), 8.40 (s, 1H), 8.18 (s, 1H), 7.82-7.88 (m, 3H), 7.74 (s, 1H) , 7.20-7.30 (m, 4H), 5.12 | 474.5 $[M + H]^+$ |

-continued

| Example Number | Reference Scheme | Reference for Preparation | 1H-NMR (400 MHz, DMSO- d6) δ ppm | MS m/z (+ESI) |
|---|---|---|---|---|
| | | | (m, 1H), 4.50 (m, 2H), 3.92 (s, 3H), 3.62 (m, 2H) | |
| 32 | 3 | Example 4 | 10.25 (s, 1H), 8.40 (s, 1H), 8.12 (s, 1H), 7.87 (d, J = 8.9 Hz, 1H), 7.68 (s, 1H), 7.46 (m, 2H), 7.23 (m, 2H), 6.95 (d, J = 8.3 Hz, 1H), 5.08 (m, 1H), 4.50 (m, 2H), 4.28 (m, 4H), 3.91 (s, 3H), 3.60 (m, 2H) | 459.5 $[M + H]^+$ |
| 33 | 3 | Example 4 | 10.60 (s, 1H), 8.40 (s, 1H), 8.18 (s, 1H), 8.10 (s, 1H), 7.87 (m, 2H), 7.69 (s, 1H), 7.50 (d, J = 5.3 Hz, 1H), 7.23 (m, 2H), 5.11 (m, 1H), 4.52 (m, 2H), 3.92 (s, 3H), 3.60 (m, 2H) | 463.4 $[M + H]^+$ |
| 34 | 1 | Example 1 | 11.37 (s, 1H), 8.38 (s, 1H), 7.83 (d, J = 8.0 Hz, 1H), 7.78 (d, J = 9.2 Hz, 1H), 7.58 (m, 2H), 7.46 (d, J = 8.1 Hz, 1H), 4.73 (s, 2H), 4.46 (m, 1H), 4.08 (m, 1H), 3.97 (s, 3H), 3.78 (m, 1H), 3.41 (m, 1H), 3.24 (m, 1H), 2.90-3.10 (m, 3H), 2.40-2.50 (m, 2H), 1.88 (m, 2H), 1.53 (m, 2H) | 508.5 $[M + H]^+$ |
| 36 | 5 | Example 27 | 10.63 (s, 1H), 8.20 (d, J = 8.2 Hz, 1H), 8.15 (s, 1H), 8.01 (d, J = 9.0 Hz, 1H), 7.43 (m, 2H), 7.37 (m, 1H), 7.02 (d, J = 9.0 Hz, 1H), 6.86 (d, J = 3.3 Hz, 1H), 4.34 (dd, J = 3.3, 11.0 Hz, 1H), 4.07 (m, 1H), 4.04 (s, 3H), 3.75 (m, 1H), 3.49 (s, 2H), 3.43 (m, 1H), 1.88 (m, 4H), 1.57 (m, 1H), 1.29 (m, 4H) | 506.4 $[M + H]^+$ |
| 38 | 6 | Example 15 | — | 505.3 $[M + H]^+$ |
| 39 | 6 | Examples 2 & 15 | — | 491.4 $[M + H]^+$ |
| 40 | 6 | Example 15 | — | 491.4 $[M + H]^+$ |
| 41 | 5 | Example 27 | 8.65 (d, J = 8.2 Hz, 1H), 8.15 (s, 1H), 8.02 (d, J = 9.0 Hz, 1H), 7.86 (dd, J = 1.1, 5.0 Hz, 1H), 7.78 (dd, J = 1.0, 3.6 Hz, 1H), 7.26 (dd, J = 3.8, 4.9 Hz, 1H), 7.17 (s, 1H), 7.02 (d, J = 9.0 Hz, 1H), 6.86 (d, J = 3.2 Hz, 1H), 4.34 (dd, J = 3.3, 11.0 Hz, 1H), 4.07 (m, 1H), 4.04 (s, 3H), 3.78 (m, 1H), 3.44 (m, 1H), 1.90 (m, 4H), 1.58 (m, 1H), 1.33 (m, 4H) | 492.4 $[M + H]^+$ |
| 42 | 1 | Example 1 | — | 491.4 $[M + H]^+$ |
| 45 | 6 | Examples 2 & 15 | 10.48 (s, 1H), 8.67 (d, J = 2.8 Hz, 1H), 8.64 (s, 1H), 7.91 (d, J = 9.1 Hz, 1H), 7.30 (dd, J = 2.8, 9.1 Hz, 1H), 7.21 (d, J = 7.9 Hz, 1H), 6.93 (m, 2H), 4.74 (m, 2H), 3.91 (s, 3H), 3.66 (s, 2H), 3.41 (s, 2H), 2.58 (m, 1H), 2.30 (m, 1H), 1.08, 1.53, 1.88 (3m, 9H) | 504.5 $[M + H]^+$ |
| 46 | 1 | Example 1 | 11.36 (br, 1H), 8.34 (s, 1H), 7.85 (m, 2H), 7.61 (d, J = 8.1 Hz, 1H), 7.46 (d, J = 8.2 Hz, 1H), 7.22 (m, 2H), 4.73 (s, 2H), 4.46 (m, 1H), 4.04 (m, 2H), 3.94 (s, 3H), 3.79 (m, 1H), 3.21 (m, 1H), 3.04 (m, 4H), 2.58 (m, 1H), 1.89 (m, 2H), 1.54 (m, 2H) | 490.5 $[M + H]^+$ |
| 51 | 6 | Example 15 | 11.34 (br, 1H), 8.52 (s, 1H), 7.97 (m, 2H), 7.77 (d, J = 8.3 Hz, 1H), 7.60 (m, 3H), 7.47 (m, 1H), 4.74 (s, 2H), 4.47 (m, 1H), 3.94 (t, J = 10.3 Hz, 1H), 3.77 (m, 1H), 3.20 (m, 1H), 2.84 (m, 1H), 1.97 (m, 5H), 1.30 (m, 5H) | 459.5 $[M + H]^+$ |
| 52 | 6 | Example 15 | — | 476.5 $[M + H]^+$ |
| 53 | 6 | Example 15 | — | 477.5 $[M + H]^+$ |
| 54 | 6 | Examples 2 & 15 | — | 478.5 $[M + H]^+$ |
| 55 | 6 | Example 15 | — | 458.5 $[M + H]^+$ |

-continued

| Example Number | Reference Scheme | Reference for Preparation | 1H-NMR (400 MHz, DMSO- d6) δ ppm | MS m/z (+ESI) |
|---|---|---|---|---|
| 56 | 1 | Example 1 | 8.38 (s, 1H), 8.04 (d, J = 7.8 Hz, 1H), 7.77 (dd, J = 1.5, 9.2 Hz, 1H), 7.56 (t, J = 9.0 Hz, 1H), 7.37 (m, 2H), 6.89 (d, J = 8.3 Hz, 1H), 4.45 (m, 1H), 4.27 (m, 4H), 4.06 (m, 1H), 3.97 (s, 3H), 3.76 (m, 1H), 3.39 (m, 1H), 3.22 (m, 1H), 3.07 (m, 1H), 2.98 (m, 2H), 2.30-2.45 (m, 2H), 1.79 (m, 2H), 1.54 (m, 2H) | 494.2 $[M + H]^+$ |
| 57 | 3 | Examples 2 & 4 | — | 443.4 $[M + H]^+$ |
| 58 | 3 | Examples 2 & 4 | — | 455.4 $[M + H]^+$ |
| 59 | 3 | Examples 2 & 4 | — | 437.4 $[M + H]^+$ |
| 60 | 1 | Example 1 | 11.34 (br, 1H), 8.35 (2s, 1H), 7.97 (m, 1H), 7.83 (m, 1H), 7.61 (2s, 1H), 7.46 (2d, J = 8.2 Hz, 1H), 7.21 (m, 2H), 4.73 (2s, 2H), 4.46 (m, 2H), 4.00 (m, 1H), 3.92 (2s, 3H), 3.27 (m, 1H), 3.02 (m, 2H), 2.67 (m, 2H), 2.27 (m, 1H), 1.67 (m, 1H), 1.54 (m, 2H) | 476.4 $[M + H]^+$ |
| 61 | 6 | Example 15 | — | 492.5 $[M + H]^+$ |
| 64 | 3 | Example 4 | 10.75 (s, 1H), 10.45 (s, 1H), 8.49 (s, 1H), 8.22 (d, J = 9.0 Hz, 1H), 8.15(s, 1H), 7.69(d, J = 0.5 Hz, 1H), 7.54 (m, 2H), 7.47 (d, J = 8.0 Hz, 1H), 7.13 (d, J = 9.0 Hz, 1H), 5.09 (m, 1H), 4.56 (m, 2H), 4.03 (s, 3H), 3.67 (m, 2H), 3.54 (s, 2H) | 489.5 $[M + H]^+$ |
| 65 | 3 | Example 4 | 10.89 (s, 1H), 10.36 (s, 1H), 8.49 (s, 1H), 8.22 (d, J = 9.0 Hz, 1H), 8.13 (s, 1H), 7.68 (s, 1H), 7.54 (dd, J = 2.1, 8.4 Hz, 1H), 7.47 (d, J = 2.0 Hz, 1H), 7.13 (d, J = 9.0 Hz, 1H), 7.05 (d, J = 8.4 Hz, 1H), 5.09 (m, 1H), 4.66 (s, 2H), 4.56 (m, 2H), 4.03 (s, 3H), 3.67 (m, 2H) | 473.5 $[M + H]^+$ |
| 66 | 3 | Example 4 | 11.27 (br, 1H), 10.12 (s, 1H), 8.49 (s, 1H), 8.22 (m, 2H), 7.74 (d, J = 0.6 Hz, 1H), 7.67 (d, J = 8.2 Hz, 1H), 7.51 (d, J = 8.2 Hz, 1H), 7.13 (d, J = 9.0 Hz, 1H), 5.10 (m, 1H), 4.77 (s, 2H), 4.57 (m, 2H), 4.03 (s, 3H), 3.68 (m, 2H) | 474.5 $[M + H]^+$ |
| 67 | 6 | Example 63 | 10.66 (s, 1H), 8.35 (s, 1H), 8.24 (d, J = 8.0 Hz, 1H), 7.85 (d, J = 9.0 Hz, 1H), 7.38-7.48 (m, 3H), 7.24 (m, 2H), 4.46 (m, 1H), 4.25 (m, 2H), 3.90 (m, 1H), 3.79 (m, 1H), 3.51 (s, 2H), 3.14 (m, 1H), 2.70-2.80 (m, 3H), 2.12 (m, 2H), 2.05 (m, 1H), 1.94 (m, 4H), 1.25-1.45 (m, 5H) | 557.6 $[M + H]^+$ |
| 68 | 6 | Example 63 | 10.66 (s, 1H), 8.34 (s, 1H), 8.24 (d, J = 7.9 Hz, 1H), 7.83 (d, J = 9.0 Hz, 1H), 7.38-7.48 (m, 3H), 7.24 (m, 2H), 4.46 (m, 1H), 4.30 (m, 2H), 3.90 (m, 1H), 3.75-3.85 (m, 3H), 3.51 (s, 2H), 3.37 (s, 3H), 3.15 (m, 1H), 2.76 (m, 1H), 2.07 (m, 1H), 1.93 (m, 4H), 1.25-1.45 (m, 5H) | 548.6 $[M + H]^+$ |
| 69 | 6 | Example 63 | 10.66 (s, 1H), 8.34 (s, 1H), 8.24 (d, J = 7.9 Hz, 1H), 7.83 (d, J = 8.9 Hz, 1H), 7.38-7.48 (m, 3H), 7.21 (m, 2H), 4.81 (t, J = 5.2 Hz, 1H), 4.45 (m, 1H), 4.22 (t, J = 4.2 Hz, 2H), 4.04 (dd, J = 4.9, 10.9, 2H), 3.88 (m, 1H), 3.70-3.80 (m, 3H), 3.51 (s, 2H), 3.13 (m, 1H), 2.77 (m, 1H), 2.03 (m, 3H), 1.90 (m, 4H), 1.25-1.45 (m, 7H) | 604.7 $[M + H]^+$ |
| 70 | 6 | Example 63 | 10.66 (s, 1H), 8.33 (s, 1H), 8.24 (d, J = 7.9 Hz, 1H), 7.82 (d, J = | 532.6 $[M + H]^+$ |

-continued

| Example Number | Reference Scheme | Reference for Preparation | 1H-NMR (400 MHz, DMSO- d6) δ ppm | MS m/z (+ESI) |
|---|---|---|---|---|
| | | | 9.1 Hz, 1H), 7.38-7.48 (m, 3H), 7.21 (m, 2H), 4.91 (m, 1H), 4.44 (m, 1H), 3.89 (m, 1H), 3.78 (m, 1H), 3.51 (s, 2H), 3.12 (m, 1H), 2.73 (m, 1H), 2.02 (m, 1H), 1.92 (m, 4H), 1.22-1.45 (m, 11H) | |
| 71 | 6 | Example 63 | 10.66 (s, 1H), 8.33 (s, 1H), 8.24 (d, J = 7.9 Hz, 1H), 7.83 (d, J = 9.4 Hz, 1H), 7.38-7.48 (m, 3H), 7.21 (m, 2H), 4.45 (m, 1H), 4.13 (m, 2H), 3.90 (m, 1H), 3.79 (m, 1H), 3.50 (s, 2H), 3.12 (m, 1H), 2.76 (m, 1H), 2.04 (m, 1H), 1.93 (m, 4H), 1.83 (m, 2H), 1.25-1.45 (m, 5H), 1.06 (t, J = 7.4 Hz, 3H) | 532.6 $[M + H]^+$ |
| 73 | 3 | Example 4 | 10.78 (s, 1H), 10.48 (s, 1H), 8.92 (d, J = 2.4 Hz, 1H), 8.48 (s, 1H), 8.19 (m, 2H), 7.64 (dd, J = 1.8, 8.1 Hz, 1H), 7.54 (m, 3H), 7.10 (d, J = 9.0 Hz, 1H), 4.61 (m, 1H), 4.30 (m, 1H), 4.01 (s, 3H), 3.45-3.65 (m, 5H) | 500.5 $[M + H]^+$ |
| 74 | 3 | Examples 2 & 4 | — | 475.5 $[M + H]^+$ |
| 75 | 6 | Example 63 | — | 547.6 $[M + H]^+$ |
| 77 | 3 | Example 4 | 10.73 (s, 1H), 10.19 (s, 1H), 8.43 (s, 1H), 7.89 (d, J = 9.0 Hz, 1H), 7.42-7.56 (m, 3H), 7.38 (m, 1H), 7.22-7.27 (m, 2H), 6.83 (t, J = 2.7 Hz, 1H), 6.22 (dd, J = 1.7, 2.9 Hz, 1H), 4.84 (m, 1H), 4.43 (m, 2H), 3.92 (s, 3H), 3.62 (m, 1H), 3.53 (s, 2H), 3.41 (m, 1H) | 487.4 $[M + H]^+$ |
| 78 | 5 | Examples 27 & 35 & 48 | 10.66 (s, 1H), 10.47 (s, 1H), 9.17 (d, J = 3.8 Hz, 1H), 8.45 (s, 1H), 8.22 (d, J = 7.9 Hz, 1H), 7.80 (d, J = 9.2 Hz, 1H), 7.71 (d, J = 2.4 Hz, 1H), 7.43 (m, 4H), 4.46 (dd, J = 2.5, 11.2 Hz, 1H), 4.08 (dd, J = 2.7, 11.2 Hz, 1H), 3.75 (m, 1H), 3.65 (m, 1H), 3.50 (s, 2H), 1.90 (m, 4H), 1.68 (m, 1H), 1.29 (m, 4H) | 491.2 $[M + H]^+$ |
| 79 | 6 | Example 63 | — | 548.6 $[M + H]^+$ |
| 80 | 3 | Examples 2 & 4 | — | 460.5 $[M + H]^+$ |
| 81 | 3 | Examples 2 & 4 | — | 459.5 $[M + H]^+$ |
| 82 | 5 | Example 27 | 10.65 (br, 1H), 8.22 (d, J = 8.0 Hz, 1H), 8.11 (s, 1H), 7.67 (d, J = 9.2 Hz, 1H), 7.50 (d, J = 2.7 Hz, 1H), 7.37-7.47 (m, 3H), 7.15 (dd, J = 2.7, 9.2 Hz, 1H), 7.08 (d, J = 3.6 Hz, 1H), 4.28 (m, 1H), 4.03 (m, 1H), 3.91 (s, 3H), 3.74 (m, 1H), 3.50 (s, 2H), 3.42 (m, 1H), 2.02 (m, 1H), 1.91 (m, 3H), 1.30 (m, 5H) | 505.5 $[M + H]^+$ |

Antimicrobial Activity Assay

The antibacterial activity of compounds is determined by the minimal inhibitory concentration (MIC) method. MICs for all bacteria except pneumococci and *Haemophilus influenzae* are obtained by broth microdilution with cation-adjusted Mueller-Hinton broth (CAMHB; BBL), according to CLSI guidelines (National Committee for Clinical Laboratory Standards. 2003. Methods for dilution antimicrobial susceptibility tests for bacteria that grow aerobically, $5^{th}$ ed.; a approved standard M7-A6. National Committee for Clinical Laboratory Standards, Wayne, Pa.), with the following modifications: (i) for *pneumococci* CAMHB is supplemented with 5% ($^v$/v) horse serum; (ii) for *Haemophilus influenzae* CAMHB is supplemented with 5% ($^v$/v) Fildes enrichment (BBL) (Pankuch, G. A., Hoellman, D. B., Lin, G., Bajaksouzian, S., Jacobs, M. R., and Appelbaum, P. C. 1998. Activity of HMR 3647 compared to those of five agents against *Haemophilus influenzae* and *Moraxella catarrhalis* by MIC determination and time-kill assay. Antimicrob. Agents Chemother. 42:3032-3034). Microtiter plates are incubated at 35° C. in ambient air for 20 to 24 h, then inspected using an illuminated microtiter plate reader fitted with a magnifying mirror (MIC 2000; Cooke Laboratory Products, Alexandria, Va.). Compounds of the present invention are tested against several bacteria strains comprising some *Acinetobacter baumannii, Enterococcus faecalis, Enterococcus faecium, Escherichia coli, Haemophilus influenzae, Klebsiella pneumoniae, Pseudomonas aeruginosa, Staphylococcus aureus, Staphylococcus epidermidis, Streptococcus pyogenes; Enterobacter aerogenes; Enterobacter cloacae* and *Strepto-*

*coccus pneumoniae*. All exemplified compounds have a MIC values for *Staphylococcus aureus* ATCC29213, *Staphylococcus epidermidis* ATCC14990 and *Streptococcus pneumoniae* ATCC49619 lower or equal to 8 mg/L except examples 25 and 56 for *Staphylococcus epidermidis* ATCC14990 and examples 20, 49, 51, 56, 58, 60, 66 and 76 for *Streptococcus pneumoniae* ATCC4961. Examples 1-6, 11, 17, 18, 27, 28, 35, 36, 39, 45, 46, 54 and 64 showed an MIC value of 8 mg/L or lower for *Escherichia coli* ATCC2592.

The invention claimed is:

1. A compound of formula (I):

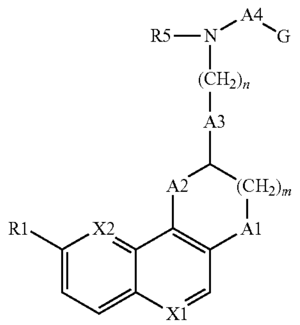

(I)

wherein:

A1 represents —O—, —S— or —N(R3)-;

A2 represents —$CH_2$—, —O—, —N(R4)-, —C(═O )— or —CH(O—R4)-;

A3 represents $C_3$-$C_8$cycloalkylene; saturated or unsaturated 4 to 8-membered heterocyclodiyl with 1, 2 or 3 heteroatoms selected from the group consisting of nitrogen, oxygen and sulphur, wherein A3 is unsubstituted or substituted by a substituent selected from the group consisting of hydroxyl, $C_1$-$C_4$alkyl, $C_1$-$C_4$alkoxy, cyano, aminocarbonyl, ($C_1$-$C_4$alkyl)aminocarbonyl, $C_1$-$C_4$alkoxycarbonyl and a carboxylic acid group;

A4 represents $C_1$-$C_4$alkylene, $C_2$-$C_4$alkenylene, >C═O or a group selected from —$C_2H_4NH$—, —$C_2H_4O$—, and —$C_2H_4S$— being linked to the adjacent NR5-group via the carbon atom; and G represents a unsubstituted or substituted benzo[1,4]oxazine or a pyrido[1,4]oxazine group, wherein the benzo or pyrido moiety of the benzo[1,4]oxazine or a pyrido [1,4]oxazine group may be substituted by one or more substituents selected from the group consisting of a fluorine, a chlorine, a bromine and a iodine atom; a carboxy group, a $C_1$-$C_4$alkyl group, which is unsubstituted or further substituted by fluoro; an alkoxy group, a mono- or di($C_1$-$C_4$alkyl)amino group, an OH group, SH group, $NH_2$ group, cyano group and $NO_2$ group and the oxazine moiety fused to said aryl or heteroaryl group may be substituted by one of more substituents selected from the group consisting of a fluorine, chlorine, bromine and iodine atom and a carboxy, alkyl, alkoxy, mono- or di($C_1$-$C_4$alkyl)amino, OH, SH, $NH_2$, cyano, $NO_2$, ═O, ═S and ═NH group;

R1 and R2 independently of one another, represent hydrogen or a substituent selected from the group consisting of hydroxy, halogen, mercapto, cyano, nitro, $C_1$-$C_6$alkyl, $C_1$-$C_6$alkoxy, $C_1$-$C_6$alkylthio, $C_1$-$C_6$alkylcarbonyloxy, $C_1$-$C_6$alkylsulfonyloxy, $C_1$-$C_6$heteroalkylcarbonyloxy, $C_5$-$C_6$heterocyclylcarbonyloxy and $C_1$-$C_6$heteroalkoxy, wherein the heteroalkyl, heteroalkoxy or heterocyclyl substituent comprise 1, 2 or 3 heteroatoms selected from the group consisting of nitrogen, oxygen and sulphur, and in which the alkyl moieties in the alkyl containing substituents are unsubstituted;

R3, R4 and R5 independently of one another, represent hydrogen or $C_1$-$C_6$alkyl;

X1 and X2 independently of one another, represent a nitrogen atom or CR2, with the proviso that at least one of X1 and X2 represents a nitrogen atom;

m is 1; and the $(CH_2)_m$ moiety linked to A1 in formula (I) is optionally substituted by $C_1$-$C_4$alkyl; halogen, carboxy, hydroxy, $C_1$-$C_4$alkoxy, $C_1$-$C_4$-alkylcarbonyloxy, amino, mono- or di-($C_1$-$C_4$alkyl)amino or acylamino;

n is 0, 1 or 2 or a pharmaceutically acceptable salt, hydrate or solvate thereof.

2. The compound according to claim 1 or a pharmaceutically acceptable salt, hydrate or solvate thereof, wherein X1 represents a nitrogen atom and X2 represents a group CR2.

3. The compound according to claim 1 or a pharmaceutically acceptable salt, hydrate or solvate thereof, wherein A1 represents —O— or —S—.

4. The compound according to claim 1 or a pharmaceutically acceptable salt, hydrate or solvate thereof, wherein A2 represents —$CH_2$—.

5. The compound according to claim 1 or a pharmaceutically acceptable salt, hydrate or solvate thereof, wherein A3 is a cyclohexylene group or saturated and unsaturated 4 to 6-membered heterocyclodiyl with 1 or 2 nitrogen atoms as heteroatoms.

6. The compound according to claim 5 or a pharmaceutically acceptable salt, hydrate or solvate thereof, wherein A3 is selected from the group consisting of:

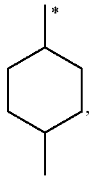, 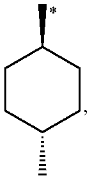, 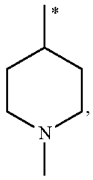, 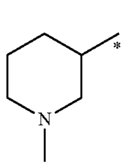,

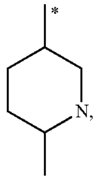 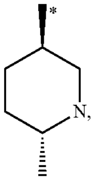 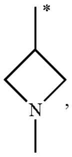, 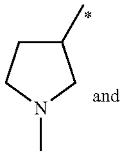 and

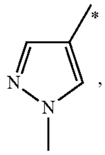, wherein

* indicates the bond to the ($CH_2$) group in formula (I).

7. The compound according to claim 6 or a pharmaceutically acceptable salt, hydrate or solvate thereof, wherein A3 is selected from the group consisting of:

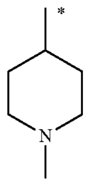

and

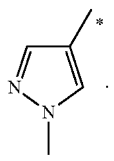

.

8. The compound according to claim 1 or a pharmaceutically acceptable salt, hydrate or solvate thereof, wherein n is 0.

9. The compound according to claim 1 or a pharmaceutically acceptable salt, hydrate or solvate thereof, wherein A4 is $C_1$-$C_4$alkylene or >C═O.

10. The compound according to claim 1 or a pharmaceutically acceptable salt, hydrate or solvate thereof, wherein R1 is selected from the group consisting of halogen and $C_1$-$C_6$alkoxy.

11. The compound according to claim 1 or a pharmaceutically acceptable salt, hydrate or solvate thereof, having at least 2 of the following features in combination:

(a) X1 is a nitrogen atom and X2 is CH;

(b) A1 is —S— or —O—;

(c) A2 is —$CH_2$—;

(d) A3 is

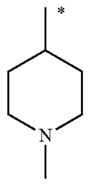

or

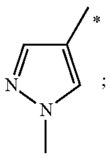

;

(e) G is

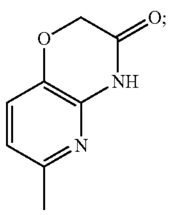

;

(f)n n is 0;

(g) A4 is $C_1$-$C_4$alkylene or >C═O;

(h) R1 is $C_1$-$C_4$alkoxy.

12. The compound according to claim 1 or a pharmaceutically acceptable salt, hydrate or solvate thereof, wherein A4 represents $C_1$-$C_4$alkylene, —C(═O)— or a group —$C_2H_4$S— being linked to the adjacent NR5-group via the carbon atom;

R1 and R2 independently of one another, represent hydrogen or a substituent selected from hydroxy, halogen, cyano, $C_1$-$C_6$alkyl, or $C_1$-$C_6$alkoxy, in which substituents the alkyl moieties are unsubstituted; and n is 0 or 1.

13. The compound according to claim 1 or a pharmaceutically acceptable salt, hydrate or solvate thereof, wherein X1 represents a nitrogen atom and X2 represents a nitrogen atom.

14. The compound according to claim 1 or a pharmaceutically acceptable salt, hydrate or solvate thereof, wherein A2 represents —NH—.

15. The compound according to claim 1 or a pharmaceutically acceptable salt, hydrate or solvate thereof, wherein R1 is $C_1$-$C_3$alkyl.

16. The compound according to claim 1 or a pharmaceutically acceptable salt, hydrate or solvate thereof, wherein A3 is selected from the group consisting of:

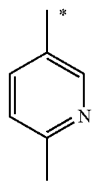

and

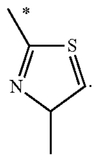

.

wherein

* indicates the bond to the ($CH_2$) group in formula (I).

17. The compound according to claim 15 or a pharmaceutically acceptable salt, hydrate or solvate thereof, wherein A3 is selected from the group consisting of:

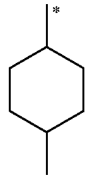

and

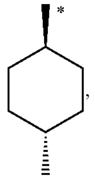

, wherein

* indicates the bond to the ($CH_2$) group in formula (I).

18. A process for the preparation of a compound of formula I as claimed in claim 1 comprising reacting a compound of the formula II (II)

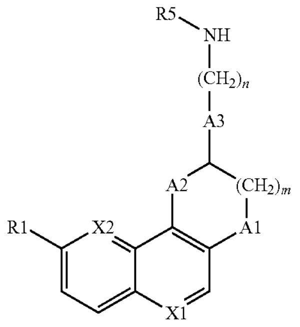

with a compound of formula III

G-A4b-L0 (III)

in which formulae

A1, A2, A3, G, R1, R5, X1, X2, m and n are as in formula I and the $(CH_2)_m$ moiety linked to A1 is optionally substituted by $C_1$-$C_4$alkyl; halogen, carboxy, hydroxy, $C_1$-$C_4$alkoxy, $C_1$-$C_4$-alkylcarbonyloxy, amino, mono- or di-($C_1$-$C_4$alkyl)amino or acylamino, L0 is selected from the group consisting of $—CH_2Y$, —CHO, —COOH and —COCl, Y is mesylate, tosylate, triflate or halogen;

A4b is absent or represents $C_1$-$C_3$alkylene, $C_2$-$C_3$alkenylene; or a radical selected from the group consisting of $—CH_2NH—$, $—CH_2O—$, and $—CH_2S—$, said radical being linked to G via the nitrogen, oxygen or sulfur atom.

19. A process for the preparation of a compound of formula I as claimed in claim 1 comprising reacting a compound of formula IV (IV)

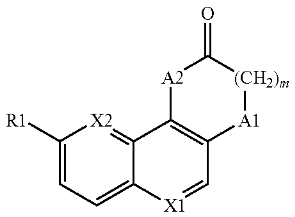

with a compound of formula V (V)

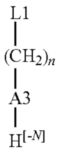

to generate a compound of formula VI (VI)

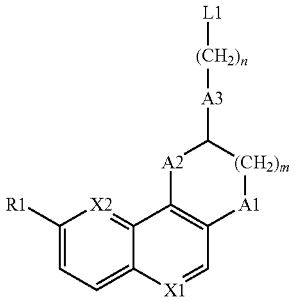

in which formulae

A1, A2, R1, X1, X2, m and n are as in formula I and the $(CH_2)_m$ moiety linked to A1 is optionally substituted by $C_1$-$C_4$alkyl; halogen, carboxy, hydroxy, $C_1$-$C_4$alkoxy, $C_1$-$C_4$-alkylcarbonyloxy, amino, mono- or di-($C_1$-$C_4$alkyl)amino or acylamino, A3 is a saturated or unsaturated 4 to 8-membered heterocyclodiyl group with 1, 2 or 3 heteroatoms selected from the group consisting of nitrogen, oxygen and sulphur, at least one of which heteroatoms is a nitrogen atom, and is unsubstituted or substituted by a substituent selected from the group consisting of $C_1$-$C_4$alkoxy, cyano, aminocarbonyl, ($C_1$-$C_4$alkyl)aminocarbonyl, $C_1$-$C_4$alkoxycarbonyl and a carboxylic acid group and $H^{[-N]}$ represents a hydrogen atom bound to a nitrogen ring atom of A3, L1 is nitro or N(R5)E.

R5 is as defined in formula I,

E is an amino protecting group or a group of formula -A4-G, wherein

A4 and G have the same meaning as in formula I, and when L1 is nitro, the nitro group is reduced to an amino group and the amino derivative obtained is reacted with a compound of formula III G-A4b-L0 (III), wherein G is as defined in formula (I), L0 is selected from the group consisting of $—CH_2Y$, —CHO, —COOH and —COCl, Y is mesylate, tosylate, triflate or halogen, and A4b is absent or represents $C_1$-$C_3$alkylene, $C_2$-$C_3$alkenylene; or a radical selected from the group consisting of $—CH_2NH—$, $—CH_2O—$, and $—CH_2S—$, said radical being linked to G via the nitrogen, oxygen or sulfur atom; or when L1 is N(R5)E and E is an amino protecting group said protecting group is removed and the deprotected intermediate is reacted with a compound of formula III above.

20. A process for the preparation of a compound of formula I, as claimed in claim 1 wherein in formula I A1 is —O— and A2 is $—CH_2—$, m is 1 and the $(CH_2)_m$ moiety linked to A1 is unsubstituted, comprising reacting a compound of formula VII (VII)

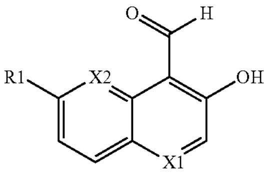

with a compound of formula VIII (VIII)

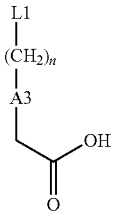

to generate a compound of formula IX (IX)

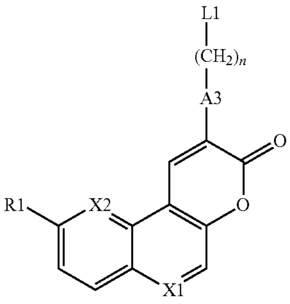

in which formulae

X1, X2, R1 and n are as in formula I,

A3 is a saturated or unsaturated 4 to 8-membered heterocyclodiyl group with 1, 2 or 3 heteroatoms selected from the group consisting of nitrogen, oxygen and sulphur, wherein at least one of the heteroatoms is a nitrogen atom and one nitrogen heteroatom of A3 is linked to the terminal $—CH_2—COOH$ in the compound of formula VIII, which group A3 is n unsubstituted or substituted by a substituent selected from the group consisting of $C_1$-$C_4$alkoxy, cyano, aminocarbonyl, ($C_1$-$C_4$alkyl)aminocarbonyl, $C_1$-$C_4$alkoxycarbonyl and a carboxylic acid group, and L1 is nitro or N(R5)E, R5 is as defined in formula I, and E is an amino protecting group or a group of formula -A4-G, wherein A4 and G have the same meaning as in formula I;

the compound of formula IX is reduced to convert it to the compound of formula XI (XI)

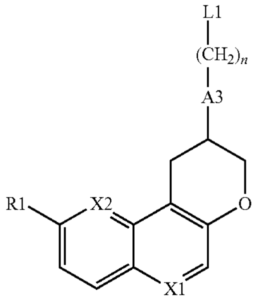

wherein A3, L1, R1, X1, X2, and n are as defined above; and when L1 is nitro, said nitro group is reduced to an amino group and the amino derivative obtained is reacted with a compound of formula III G-A4b-L0 (III), wherein G is as defined in formula (I), L0 is selected from the group consisting of —$CH_2$Y, —CHO, —COOH and —COCl, Y is mesylate, tosylate, triflate or halogen, and A4b is absent or represents $C_1$-$C_3$alkylene, $C_2$-$C_3$alkenylene; or a radical selected from the group consisting of —$CH_2$NH—, —$CH_2$O—, and —$CH_2$S—, said radical being linked to G via the nitrogen, oxygen or sulfur atom; or when L1 is N(R5)E and E is an amino protecting group said protecting group is removed and the deprotected intermediate is reacted with a compound of formula III as defined above.

21. A process for the preparation of a compound of formula I as claimed in claim 1 wherein in formula I A2 is —O— or —N(R4)-, m is 1 and the $(CH_2)_m$ moiety linked to A1 is unsubstituted, comprising reacting a compound of formula XIII (XIII)

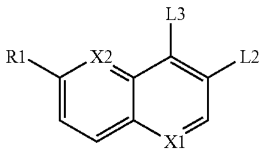

with a compound of formula XIV (XIV)

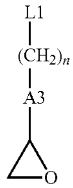

to generate a compound of formula XV (XV)

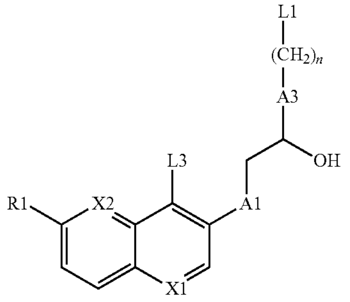

in which formulae

A1, A3, R1, X1, X2 and n are as in formula I,

L1 nitro or N(R5)E,

R5 is as defined in formula I, and

E is an amino protecting group PG1 or a group of formula -A4-G, wherein

A4 and G have the same meaning as in formula I;

L2 is -A1-H,

L3 is a halogen atom or —N(R4)PG2 wherein R4 is as in formula (I) and PG2 is an amino protecting group, said compound of formula XV is then converted to the compound of formula XVI (XVI)

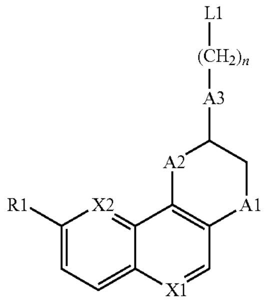

wherein A1, A2, A3, X1, X2, L1, R1 and n are as defined above, and when L1 is nitro, said nitro group is reduced to an amino group and the amino derivative obtained is reacted with a compound of formula III G-A4b-L0 (III), wherein G is as defined in formula (I), L0 is selected from the group consisting of —$CH_2$Y, —CHO, —COOH and —COCl, Y is mesylate, tosylate, triflate or halogen, and A4b is absent or represents $C_1$-$C_3$alkylene, $C_1$-$C_3$alkenylene or a radical selected from the group consisting of —$CH_2NH$—, —$CH_2O$—, and —$CH_2S$—, said radical being linked to G via the nitrogen, oxygen or sulfur atom; or when L1 is N(R5)E and E is an amino protecting group said protecting group is removed and the deprotected intermediate is reacted with a compound of formula III as defined above.

22. A process for the preparation of a compound of formula I, as claimed in claim 1 wherein in formula I A2 is —$CH_2$— or —N(R4)-, m is 1 and the $(CH_2)_m$ moiety linked to A1 is unsubstituted, comprising reacting a compound of formula XIII (XIII)

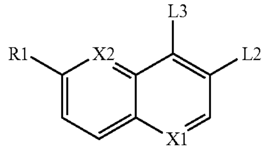

with a compound of formula XVIII (XVIII)

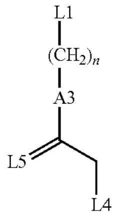

to generate a compound of formula XIX (XIX)

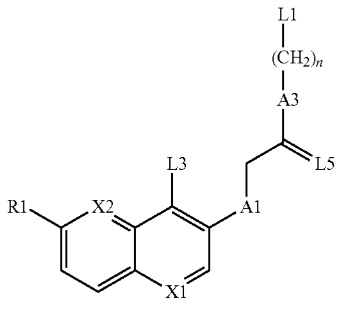

in which formulae

A1, A3, R1, X1, X2 and n are as in formula I,

L1 is nitro or N(R5)E,

R5 is as defined in formula I, and

E is an amino protecting group PG1 or a group of formula -A4-G, wherein

A4 and G have the same meaning as in formula I;

L2 is -A1-H,

L3 is a halogen atom or —N(R4)PG2 wherein R4 is as in formula (I) and PG2 is an amino protecting group, L4 is a halogen atom, L5 is $CH_2$ or O, said compound of formula XIX is then converted to the compound of formula XX (XX)

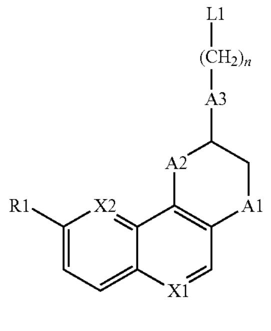

wherein A1, A2, A3, X1, X2, L1 , R1 and n are as defined above, and when L1 is nitro, said nitro group is reduced to an amino group and the amino derivative obtained is then reacted with a compound of formula III G-A4b-L0 (III), wherein G is as defined in formula (I), L0 is selected from the group consisting of —$CH_2Y$, —CHO, —COOH and —COCl, Y is mesylate, tosylate, triflate or halogen, and A4b is absent or represents $C_1$-$C_3$alkylene, $C_1$-$C_3$alkenylene or a radical selected from the group consisting of —$CH_2NH$—, —$CH_2O$—, and —$CH_2S$—, said radical being linked to G via the nitrogen, oxygen or sulfur atom; or when L1 is N(R5)E and E is an amino protecting group said protecting group is removed and the deprotected intermediate is reacted with a compound of formula III as defined above.

23. A process for the preparation of a compound of formula I as claimed in claim 1, wherein in formula I A1 is —O— and A2 is —$CH_2$—, m is 1 and the $(CH_2)$, moiety linked to A1 is unsubstituted, comprising reacting a compound of formula VII (VII)

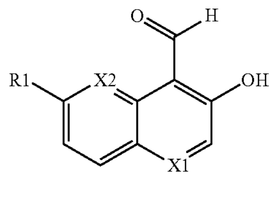

with a compound of formula XXII (XXII)

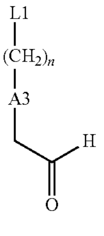

to generate a compound of formula XXIII (XXIII)

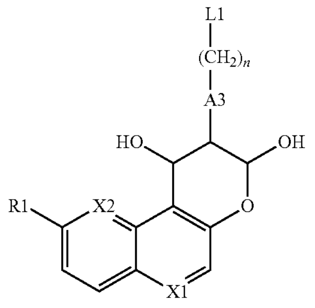

in which formulae

X1, X2, R1, A3 and n are as in formula I,

L1 is nitro or N(R5)E,

R5 is as in formula I, and

E is an amino protecting group PG1 or a group of formula -A4-G, wherein

A4 and G have the same meaning as in formula I, said compound of formula XXIII is then converted to the compound of formula X (X)

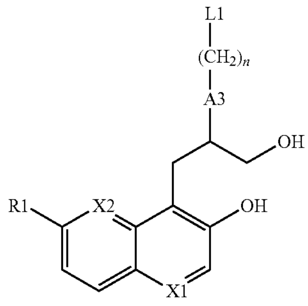

wherein X1, X2, R1, A3, L1 and n are as defined above, said compound of formula X is further transformed into compound of formula XI (XI)

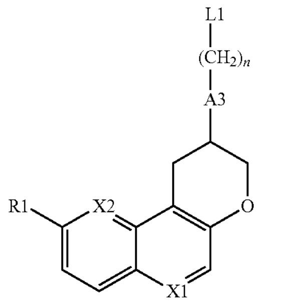

wherein X1, X2, R1, A3, L1 and n are as defined above and when L1 is nitro, said nitro group is reduced to an amino group and the amino derivative obtained is then reacted with a compound of formula III G-A4b-L0 (III), wherein G is as defined in formula (I), L0 is selected from the group consisting of —$CH_2$Y, —CHO, —COOH and —COCl, Y is mesylate, tosylate, triflate or halogen, and A4b is absent or represents $C_1$-$C_3$alkylene, $C_1$-$C_3$alkenylene or a radical selected from the group consisting of—$CH_2$NH—, —$CH_2$O—, and —$CH_2$S—, said radical being linked to G via the nitrogen, oxygen or sulfur atom; or when L1 is N(R5)E and E is an amino protecting group said protecting group is removed and the deprotected intermediate is reacted with a compound of formula III as defined above.

24. A process for the preparation of a compound of formula I as claimed in claim 1 wherein in formula I A1 is —N(R3)-, A2 is —O—, m is 1 and the $(CH_2)_m$ moiety linked to A1 is unsubstituted, comprising reacting a compound of formula XXV (XXV)

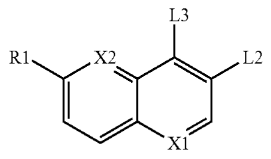

with a compound of formula XXVI (XXVI)

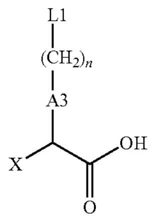

to generate a compound of formula XXVII (XXVII)

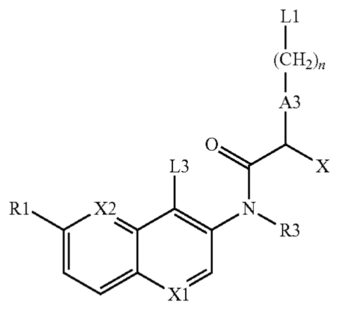

in which formulae

X1, X2, A3, R1, R3 and n are as defined for formula I,

L1 is nitro or N(R5)E,

R5 is as in formula I, and

E is an amino protecting group PG1 or a group of formula -A4-G, wherein

A4 and G have the same meaning as in formula I,

L2 is —NHR3 or —N(R3)PG2 wherein PG2 is an amino protecting group,

L3 is —OH or —OPG3 wherein PG3 is a phenol protecting group,

X is a halogen atom, said compound of formula XXVII is further transformed and cyclized to generate a compound of formula XXVIII (XXVIII)

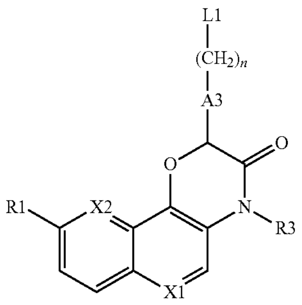

wherein A3, X1, X2, L1, R1, R3 and n are as defined above, said compound of formula XXVIII is then reduced into compound of formula XXIX (XXIX)

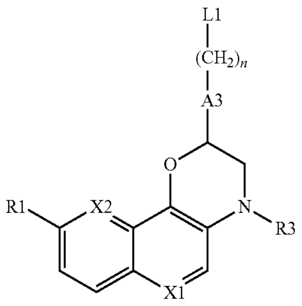

wherein A3, X1, X2, L1, R1, R3 and n are as defined above and when L1 is nitro, said nitro group is reduced to an amino group and the amino derivative obtained is then reacted with a compound of formula III G-A4b-L0 (III), wherein G is as defined in formula (I), L0 is selected from the group consisting of —$CH_2Y$, —CHO, —COOH and —COCl, Y is mesylate, tosylate, triflate or halogen, and A4b is absent or represents $C_1$-$C_3$alkylene, $C_1$-$C_3$alkenylene or a radical selected from the group consisting of —$CH_2NH$—, —$CH_2O$—, and —$CH_2S$—, said radical being linked to G via the nitrogen, oxygen or sulfur atom; or when L1 is N(R5)E and E is an amino protecting group said protecting group is removed and the deprotected intermediate is reacted with a compound of formula III as defined above.

25. A process for the preparation of a compound of formula I as claimed in claim 1, wherein in formula I A1 is —N(R3)-, A2 is —$CH_2$—, m is 1 and the ($CH_2$)$_m$ moiety linked to A1 is unsubstituted, comprising reacting a compound of formula XXXI (XXXI)

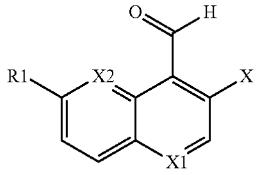

with a compound of formula XXII (XXII)

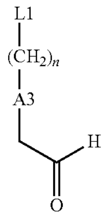

to generate a compound of formula XXXII (XXXII)

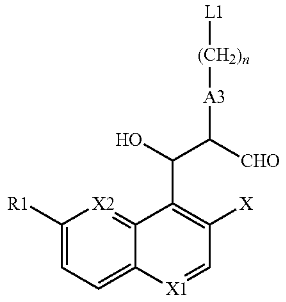

in which formulae

X1, X2, R1, A3 and n are as in formula I,

L1 is nitro or N(R5)E,

R5 is as in formula I, and

E is an amino protecting group PG1 or a group of formula -A4-G, wherein

A4 and G have the same meaning as in formula I,

X is a halogen atom, said compound of formula XXXII is further converted into a compound of formula XXXV (XXXV)

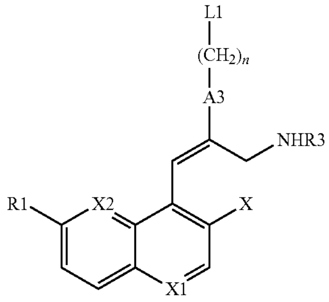

wherein X1, X2, R1, R3, A3, L1 and n are as defined above, said compound of formula XXXV is further cyclized and reduced to generate compound of formula XXXVII (XXXVII)

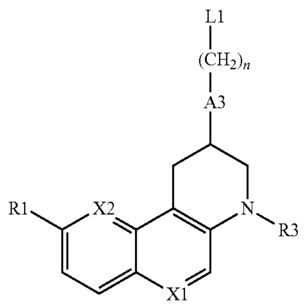

wherein X1, X2, R1, R3, A3, L1 and n are as defined above and when L1 is nitro, said nitro group is reduced to an amino group and the amino derivative obtained is then reacted with a compound of formula III G-A4b-L0 (III), wherein G is as defined in formula (I), L0 is selected from the group consisting of —$CH_2Y$, —CHO, —COOH and —COCl, Y is mesylate, tosylate, triflate or halogen, and A4b is absent or represents $C_1$-$C_3$alkylene, $C_1$-$C_3$alkenylene or a radical selected from the group consisting of —$CH_2NH$—, —$CH_2O$—, and —$CH_2S$—, said radical being linked to G via the nitrogen, oxygen or sulfur atom; or when L1 is N(R5)E and E is an amino protecting group said protecting group is removed and the deprotected intermediate is reacted with a compound of formula III as defined above.

26. The compound of claim 1 or the pharmaceutically acceptable salt, hydrate or solvate thereof wherein R1 is fluoro.

27. The compound of claim 1 or the pharmaceutically acceptable salt, hydrate or solvate thereof wherein R1 is methoxy.

28. The compound of claim 1 or the pharmaceutically acceptable salt, hydrate or solvate thereof wherein A4 is methylene.

29. The compound of claim 11 or the pharmaceutically acceptable salt, hydrate or solvate thereof wherein A1 is —O—.

30. The compound of claim 11 or the pharmaceutically acceptable salt, hydrate or solvate thereof wherein A4 is methylene.

31. The compound of claim 11 or the pharmaceutically acceptable salt, hydrate or solvate thereof wherein R1 is methoxy.

32. The compound of claim 11 or the pharmaceutically acceptable salt, hydrate or solvate thereof wherein the compound contains all of the features (a) through (h) in combination.

33. The compound of claim 32 or the pharmaceutically acceptable salt, hydrate or solvate thereof wherein A1 is —O—.

34. The compound of claim 32 or the pharmaceutically acceptable salt, hydrate or solvate thereof wherein A4 is methylene.

35. The compound of claim 32 or the pharmaceutically acceptable salt, hydrate or solvate thereof wherein R1 is methoxy.

36. The compound of claim 1 or the pharmaceutically acceptable salt, hydrate or solvate thereof, wherein the benzo or pyrido moiety of the benzo[1,4]oxazine or a pyrido[1,4]oxazine group is unsubstituted or substituted by one or more halogen atoms or straight-chain or branched $C_1$-$C_4$alkyl groups, which are unsubstituted or further substituted by fluoro, and wherein the oxazine moiety of the benzo[1,4]oxazine or a pyrido[1,4]oxazine group is unsubstituted or substituted by a ═O group.

37. A compound of formula (I):

(I)

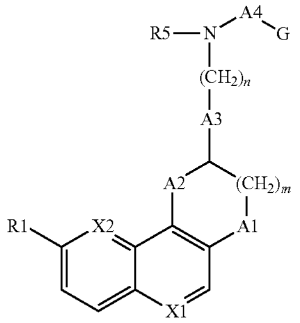

wherein

A1 represents —O—, —S— or N(R3)-;

A2 represents —$CH_2$—, —O—, —N(R4)-, —C(═O)— or —CH(O—R4)-;

A3 represents $C_3$-$C_8$cycloalkylene; saturated or unsaturated 4 to 8-membered heterocyclodiyl with 1, 2 or 3 heteroatoms selected from the group consisting of nitrogen, oxygen and sulphur, wherein A3 is unsubstituted or substituted by a substituent selected from the group consisting of hydroxyl, $C_1$-$C_4$alkyl, $C_1$-$C_4$alkoxy, cyano, aminocarbonyl, ($C_1$-$C_4$alkyl)aminocarbonyl, $C_1$-$C_4$alkoxycarbonyl and a carboxylic acid group;

A4 represents $C_1$-$C_4$alkylene, $C_2$-$C_4$alkenylene, >C═O or a group selected from —$C_2H_4NH$—, —$C_2H_4O$—, and —$C_2H_4S$— being linked to the adjacent NR5-group via the carbon atom; and G represents a group of formula

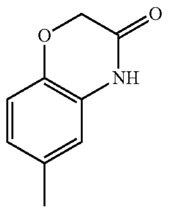

or

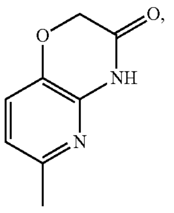

R1 and R2 independently of one another, represent hydrogen or a substituent selected from the group consisting of hydroxy, halogen, mercapto, cyano, nitro, $C_1$-$C_6$alkyl, $C_1$-$C_6$alkoxy, $C_1$-$C_6$alkylthio, $C_1$-$C_6$alkylcarbonyloxy, $C_1$-$C_6$alkylsulfonyloxy, $C_1$-$C_6$heteroalkylcarbonyloxy, $C_5$-$C_6$heterocyclylcarbonyloxy and $C_1$-$C_6$heteroalkoxy, wherein the heteroalkyl, heteroalkoxy or heterocyclyl substituent comprise 1, 2 or 3 heteroatoms selected from the group consisting of nitrogen, oxygen and sulphur, and in which the alkyl moieties in the alkyl containing substituents are unsubstituted;

R3, R4 and R5 independently of one another, represent hydrogen or $C_1$-$C_6$alkyl;

X1 and X2 independently of one another, represent a nitrogen atom or CR2, with the proviso that at least one of X1 and X2 represents a nitrogen atom;

m is 1; and the $(CH_2)_m$ moiety linked to A1 in formula (I) is optionally substituted by $C_1$-$C_4$alkyl; halogen, carboxy, hydroxy, $C_1$-$C_4$alkoxy, $C_1$-$C_4$-alkylcarbonyloxy, amino, mono- or di-($C_1$-$C_4$alkyl)amino or acylamino;

n is 0, 1 or 2 or a pharmaceutically acceptable salt, hydrate or solvate thereof.

38. The compound according to claim 37 which is selected from the group consisting of:

6-{[1-(6-Methoxy-3,4-dihydro-2H-1-thia-9-aza-phenanthren-3-yl)-piperidin-4-ylamino]-methyl}-4H-benzo[1,4]oxazin-3-one;

3-Oxo-3,4-dihydro-2H-benzo[1,4]oxazine-6-carboxylic acid [1-(6-methoxy-3,4-dihydro-2H-1-oxa-9-aza-phenanthren-3-yl)-piperidin-4-yl]-amide;

6-{[1-(6-Methoxy-3,4-dihydro-2H-1-thia-9-aza-phenanthren-3-yl)-piperidin-4-ylamino]-methyl}-4H-pyrido[3,2-b][1,4]oxazin-3 -one;

3-Oxo-3,4-dihydro-2H-benzo[1,4]oxazine-6-carboxylic acid [4-(6-methoxy-3,4-dihydro-2H-1-oxa-9-aza-phenanthren-3-yl)-cyclohexyl]-amide;

6-{[4-(6-Methoxy-3,4-dihydro-2H-1-oxa-9-aza-phenanthren-3-yl)-cyclohexylamino]-methyl}-4H-pyrido[3,2-b][1,4]oxazin-3-one;

3-Oxo-3,4-dihydro-2H-pyrido[3,2-b][1,4]oxazine-6-carboxylic acid [1-(6-methoxy-3,4-dihydro-2H-1-thia-9-aza-phenanthren-3-yl)-piperidin-4-yl]-amide;

3-Oxo-3,4-dihydro-2H-benzo[1,4]oxazine-6-carboxylic acid [1-(5-fluoro-6-methoxy-3,4-dihydro-2H-1-oxa-9-aza-phenanthren-3-yl)-piperidin-4-yl]-amide;

3-Oxo-3,4-dihydro-2H-pyrido[3,2-b][1,4]oxazine-6-carboxylic acid [4-(6-methoxy-3,4-dihydro-2H-1-oxa-9-aza-phenanthren-3-yl)-cyclohexyl]-amide;

3-Oxo-3,4-dihydro-2H-pyrido[3,2-b][1,4]oxazine-6-carboxylic acid [1-(5-fluoro-6-methoxy-3,4-dihydro-2H-1-oxa-9-aza-phenanthren-3-yl)-piperidin-4-yl]-amide;

3-Oxo-3,4-dihydro-2H-benzo[1,4]oxazine-6-carboxylic acid [4-(6-methoxy-3,4-dihydro-2H-1-oxa-4,5,9-triaza-phenanthren-3-yl)-cyclohexyl]-amide;

3-Oxo-3,4-dihydro-2H-benzo[1,4]oxazine-6-carboxylic acid [4-(6-methoxy-3,4-dihydro-2H-1-oxa-5,9-diaza-phenanthren-3-yl)-cyclohexyl]-amide;

3-Oxo-3,4-dihydro-2H-pyrido[3,2-b][1,4]oxazine-6-carboxylic acid [1-(6-methoxy-3,4-dihydro-2H-1-oxa-9-aza-phenanthren-3-yl)-piperidin-4-yl]-amide;

3-Oxo-3,4-dihydro-2H-pyrido[3,2-b][1,4]oxazine-6-carboxylic acid [4-(3,4-dihydro-2H-1-oxa-9-aza-phenanthren-3-yl)-cyclohexyl]-amide;

3-Oxo-3,4-dihydro-2H-benzo[1,4]oxazine-6-carboxylic acid [4-(6-fluoro-3,4-dihydro-2H-1-oxa-9-aza-phenanthren-3-yl)-cyclohexyl]-amide;

3-Oxo-3,4-dihydro-2H-pyrido[3,2-b][1,4]oxazine-6-carboxylic acid [4-(6-fluoro-3,4-dihydro-2H-1-oxa-9-aza-phenanthren-3-yl)-cyclohexyl]-amide;

3-Oxo-3,4-dihydro-2H-benzo[1,4]oxazine-6-carboxylic acid [4-(3,4-dihydro-2H-1-oxa-9-aza-phenanthren-3-yl)-cyclohexyl]-amide;

3-Oxo-3,4-dihydro-2H-pyrido[3,2-b][1,4]oxazine-6-carboxylic acid [1-(6-methoxy-3,4-dihydro-2H-1-oxa-9-aza-phenanthren-3-yl)-pyrrolidin-3-yl]-amide;

3-Oxo-3,4-dihydro-2H-benzo[1,4]oxazine-6-carboxylic acid [1-(6-methoxy-3,4-dihydro-2H-1-oxa-5 ,9-diaza-phenanthren-3 -yl)- 1H-pyrazol-4-yl]-amide;

3-Oxo-3,4-dihydro-2H-pyrido[3,2-b][1,4]oxazine-6-carboxylic acid [1-(6-methoxy-3,4-dihydro-2H- 1 -oxa-5,9-diaza-phenanthren-3-yl)-1H-pyrazol-4-yl]-amide;

6-{[1-(6-Methoxy-3,4-dihydro-2H-1-oxa-5,9-diaza-phenanthren-3-yl)-1H-pyrazol-4-ylamino]-methyl}-4H-pyrido [3,2-b][1,4]oxazin-3-one;

6-{[1-(6-Methoxy-3,4-dihydro-2H-1-oxa-5,9-diaza-phenanthren-3-yl)-1H-pyrazol-4-ylamino]-methyl}-4H-benzo[1,4]oxazin-3-one and pharmaceutically acceptable salts, hydrates or solvates thereof.

39. The compound of claim 38, which is:

3-Oxo-3,4-dihydro-2H-benzo[1,4]oxazine-6-carboxylic acid [1-(6-methoxy-3,4-dihydro-2H-1-oxa-9-aza-phenanthren-3-yl)-piperidin-4-yl]-amide or a pharmaceutically acceptable salts, hydrates or solvates thereof.

40. The compound of claim 38, which is:

3 -Oxo-3 ,4-dihydro-2H-benzo [1,4]oxazine-6-carboxylic acid [4-(6-methoxy-3,4-dihydro-2H-1-oxa-9-aza-phenanthren-3-yl)-cyclohexyl]-amide or a pharmaceutically acceptable salts, hydrates or solvates thereof.

41. The compound of claim 38, which is:

3-Oxo-3,4-dihydro-2H-pyrido [3,2-b][1,4]oxazine-6-carboxylic acid [1-(6-methoxy-3,4-dihydro-2H-1-thia-9-aza-phenanthren-3-yl)-piperidin-4-yl]-amide or a pharmaceutically acceptable salts, hydrates or solvates thereof.

42. The compound of claim 38, which is:

3-Oxo-3,4-dihydro-2H-benzo[1,4]oxazine-6-carboxylic acid [1-(5-fluoro-6-methoxy-3,4-dihydro-2H-1-oxa-9-aza-phenanthren-3-yl)-piperidin-4-yl]-amide or a pharmaceutically acceptable salts, hydrates or solvates thereof.

43. The compound of claim 38, which is:

3-Oxo-3,4-dihydro-2H-pyrido[3,2-b][1,4]oxazine-6-carboxylic acid [4-(6-methoxy-3,4-dihydro-2H-1-oxa-9-aza-phenanthren-3-yl)-cyclohexyl]-amide or a pharmaceutically acceptable salts, hydrates or solvates thereof.

44. The compound of claim 38, which is:

3 -Oxo-3,4-dihydro-2H-pyrido [3,2-b][1,4]oxazine-6-carboxylic acid [1-(6-methoxy-3,4-dihydro-2H-1-oxa-9-aza-phenanthren-3-yl)-piperidin-4-yl]-amide or a pharmaceutically acceptable salts, hydrates or solvates thereof.

45. The compound according to claim 37 or a pharmaceutically acceptable salt, hydrate or solvate thereof, wherein A3 is unsubstituted.

46. A pharmaceutical composition comprising a compound of formula (I) as claimed in claim 1 or a pharmaceutically acceptable salt, hydrate of solvate thereof and a pharmaceutically acceptable carrier.

47. A method for the treatment of a bacterial infection in a subject in need of such treatment, wherein an antibacterially active amount of a compound of formula (I) as claimed in claim 1 is administered to said subject.

* * * * *